US00RE50997E

(19) United States
(12) Reissued Patent
Merbl et al.

(10) Patent Number: US RE50,997 E
(45) Date of Reissued Patent: Aug. 18, 2026

(54) DIAGNOSTIC METHOD BASED ON LARGE SCALE IDENTIFICATION OF POST-TRANSLATIONAL MODIFICATION OF PROTEINS

(71) Applicant: PRESIDENT AND FELLOWS OF HARVARD COLLEGE, Cambridge, MA (US)

(72) Inventors: Yifat Merbl, Jamaica Plain, MA (US); Marc W. Kirschner, Newton, MA (US)

(73) Assignee: PRESIDENT AND FELLOWS OF HARVARD COLLEGE

(21) Appl. No.: 18/483,944

(22) Filed: Oct. 10, 2023

Related U.S. Patent Documents

Reissue of:
(64) Patent No.: 11,333,668
Issued: May 17, 2022
Appl. No.: 14/796,408
Filed: Jul. 10, 2015

U.S. Applications:
(63) Continuation of application No. 12/696,866, filed on Jan. 29, 2010, now abandoned, which is a
(Continued)

(51) Int. Cl.
*G01N 33/68* (2006.01)
*G01N 33/575* (2026.01)

(52) U.S. Cl.
CPC ..... *G01N 33/6845* (2013.01); *G01N 33/5758* (2026.01); *G01N 33/6842* (2013.01);
(Continued)

(58) Field of Classification Search
None
See application file for complete search history.

(56) References Cited

U.S. PATENT DOCUMENTS 5,932,425 A 8/1999 Alkalay et al.
6,225,101 B1 * 5/2001 Mueller ..... C12N 9/1205 435/194

(Continued)

OTHER PUBLICATIONS

Ptacek et al., "Global analysis of protein phosphorylation in yeast", Nature 438(7068) 679-684 (2005).

(Continued)

*Primary Examiner* — Kevin S Orwig
(74) *Attorney, Agent, or Firm* — NIXON PEABODY LLP; David S. Resnick; Nicole D. Kling

(57) ABSTRACT

Methods for the large scale identification of post-translational modification states of proteins and enzyme activities for carrying out post-translational modification reactions involve the analysis of functional extracts from fresh and frozen samples using protein arrays. The methods and kits of the present invention can be used to analyze and characterize compounds for their effects on post-translational modifications and their pathways. The methods and kits can also be used to diagnose and characterize a wide variety of diseases and medical conditions, including cancer, neurodegenerative diseases, immune diseases, infectious diseases, genetic diseases, metabolic conditions, and drug effects using cells or body fluids of a patient.

12 Claims, 17 Drawing Sheets

Specification includes a Sequence Listing.

| Modifi-cation | E1 | E2 |
|---|---|---|
| ISG15 | UBE1L | UBCH8 |
| FUB1 | NA | NA |
| Nedd8 | APPBP1-U | UBC12 |
| Fat10 | UBA6/UBE | USE1 |
| sumo1 | SEA1/2 | ubc9 |
| sumo2 | SEA1/2 | ubc9 |
| sumo3 | SEA1/2 | ubc9 |
| Apg8 | Apg7 | Apg3 |
| Apg12 | Apg7 | Apg10 |
| Urm1 | Uba4 | NA |
| Hub1 | NA | NA |
| Ufm1 | Uba5 | Ufc1 |

Related U.S. Application Data continuation-in-part of application No. PCT/US2009/005670, filed on Oct. 19, 2009.

(60) Provisional application No. 61/196,461, filed on Oct. 17, 2008.

(52) U.S. Cl.
CPC ..... *G01N 2440/00* (2013.01); *G01N 2440/14* (2013.01); *G01N 2440/36* (2013.01); *G01N 2800/00* (2013.01); *G01N 2800/28* (2013.01); *G01N 2800/2821* (2013.01); *G01N 2800/2835* (2013.01)

(56) References Cited

U.S. PATENT DOCUMENTS

2003/0037350 A1* 2/2003 Glucksmann ..... C40B 30/04 800/8
2003/0119054 A1* 6/2003 Mrksich ..... C07F 9/65515 435/7.1
2003/0124138 A1* 7/2003 Smith ..... C07K 14/705 424/185.1
2003/0153014 A1* 8/2003 Shen ..... G01N 33/6842 435/7.9
2004/0038417 A1* 2/2004 Cahill ..... C12N 9/1205 436/86
2004/0107057 A1* 6/2004 Capaldi ..... C07K 1/00 702/27
2004/0265938 A1* 12/2004 Remacle ..... C12Q 1/485 435/7.92
2005/0079503 A1* 4/2005 Bowtell ..... A61P 35/00 435/6.14
2007/0003951 A1 1/2007 Van Dongen
2007/0155776 A1* 7/2007 Betschmann ..... A61K 31/4743 514/301
2007/0224644 A1* 9/2007 Liotta ..... G01N 33/68 435/7.1
2007/0264678 A1 11/2007 Vogel et al.
2008/0064606 A1* 3/2008 Mrksich ..... B82Y 30/00 506/7
2008/0138836 A1 6/2008 Michaud
2009/0098115 A1 4/2009 Crocker et al.
2010/0099096 A1 4/2010 Elledge et al.

OTHER PUBLICATIONS

Rape et al., "The processivity of multiubiquitination by the APC determines the order of substrate degradation", Cell 124(1) 89-103 (2006).
Reddy et al., "Ubiquitination by the anaphase-promoting complex drives spindle checkpoint inactivation", Nature 446(7138) 921-925 (2007).
Reynolds et al., "Abelson murine leukemia virus transformation-defective mutants with impaired P120-associated protein kinase activity", J Virol 36(2) 374-386 (1980).
Sadri-Valkili et al., "Mechanisms of disease: Histone modifications in Huntington's disease", Nat Clin Pract Neurol 2(6) 330-338 (2006).
Schnack et al., "Protein array analysis of oligomerization-induced changes in alpha-synuclein protein-protein interactions points to an interference with Cdc42 effector proteins", Neurscience 154(4) 1450-1457 (2008).
Schneider et al., "A glycopolypeptide (gp 100) is the main antigen detected by HTLV-III antisera", Med Microbiol Immunol 174(1) 35-42 (1985).
Shinbo et al., "Proper Sumo-1 conjugation is essential to DJ-1 to exert its full activities", Cell Death Differ 13(1) 96-108(2006).
Steffan et al., "Sumo modification of Huntingtin and Huntington's disease pathology", Science 304(5667) 100-104 (2004).
Sufan et al., "The role of von Hippel-Lindau tumor suppressor protein and hypoxia in renal clear cell carcinoma", Am J Physiol Renal Physiol 287(1) F1-F6 (2004).
Takahashi-Fujigasaki et al., "SUMOylation substrates in neuronal intranuclear inclusion disease", Neuropathol Appl Neurobiol 32(1) 92-100 (2006).
Tan et al., "Lysine 63-linked ubiquitination promotes the formation and autophagic clearance of protein inclusions associated with neurodegenerative diseases", Hum Mol Genet 17(3) 431-439 (2008).
Ueda et al., "Enhanced SUMOylation in polyglutamine diseases." Biochemical and Biophysical Research Communications 293(1):307-313 (2002).
Van Boekel et al., "Modifications of arginines and their role in autoimmunity", Autoimmun Rev 2(2) 57-62 (2003).
Wada et al., "The von Hippel-Lindau tumor suppressor gene product promotes, but is not essential for, NEDD8 conjugation to cullin-2", J Biol Chem 274(50) 36025-36029 (1999).
Yao et al., "Nitrosative stress linked to sporadic Parkinson's disease: S-nitrosylation of parkin regulates its E3 ubiquitin ligase activity", Proc Natl Acad Sci USA 101(29) 10810-10814 (2004).
Zhang et al., "Effects of aging and dietary restriction on ubiquitination, sumoylation, and the proteasome in the spleen", FEBS Lett 581(28) 554305547 (2007).
Zhong et al., "DJ-1 transcriptionally up-regulates the human tyrosine hydroxylase by inhibiting the sumoylation of pyrimidine tract-binding protein-associated splicing factor", J Biol Chem 281(30) 20940-20948 (2006).
Zhou et al., "Autoantigenic posttranslational modifications of proteins: does it apply to rheumatoid arthritis?", Curr Opin Rheumatol 14(3) 250-253 (2002).
Abel et al., "Epigenetic targets of HDAC inhibition in neurodegenerative and psychiatric disorders", Curr Opin Pharmacol 8(1) 57-64 (2008).
Adhikary et al., "The ubiquitin ligase HectH9 regulates transcriptional activation by Myc and is essential for tumor cell proliferation", Cell 123(3) 409-421 (2005).
Akimoto et al., "O—GIcNAc modification of nucleocytoplasmic proteins and diabetes", Med Mol Morphol 28(2) 84-91 (2005).
Ayad et al., "Identification of ubiquitin ligase substrates by in vitro expression cloning", Methods Enzymol 399:404-414 (2005).
Blough et al., "Glycosylation inhibitors block the expression of LAV/HTLV-III (HIV) glycoproteins", Biochem Biophys Res Commun 141(1) 33-38 (1986).
Braunstein et al., "Inhibitory factors associated with anaphase-promoting complex/cylosome in mitotic checkpoint"; Proc Natl Acad Sci USA 104(12) 4870-4875 (2007).
Brooks et al., "Ubiquitination, phosphorylation and acetylation: the molecular basis for p53 regulation", Curr Opin Cell Biol 15(2) 164-171 (2003).
Casalino et al., "Accumulation of Fra-1 in ras-transformed cells depends on both transcriptional autoregulation and MEK-dependent posttranslational stabilization", Mol Cell Biol 23(12) 4401-4415 (2003).
Choudhury et al., "Ubiquitination and proteasomal degradation of the BRCA1 tumor suppressor is regulated during cell cycle progression", J Biol Chem 279(32) 33909-33918 (2004).
Ciechanover et al., "The ubiquitin proteasome system in neurodegenerative diseases: sometimes the chicken, sometimes the egg", Neuron 40(2) 427-446 (2003).
Ciechanover et al., "Ubiquitin dependence of selective protein degradation demonstrated in the mammalian cell cycle mutant ts85", Cell 37(1) 57-66 (1984).
Conrad et al., "Immunogenicity and conformational properties of an N-linked glycosylated peptide epitope of human T-lymphotropic virus type 1 (HTLV-I)", Biomed Pept Proteins Nucleic Acids 1(2) 83-92 (1995).
Dery et al., "Twists and turns in the function of DNA damage signaling and repair proteins by post-translational modifications", DNA Repair (Amst) 6(5) 561-577 (2007).
Dias et al., "O—GIcNAc modification in diabetes and Alzheimer's disease", Mol Blosyst 3(11) 766-772 (2007).

(56) References Cited

OTHER PUBLICATIONS

Doyle et al., "Posttranslational protein modifications: new flavors in the menu of autoantigens", Curr Opin Theumatol 14(3) 244-249 (2002).
Evans et al., "Cyclin: a protein specified by maternal mRNA in sea urchin eggs that is destroyed at each cleavage division", Cell 33(2) 389-396 (1983).
Fang et al., "Control of mitotic transitions by the anaphase-promoting complex", Philos Trans R Soc Lond B Biol Sci 354(1389) 1583-1590 (1999).
Fujioka et al., "Inhibition of constitutive NF-kappa B activity by I kappa B alpha M suppresses tumorigenesis", Oncogene 22(9) 1365-1370 (2003).
Gaczynska et al., "Caretaker or undertaker? The role of the proteasome in aging", Mech Ageing Dev 122(3) 235-254 (2001).
Glotzer et al., "Cyclin is degraded by the ubiquitin pathway", Nature 349(6305) 132-138 (1991).
Grillari et al., "Aging and the ubiquitinome: traditional and non-traditional functions of ubiquitin in aging cells and tissues", Exp Gerontol 41(11) 1067-1079 (2006).
Gujral et al., "Profiling phospho-signaling networks in breast cancer using reverse-phase protein arrays", Oncogene 32(29) 3470-3476 (2013).
Gupta et al., "Ubiquitination screen using protein microarrays for comprehensive identification of Rsp5 substrates in yeast", Mol Syt Biol 3: 116 (2007).
Haraguchi et al., "Asparagine-linked glycosylation of the scrapie and cellular prion proteins", Arch Biochem Biophys 274(1) 1-13 (1989).
Harauz et al., "A tale of two citrullines—structural and functional aspects of myelin basic protein deimination in health and disease", Neurochem Res 32(2) 137-158 (2007).
Harbers et al., "Provirus integration into a gene encoding a ubiquitin-conjugating enzyme results in a placental defect and embryonic lethality", Proc Natl Acad Sci USA 93(22) 12412-12417 (1996).
Hilhorst et al., "Peptide microarrays for profiling of serine/threonine kinase activity of recombinant kinases and lysates of cells and tissue samples", Methods Mol Biol 977: 259-271 (2013).
Jones et al., "A bittersweet modification: O—GIcNAc and cardiac dysfunction", Circ Res 96(9) 925-926 (2005).
Kim et al., "Multiple sclerosis: an important role for post-translational modifications of myelin basic protein in pathogenesis", Mol Cell Proteomics 2(7) 453-462 (2003).
King et al., "How proteolysis drives the cell cycle", Science 274(5293) 1652-1659 (1996).
Kudlow et al., "Post-translational modification by O—GIcNAc: another way to change protein function", J Cell Biochem 98(5) 1062-1075 (2006).
Lam et al., "Inhibition of the ubiquitin-proteasome system in Alzheimer's disease", Proc Natl Acad Sci USA 97(18) 9902-9906 (2000).
Law, "Immunoassy: A Practical Guide", Taylor and Francis Publishing (2005).
Lee et al., "Sumoylation of Smad4, the common Smad mediator of transforming growth factor-beta family signaling", J Biol Chem 278(30) 27853-27863 (2003).
Li et al., "Aging and dietary restriction effects on ubiquitination, sumoylation, and the proteasome in the heart", Mech Ageing Dev 129(9) 515-521 (2008).
Li et al., "RLE-1, an E3 ubiquitin ligase, regulates C. elegans aging by catalyzing DAF-16 polyubiquitination", Dev Cell 12(2) 235-246 (2007).
Li et al., "Sumo wrestling with type 1 diabetes", J Mol Med (Berl) 83(7) 504-513 (2005).
Lim et al., "Parkin-mediated lysine 63-linked polyubiquitination: a link to protein inclusions formation in Parkinson's and other conformational diseases?", Neurobiol Aging 27(4) 523-529 (2006).
Loda et al., "Increased proteasome-dependent degradation of the cyclin-dependent kinase inhibitor p27 in aggressive colorectal carcinomas", Nat Med 3(2) 231-234 (1997).
Matei, "Plasma proteins glycosylation and its alteration in disease", Rom J Intern Med 35(1-4) 3-11 (1997).
Meetei et al., "A novel ubiquitin ligase is deficient in Fanconi anemia", Nat Genet 35(2) 165-170 (2003).
Mo et al., "A role for Ubc9 in tumorigenesis", Oncogene 24(16) 2677-2683 (2005).
Mori et al., "Accumulation of NEDD8 in neuronal and glial inclusions of neurodegenerative disorders", Neuropathol Appl Neurobiol 31(1) 53-61 (2005).
O'Connor et al., "pp60c-src in human melanocytes and melanoma cells exhibits elevated specific activity and reduced tyrosine 530 phosphorylation compared to human fibroblast pp60c-src", Cell Growth Differ 3(7) 435-42 (1992).
Oh et al., "Chip-based analysis of SUMO (small ubiquitin-like modifier) conjugation to a target protein", Biosens Bloelectron 22(7) 1260-1267 (2007).
Olzmann et al., "Parkin-mediated K63-linked polyubiquitination: a signal for targeting misfolded proteins to the aggresome-autophagy pathway", Authopagy 4(1) 85-87 (2008).
Orii et al., "Altered post-translational modification of redox factor 1 protein in human uterine smooth muscle tumors", J Clin Endocrinol Metab 87(8) 3754-3759 (2002).
Perkins, "Post-translational modifications regulating the activity and function of the nuclear factor kappa B pathway", Oncogene 25(51) 6717-6730 (2006).
Ueda 2002 BBRC 293:307-313 (Year:2002).*
Law 1996 Immunoassay Guide, publishers Taylor&Francis (Year: 1996).*
Abel et al., "Epigenetic targets of HDAC inhibition in neurodegenerative and psychiatric disorders," Curr Opin Pharmacol 8:57-64 (2008).
Adhikary et al., "The ubiquitin ligase HectH9 regulates transcriptional activation by Myc and is essential for tumor cell proliferation," Cell 123:409-421 (2005).
Akimoto et al., "O—GIcNAc modification of nucleocytoplasmic proteins and diabetes," Med Mol Morphol 38:84-91 ( 2005).
Ayad et al., "Identification of ubiquitin ligase substrates by in vitro expression cloning," Methods Enzymol 399, 404 (2005).
Blough et al., "Glycosylation inhibitors block the expression of LAV/HTLV-III (HIV) glycoproteins," Biochem Biophys Res Commun 141:33-38 (1986).
Braunstein et al., "Inhibitory factors associated with anaphase-promoting complex/cylosome in mitotic checkpoint," Proc Natl Acad Sci U S A 104:4870-4875 (2007).
Brooks et al., "Ubiquitination, phosphorylation and acetylation: the molecular basis for p53 regulation," Curr Opin Cell Biol 15:164-171 (2003).
Casalino et al., "Accumulation of Fra-1 in ras-transformed cells depends on both transcriptional autoregulation and MEK-dependent posttranslational stabilization," Mol Cell Biol 23:4401-4415 ( 2003).
Choudhury et al., "Ubiquitination and proteasomal degradation of the BRCA1 tumor suppressor is regulated during cell cycle progression," J Biol Chem 279:33909-33918 (2004).
Ciechanover et al., "The ubiquitin proteasome system in neurodegenerative diseases: sometimes the chicken, sometimes the egg," Neuron 40:427-446 (2003).
Ciechanover et al., "Ubiquitin dependence of selective protein degradation demonstrated in the mammalian cell cycle mutant ts85," Cell 37:57-66 (1984).
Conrad et al., "Immunogenicity and conformational properties of an N-linked glycosylated peptide epitope of human T-lymphotropic virus type 1 (HTLV-I)," Biomed Pept Proteins Nucleic Acids 1:83-92 (1995).
Dery et al., "Twists and turns in the function of DNA damage signaling and repair proteins by PTMs. DNA Repair," (Amst) 6:561-577 ( 2007).
Dias et al., "O—GIcNAc modification in diabetes and Alzheimer's disease," Mol Biosyst 3:766-772 ( 2007).
Doyle et al., "Posttranslational protein modifications: new flavors in the menu of autoantigens," Curr Opin Rheumatol 14:244-249 (2002).
Doyle et al., "Posttranslational modifications of self-antigens," Ann N Y Acad Sci 1050:1-9 (2005).

(56) References Cited

OTHER PUBLICATIONS

Evans et al., "Cyclin: a protein specified by maternal mRNA in sea urchin eggs that is destroyed at each cleavage division," Cell 33:389-396 (1983).
Fang et al., "Control of mitotic transitions by the anaphase-promoting complex," Philos Trans R Soc Lond B Biol Sci 354:1583-1590 (1999).
Fujioka et al., "Inhibition of constitutive NF-kappa B activity by I kappa B alpha M suppresses tumorigenesis," Oncogene 22:1365-1370 (2003).
Gaczynska et al., "Caretaker or undertaker? The role of the proteasome in aging," Mech Ageing Dev 122:235-254 ( 2001).
Glotzer et al., "Cyclin is degraded by the ubiquitin pathway," Nature 349:132-138 (1991).
Grillari et al., "Aging and the ubiquitinome: traditional and non-traditional functions of ubiquitin in aging cells and tissues," Exp Gerontol 41:1067-1079 (2006).
Haraguchi et al., "Asparagine-linked glycosylation of the scrapie and cellular prion proteins," Arch Biochem Biophys 274:1-13 (1989).
Harauz et al., "A tale of two citrullines—structural and functional aspects of myelin basic protein deimination in health and disease," Neurochem Res 32:137-158 (2007).
Jones, "A bittersweet modification: O—GIcNAc and cardiac dysfunction,". Circ Res 96:925-926 (2005).
Kalb et al., "Fanconi anemia: causes and consequences of genetic instability," Genome Dyn 1:218-242 (2006).
Kim et al., "Multiple sclerosis: an important role for PTMs of myelin basic protein in pathogenesis," Mol Cell Proteomics 2:453-462 (2003).
King et al., "How proteolysis drives the cell cycle," Science 274:1652-1659 (1996).
Kudlow et al., "PTM by O—GIcNAc: another way to change protein function," J Cell Biochem 98:1062-1075 ( 2006).
Lam et al., "Inhibition of the ubiquitin-proteasome system in Alzheimer's disease," Proc Natl Acad Sci U S A 97:9902-9906 (2000).
Lee et al., "Sumoylation of Smad4, the common Smad mediator of transforming growth factor-beta family signaling," J Biol Chem 278:27853-27863 (2003).
Lee et al., "Post-translational glycosylation of target proteins implicate molecular mimicry in the pathogenesis of HTLV-1 associated neurological disease," J Neuroimmunol. (2008).
Li et al., "Aging and dietary restriction effects on ubiquitination, sumoylation, and the proteasome in the heart," Mech Ageing Dev 129:515-521 ( 2008).
Li et al., "SUMO wrestling with type 1 diabetes," J Mol Med 83:504-513 ( 2005).
Li et al., "RLE-1, an E3 ubiquitin ligase, regulates C. elegans aging by catalyzing DAF-16 polyubiquitination," Dev Cell 12:235-246 (2007).
Lim et al., "Parkin-mediated lysine 63-linked polyubiquitination: a link to protein inclusions formation in Parkinson's and other conformational diseases?," Neurobiol Aging 27:524-529 (2006).
Matei, "Plasma proteins glycosylation and its alteration in disease," Rom J Intern Med 35:3-11 (1997).
Meetei et al., "A novel ubiquitin ligase is deficient in Fanconi anemia," Nat Genet 35:165-170 (2003).
Mo et al., "A role for Ubc9 in tumorigenesis," Oncogene 24:2677-2683 (2005).
Mori et al., "Accumulation of NEDD8 in neuronal and glial inclusions of neurodegenerative disorders," Neuropathol Appl Neurobiol 31:53-61 (2005).
O'Connor et al., "pp60c-src in human melanocytes and melanoma cells exhibits elevated specific activity and reduced tyrosine 530 phosphorylation compared to human fibroblast pp60c-src," Cell Growth Differ 3:435-442 (1992).
Oh et al., "Chip-based analysis of SUMO (small ubiquitin-like modifier) conjugation to a target protein," Biosens Bioelectron 22, 1260 (Feb. 15, 2007).
Olzmann et al., "Parkin-mediated K63-linked polyubiquitination: a signal for targeting misfolded proteins to the aggresome-autophagy pathway," Autophagy 4:85-87 (2008).
Orii et al., "Altered PTM of redox factor 1 protein in human uterine smooth muscle tumors," J Clin Endocrinol Metab 87:3754-3759 (2002).
Perkins, "PTMs regulating the activity and function of the nuclear factor kappa B pathway," Oncogene 25:6717-6730 (2006).
Ptacek et al., "Global analysis of protein phosphorylation in yeast," Nature 438, 679 (Dec. 1, 2005).
Rape et al., "The processivity of multiubiquitination by the APC determines the order of substrate degradation," Cell 124, 89 (Jan. 13, 2006).
Reddy et al., "Ubiquitination by the anaphase-promoting complex drives spindle checkpoint inactivation," Nature 446:921-925 (2007).
Reynolds et al., "Abelson murine leukemia virus transformation-defective mutants with impaired P120-associated protein kinase activity," J Virol 36:374-386 (1980).
Sadri-Vakili et al., "Mechanisms of disease: Histone modifications in Huntington's disease," Nat Clin Pract Neurol 2:330-338 (2006).
Schnack et al. "Protein array analysis of oligomerization-induced changes in alpha-synuclein protein-protein interactions points to an interference with Cdc42 effector proteins," Neuroscience Jul. 17, 2008;154(4): 1450-57 (Feb. 29, 2008).
Schneider et al., "A glycopolypeptide (gp 100) is the main antigen detected by HTLV-III antisera," Med Microbiol Immunol 174:35-42 (1985).
Shinbo et al., "Proper SUMO-1 conjugation is essential to DJ-1 to exert its full activities," Cell Death Differ 13:96-108 (2006).
Shishido et al., "Effects of MEK5/ERK5 association on small ubiquitin-related modification of ERK5: implications for diabetic ventricular dysfunction after myocardial infarction," Circ Res 102:1416-1425 ( 2008).
Steffan et al., "SUMO modification of Huntingtin and Huntington's disease pathology," Science 304:100-104. (2004).
Sufan et al., "The role of von Hippel-Lindau tumor suppressor protein and hypoxia in renal clear cell carcinoma," Am J Physiol Renal Physiol 287:F1-6 (2004).
Takahashi-Fujigasaki et al., "SUMOylation substrates in neuronal intranuclear inclusion disease," Neuropathol Appl Neurobiol 32:92-100 (2006).
Tan et al., "Lysine 63-linked ubiquitination promotes the formation and autophagic clearance of protein inclusions associated with neurodegenerative diseases," Hum Mol Genet 17:431-439 (2008).
Turenne et al., "Glycogen synthase kinase3 beta phosphorylates serine 33 of p53 and activates p53's transcriptional activity," BMC Cell Biol 2:12 (2001).
Ueda et al., "Enhanced SUMOylation in polyglutamine diseases," Biochem Biophys Res Commun 293:307-313 (2002).
Van Boekel et al., "Modifications of arginines and their role in autoimmunity," Autoimmun Rev 2:57-62 (2003).
Wada et al., "The von Hippel-Lindau tumor suppressor gene product promotes, but is not essential for, NEDD8 conjugation to cullin-2," J Biol Chem 274:36025-36029 (1999).
Wang et al., "Glycosylation of microtubule-associated protein tau: an abnormal posttranslational modification in Alzheimer's disease," Nat Med 2:871-875 (1996).
Yao et al., "Nitrosative stress linked to sporadic Parkinson's disease: S-nitrosylation of parkin regulates its E3 ubiquitin ligase activity," Proc Natl Acad Sci U S A 101:10810-10814 (2004).
Zhang et al., "Effects of aging and dietary restriction on ubiquitination, sumoylation, and the proteasome in the spleen," FEBS Lett 581:5543-5547 (2007).
Zhong et al., "DJ-1 transcriptionally up-regulates the human tyrosine hydroxylase by inhibiting the sumoylation of pyrimidine tract-binding protein-associated splicing factor," J Biol Chem 281:20940-20948 (2006).
Zhou et al., "Autoantigenic posttranslational modifications of proteins: does it apply to rheumatoid arthritis?" Curr Opin Rheumatol 14:250-253 ( 2002).
Law Immunoassay , A pratice guide. Pub Taylor and Francis (2005).

(56) References Cited

OTHER PUBLICATIONS

Gupta et al., Molecular Systems Biology, 3:116 (2007). "Ubiquitination screen using protein microassays for comprehensive identification of Rsp5 substrates in yeast."
Hilhorst et al., Gene Regulation: Methods and Protocols, Methods in Molecular Biology, vol. 977 (2013). "Peptide microarrays for profiling of serine/threonine kinase activity of recombinant kinases and lysates of cells and tissue samples."
Gujral et al., Oncogene, 32(29): 3470-3476 (2013). "Profiling prohspho-signaling networks in breast cancer using reverse phase protein arrays."
Loda et al., "Increased proteasome-dependent degradation of the cyclin-dependent kinase inhibitor p27 in aggressive colorectal carcinomas", Nature Med. 3:231-234 (1997).
Harbers et al., "Provirus integration into a gene encoding a ubiquitin-conjugating enzyme results in a placental defect and embryonic lethality", PNAS 93(22): 12412-12417 (1996).

* cited by examiner

| Modifi-cation | E1 | E2 |
|---|---|---|
| | E1 | E2 |
| ISG15 | UBE1L | UBCH8 |
| FUB1 | NA | NA |
| Nedd8 | APPBP1-U | UBC12 |
| Fat10 | UBA6/UBE | USE1 |
| sumo1 | SEA1/2 | ubc9 |
| sumo2 | SEA1/2 | ubc9 |
| sumo3 | SEA1/2 | ubc9 |
| Apg8 | Apg7 | Apg3 |
| Apg12 | Apg7 | Apg10 |
| Urm1 | Uba4 | NA |
| Hub1 | NA | NA |
| Ufm1 | Uba5 | Ufc1 |

| Gene Ontology term | #1: predicted list<br>#2: background list | percentage in#1<br>percentage in#2 | relative % | pval |
|---|---|---|---|---|
| muscle contraction (GO:0006936) | #1: NM_000723<br>#2: BC037311 NM_... | 4.17%<br>0.89% | 82.44% 17.56% | 1.96e-1 |
| response to stress (GO:0006950) | #1: NM_003146 NM...<br>#2: BC056409 NM_... | 8.33%<br>8.64% | 49.11% 50.89% | 1 |
| cell morphogenesis (GO:0000902) | #1: NM_002291<br>#2: BC032449 NM_... | 4.17%<br>3.15% | 56.91% 43.09% | 5.383-1 |
| regulation of action potential (GO:0001508) | #1: BC014649 NM...<br>#2: BC014649 NM_... | 8.7%<br>0.35% | 96.08% 3.92% | 3.66e-3 |
| ensheathment of neurons (GO:0007272) | #1: BC014649 NM...<br>#2: NM 000533 BC | 11.76%<br>0.31% | 97.42% 2.58% | 1.67e-3 |
| microtubule cytoskeleton organization and biogenesis (GO:0000226) | #1: NM_031845<br>#2: NM_153477 BC.. | 5.88%<br>1.25% | 82.52% 17.48% | 1.96e-1 |

*FIG. 11*

DIAGNOSTIC METHOD BASED ON LARGE SCALE IDENTIFICATION OF POST-TRANSLATIONAL MODIFICATION OF PROTEINS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a continuation application under 35 U.S.C. § 120 of U.S. Ser. No. 12/696,866 filed on Jan. 29, 2010, which is a continuation-in-part application under 35 U.S.C. § 120 of an International Application PCT/US09/005670, filed Oct. 19, 2009, which claims benefit under 35 U.S.C. § 119(e) of U.S. Provisional Patent Application Ser. No. 61/196,461, filed Oct. 17, 2008, the contents of which are hereby incorporated by reference in their entireties.

GOVERNMENT SUPPORT

This invention was made with government support under grant No. GM039023 awarded by The National Institutes of Health. The government has certain rights in the invention.

SEQUENCE LISTING

The instant application contains a Sequence Listing which has been submitted via [EFS-Web] *Patent Center* and is hereby incorporated by reference in its entirety. Said [ASCII] *XML* copy, created on [Feb. 4, 2010] *Sep. 26, 2023*, is named [28060668.txt] *002806-066834USRE_SL.xml*, and is [1,222] *2,876* bytes in size.

*This is an application for reissue of U.S. Pat. No. 11,333,668.*

BACKGROUND OF THE INVENTION

Post-translational modification (PTM) of proteins has been studied largely using purified systems or whole cells. The analysis of protein PTM in cell extracts as well as extracellular fluids is both theoretically and empirically problematic. For example, both ubiquitination and phosphorylation, common examples of PTM, are very rapidly reversed, and this reversal requires no energy input or special conditions, aside from the actions of isopeptidases and phosphatases. Moreover, classical biochemical methods such as Western blot do not work well for concentrated mixtures of proteins, because the modified protein bands spread throughout the electrophoretic gel, and in complex samples, such as a cell extract or a blood plasma sample, many protein species would overlap, making protein identification difficult or impossible. Specifically, genome-wide methods for detecting PTM alterations are still in their infancy and largely depend on the interactions of biochemically purified systems. Chemical methods such as mass spectrometry cannot distinguish ubiquitin and polyubiquitin chains, yet only the latter are critical for protein degradation. A further limitation of such classical biochemical methods is that cryopreserved specimens which can be more readily available or are more logistically easy to procure cannot be used for most of these analyses and may have altered representation of the physiological condition. Furthermore, MS methods do not analyze the activity/function of a specific tissue/sample and its content but rather identifies the abundance of certain proteins in it. Thus, the complexity of the tissue and the dynamic range of different protein level are often limiting their detection.

In recent years, our understanding of posttranslational modifications and their implication for human diseases have greatly increased. In Alzheimer's disease (25) and Parkinson's disease (26-28) the ubiquitination of proteins has been shown to play a pivotal role in the regulation of cellular processes and human pathologies. Although the role that ubiquitination plays in tumorigenesis is still poorly understood, cases of ubiquitin ligases showing relationships with oncogenesis were recently described (29-31). Thus, systematic assays for the screening, including diagnostic screening, of ubiquitinated or other post-translationally modified proteins remain limited.

BRIEF SUMMARY OF THE INVENTION

The invention provides methods and kits for the systematic and large scale determination of protein PTMs and the enzyme activities that catalyze them. The methods entail incubating protein microarrays or another protein array format with cell extracts or fluids from a subject, performing specific PTM reactions on the microarrays, and detecting protein modification states of specific proteins. The methods according to the invention overcome obstacles associated with classical biochemical techniques by performing PTM reactions on protein microarrays with biological samples, such as patient materials, whose physiological state is preserved, appropriately supplemented, if so desired, with limiting PTM reaction components, and make it possible for the first time to rapidly screen patient samples for activities that modulate PTM states related to disease, and to rapidly screen for test agents that modulate PTM or PTM alteration pathways.

Accordingly, in one aspect, described herein is a method of identifying at least one post-translational modification (PTM) or PTM alteration on at least one protein, the method comprising the steps of:

(a) contacting a functional cell extract with a solid state array, the array comprising an ordered plurality of proteins under conditions that allow PTM to occur or that allow PTM to be modified;

(b) establishing at least one PTM reaction or PTM alteration reaction thereof on the array, whereby the reaction results in at least one PTM or PTM alteration of at least one protein on the array through the activity of one or more enzymes present in the cell extract; and (c) detecting the at least one PTM or PTM alteration by detecting a signal from the array thereby identifying the PTM or PTM alteration on the at least one protein.

In one embodiment of this aspect, the method further comprises identifying the effect of a test agent on the PTM or PTM alteration comprising the additional steps of:

(a) contacting the functional cell extract with a test agent;

(b) establishing at least one PTM reaction or PTM alteration on the array in the presence of the test agent, whereby the PTM reaction results in at least one PTM or PTM alteration of at least one protein on the array through the activity of one or more enzymes present in the cell extract; and (c) detecting the at least one PTM or PTM alteration and comparing the PTM reaction or PTM alteration reaction with a parallel reaction where a control agent has been added thereby allowing for detection of an effect of the test agent on at least one PTM or PTM alteration.

In one embodiment of this aspect, an increase in the signal from the array compared to a background or the reaction with a control is indicative of increased PTM. In another embodiment of this aspect, a decrease in the signal from the array compared to a background or the reaction with a control is indicative of PTM alteration.

In one embodiment of this aspect, the detecting is performed using an antibody or antigen-binding fragment thereof, a natural or recombinant ligand, a small molecule, a modifying moiety, or a biochemical analysis capable of detecting the PTM or PTM alteration. In some embodiments, the antibody or antigen-binding fragment thereof, the natural or recombinant ligand, the small molecule, or the modifying moiety is labeled with a tag. In some such embodiments, the tag is a fluorescent molecule, a radioisotope, a nucleotide chromophore, an enzyme, a substrate, a chemiluminescent moiety, magnetic particle, bioluminescent moiety, or peptide. In some embodiments, the biochemical analysis is performed using mass spectroscopy, peptide mapping, or amino acid sequencing.

In one embodiment of this aspect, the functional cell extract is not diluted prior to the contacting with the solid state array. In one embodiment of this aspect, the functional cell extract is concentrated prior to the contacting with the solid state array.

In another embodiment of this aspect, the functional cell extract is obtained from a frozen or cryopreserved sample.

In another embodiment of this aspect, an additional cellular energy source in the form of ATP is provided to the functional cell extract.

In another embodiment of this aspect, the array comprising a plurality of proteins, comprises at least one protein, protein fragment or peptide attached to the array without an added tag.

In another embodiment of this aspect, the array comprising a plurality of proteins comprises at least one protein, protein fragment or peptide attached to the array with a C-terminal or N-terminal tag.

In another embodiment of this aspect, the functional cell extract is derived from a specified cellular compartment. In one embodiment, the cellular compartment is nucleus. In one embodiment, the cellular compartment is cytosol. In one embodiment, the cellular compartment is mitochondria.

In another embodiment of this aspect, the functional cell extract is derived from a biological sample. In one embodiment, the biological sample is selected from the group consisting of saliva, whole blood, serum, plasma, urine, cerebrospinal fluid, peritoneal fluid, chorionic villus, placenta, solid tissue, amniotic fluid, a cell sample, and a tissue culture sample.

In one embodiment of this aspect, the PTM is selected from the group consisting of ubiquitination, phosphorylation, glycosylation, sumoylation, acetylation, S-nitrosylation or nitrosylation, citrullination or deimination, neddylation, OClcNAc, ADP-ribosylation, methylation, hydroxylation, fattenylation, ufmylation, prenylation, myristoylation, S-palmitoylation, tyrosine sulfation, formylation, carboxylation, and any combination thereof.

In one embodiment of this aspect, the PTM alteration is selected from the group consisting of deubiquitination (DUB), dephosphorylation, deglycosylation, desumoylation, deacetylation, de-S-nitrosylation or denitrosylation, decitrullination or dedeimination, deneddylation, removal of OClcNAc, de-ADP-ribosylation, demethylation, de-hydroxylation, defattenylation, deufmylation, and any combination thereof.

In another embodiment of this aspect, the solid state array is selected from the group consisting of protein arrays on microchips, ELISA plates with immobilized proteins attached on the plates, protein-coated beads, and microfluidic chips coated with desired proteins.

In another embodiment of this aspect, 2-10 PTM or PTM alterations thereof are identified simultaneously.

In one embodiment of this aspect, and all such aspects described herein, the invention utilizes protein microarrays or other array formats of proteins together with appropriately supplemented functional cell extracts or body fluid samples to study the role of PTM in the presence and progression of many types of disease and many aspects of cellular function. Certain PTM states are mechanistically involved in cellular protein turnover, and consequently PTM states can be correlated with diseases related to protein turnover, such as, for example, Alzheimer's disease and other neurodegenerative diseases, and diseases related to regulation of the cell cycle, such as cancer.

In one aspect, the invention provides a method of identifying an altered PTM state of a protein in a patient. The method includes contacting a functional extract of a sample from the patient with a microarray containing an ordered plurality of proteins that represent proteins in the patient, establishing conditions for a specific PTM reaction in the extract, and determining the level of PTM of one or more proteins in the microarray. The presence or absence, or the observed level, of PTM of proteins in the microarray is then compared with the level of PTM of the corresponding proteins in a control sample, so that altered PTM states of proteins are identified that are expected to be similarly altered in the patient.

Another aspect of the invention is a method of identifying a protein PTM enzyme activity in a patient. The method includes contacting a functional extract of a sample from the patient with an array comprising an ordered plurality of proteins that represent proteins in the patient, and identifying post-translationally modified proteins in the array. The presence or absence, or the relative amount, of a PTM enzyme activity in the patient can be inferred from the protein posttranslational modifications observed in the array. The presence or absence, or the relative amount, of a corresponding PTM state produced by the enzyme activity in the patient may also be inferred from the results obtained with this method.

Still another aspect of the invention is a method of diagnosing a disease or medical condition in a patient. The method includes contacting a functional extract of a sample from the patient with a microarray containing an ordered plurality of proteins that represent proteins in the patient and identifying post-translationally modified proteins in the microarray to obtain a PTM state data set. The data set can serve as a signature or profile of protein PTMs in the patient as well as of the enzymes producing them. The data set is then compared with a standard data set that includes PTM state data diagnostic for the disease or medical condition and, based on the comparison, the disease or medical condition is diagnosed in the patient.

Yet another aspect of the invention is a method of identifying a set of biomarkers for a disease or medical condition. The method includes comparing the PTM profile of one or more patients having the disease or medical condition with similar profiles from one or more control subjects who do not have the disease or medical condition.

The profiles are obtained by separately contacting functional extracts from the patients and control subjects with an array containing an ordered plurality of proteins, such as proteins encoded by the human genome, and determining the level of PTM of one or more proteins in the array. The presence or absence, or the observed level, of PTM of proteins in the array for the patients is then compared with the presence or absence or level of PTM of the corresponding proteins for the control subjects. A set of biomarkers is formed from proteins of the patients whose level of PTM is altered compared to control levels.

In a further aspect, the invention provides a kit for the diagnosis of a disease or medical condition, or the characterization of the effects of a drug, by the analysis of a PTM state of a protein in a patient sample. The kit includes a standard containing one or more functional extracts capable of producing a known pattern of protein PTM states on a protein microarray or in another array format. The kit also is adapted for, and contains instructions for, carrying out one of the above described methods. Optionally, the kit further contains a protein microarray, or a reagent such as a substrate, an enzyme, an enzyme inhibitor, a drug, or one or more antibodies. When applied with a method according to the invention, the standard produces a pattern of protein PTM that is diagnostic for a disease or medical condition, or the effects of a drug.

BRIEF DESCRIPTION OF THE DRAWINGS

Other features and advantages of the invention will be apparent from the following description of the preferred embodiments thereof and from the claims, taken in conjunction with the accompanying drawings.

FIG. 10A shows the results for a CP-released extract, and FIG. 10B shows the results for an APC-inhibited extract.

FIG. 11 shows human proteins that were significantly ubiquitinated by enzymes present in cerebrospinal fluid (CSF) from a patient with brain tumor.

DETAILED DESCRIPTION OF THE INVENTION

Figure 1A:
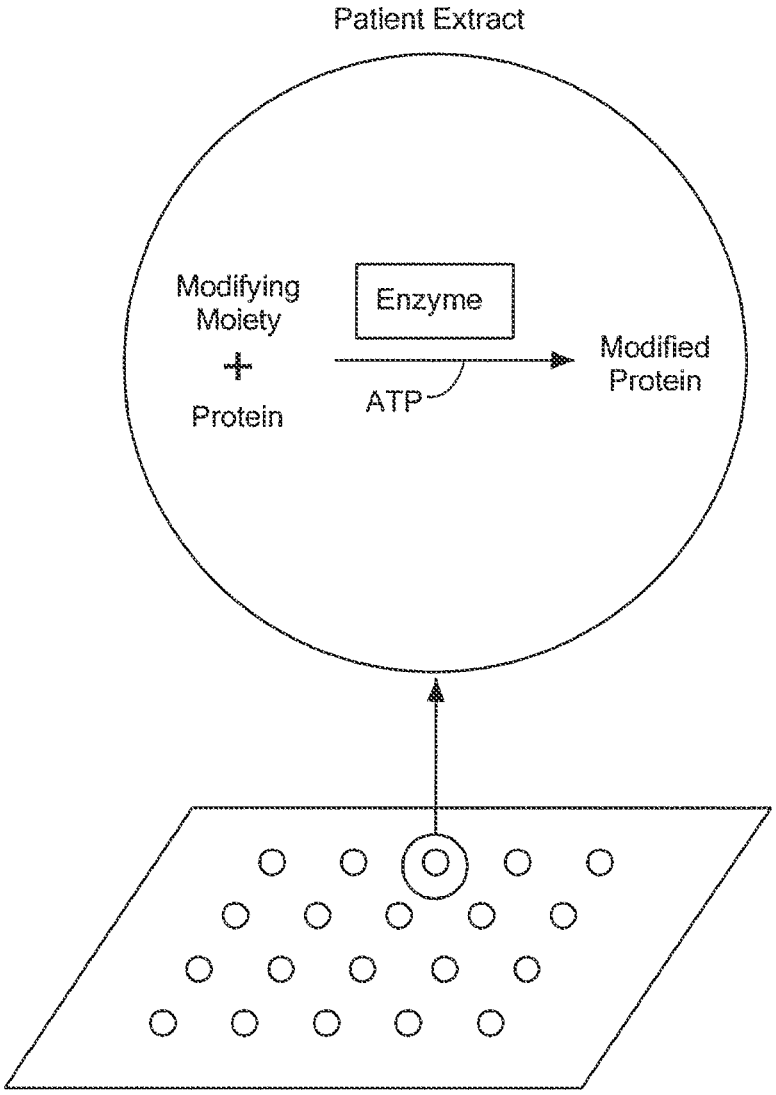
FIG. 1A presents a schematic illustration of a PTM reaction carried out on a protein microarray using a functional extract from a patient sample.
Figure 1B:
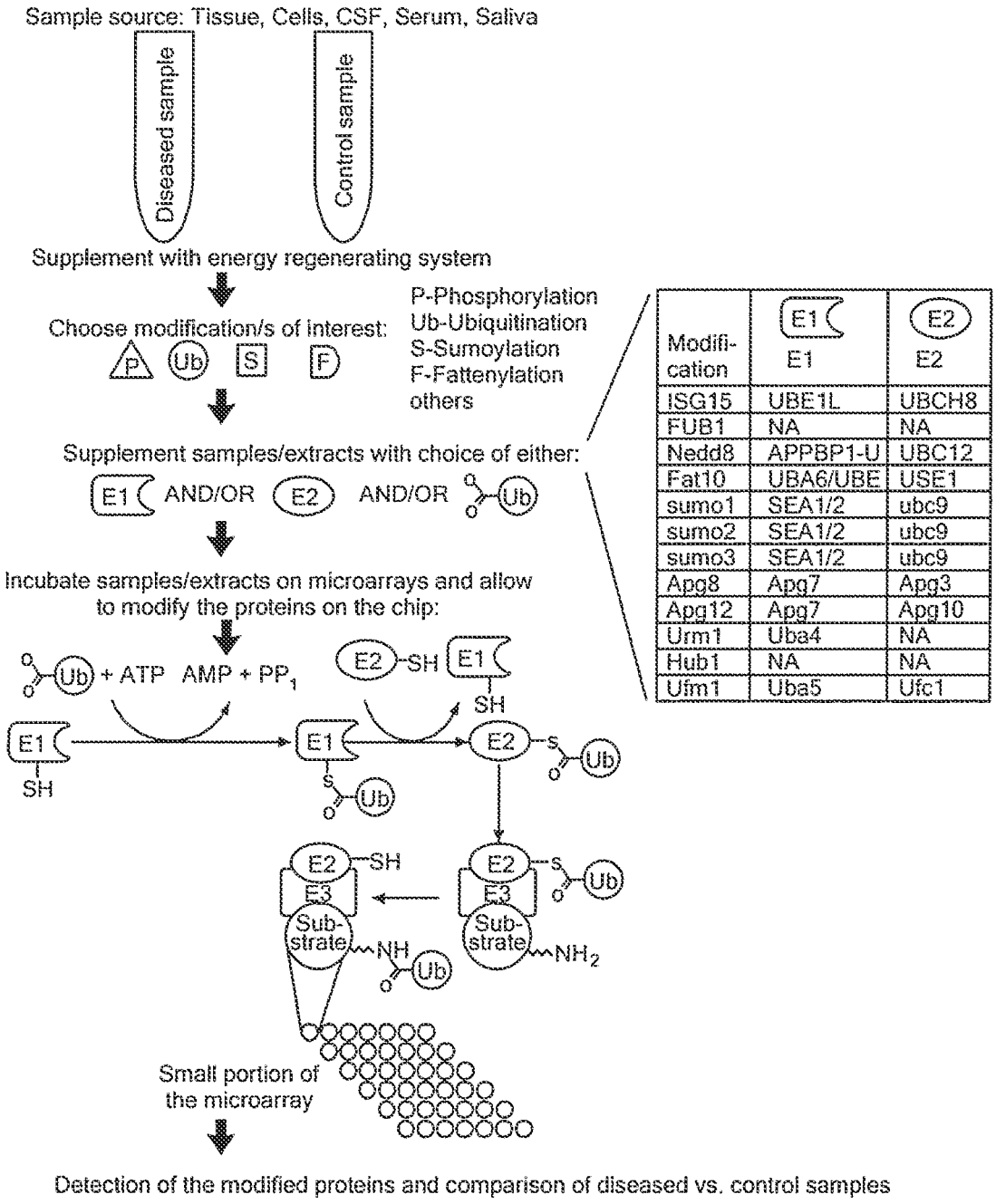
FIG. 1B shows a schematic illustration of the use of a PTM reaction on a protein microarray to diagnose a disease in a patient sample. The inset shows a reaction scheme common to ubiquitin-like modifiers, and the inset at the right shows example E1 and E2 enzymes for several ubiquitin-like modifiers.

The inventors have developed methods that permit the rapid and large-scale diagnostic screening of altered protein PTM and PTM alteration states and related enzyme activities correlated with disease. The methods involve, in part, applying concentrated cell extracts or biological fluid samples from a subject to protein microarrays and appropriately supplementing them to carry out one or more specific PTM or PTM alteration reactions. Specifically, one or more PTM or PTM alterations are then detected by labeling the modified proteins and scanning the array.

Patterns of post-translational changes in certain polypeptides are known to correlate with certain diseases, such as Alzheimer's disease and cancer (see, for example, Table 3). While the altered polypeptides themselves may be detectable in extracellular fluids or cell extracts, and could be useful in diagnosing disease and monitoring its progression, an easier alternative to looking for the modified proteins themselves is to assay for the activity of specialized enzymes that make the modifications and are present in such fluids or extracts. Such assays are the focus, in part, of this invention. Assaying for such activities requires, in addition to the enzyme itself or enzymes themselves, which is/are supplied by the biological sample, such as a patient sample, the presence of one relevant cofactors and appropriate substrates. A PTM or PTM alteration activity assay can, for example, be used not only to diagnose a disease state, it can also be used to identify candidate biomarkers of diseases in biological fluid samples and cell extracts prepared from patient samples, and to test the effects of test agents on PTM or PTM alteration pathways, for applications such as drug design and discovery. Knowledge of the modified target proteins in a disease provides intrinsically important information about the altered post-translational process that occurs in the disease and its role in the disease.

Covalently modified proteins, such as polyubiquitinated, ubiquitinated, phosphorylated, glycosylated, sumoylated, acetylated, S-nitrosylated or nitrosylated, citrullinated or deiminated, neddylated, OClcNAc-added, ADP-ribosylated, methylated, hydroxymethylated, fattenylated, ufmylated, prenylated, myristoylated, S-palmitoylated, tyrosine sulfated, formylated, and carboxylated proteins are hard to identify by the standard biochemical technique of gel electrophoresis, because the modified protein bands spread throughout the gel. Identifying the converse alteration of a PTM, such as, for example, deubiquitination (DUB), dephosphorylation, deglycosylation, desumoylation, deacetylation, deS-nitrosylation or denitrosylation, decitrullination or dedeimination, deneddylation, removal of OClcNAc, de-ADP-ribosylation, demethylation, de-hydroxylation, defattenylation, deufmylation, deprenylation, demyristoylation, de-S-palmitoylation, tyrosine desulfation, deformylation, decarboxylation, and deamidation is similarly difficult to detect using such standard biochemical methods. In a complex sample like a functional cell extract or biological sample, such as an undiluted or concentrated body fluid, many protein molecular species would overlap, making identification of specific modified proteins difficult or impossible. The high concentration and large number of different proteins in patient samples such as cell or tissue extracts, and body fluids such as blood plasma or CSF, generally require additional processing steps to separate the sample into different fractions or to purify certain molecular components prior to analysis. In contrast, with the present methods described herein, a PTM or PTM alteration reaction is performed directly on a solid state array, such as a protein microarray, or any other array format wherein the location of each protein is known. The known physical location of the protein on the array, rather than its electrophoretic mobility in a gel, is used to identify the target. Combined with the use of antibodies that have binding specificity for particular PTM or PTM alteration states, such as polyubiquitinated vs. monoubiquitinated proteins, or combined with the use of any labeled modifying moiety, the use of protein arrays greatly simplifies the problem of identifying specific PTM or PTM alteration states on specific proteins, and the use of multiplex formats, such as microarrays, also makes possible the simultaneous analysis of thousands of proteins. Thus, the present invention overcomes previous obstacles to identifying altered PTM or PTM alteration states and altered activity of enzymes that produce PTM or PTM alteration in a patient and brings PTM and PTM alteration analysis into a realm where it is possible for the first time to diagnose disease in a clinical setting.

Accordingly, in one aspect, described herein is a method of identifying at least one post-translational modification (PTM) or PTM alteration on at least one protein, the method comprising the steps of:

(a) contacting a functional cell extract with a solid state array, the array comprising an ordered plurality of proteins under conditions that allow PTM to occur or that allow PTM to be modified;

(b) establishing at least one PTM reaction or PTM alteration reaction thereof on the array, whereby the reaction results in at least one PTM or PTM alteration of at least one protein on the array through the activity of one or more enzymes present in the cell extract; and (c) detecting the at least one PTM or PTM alteration by detecting a signal from the array thereby identifying the PTM or PTM alteration on the at least one protein.

In one embodiment of this aspect, the method further comprises identifying the effect of a test agent on the PTM or PTM alteration comprising the additional steps of:

(a) contacting the functional cell extract with a test agent;

(b) establishing at least one PTM reaction or PTM alteration on the array in the presence of the test agent, whereby the PTM reaction results in at least one PTM or PTM alteration of at least one protein on the array through the activity of one or more enzymes present in the cell extract; and (c) detecting the at least one PTM or PTM alteration and comparing the PTM reaction or PTM alteration reaction with a parallel reaction where a control agent has been added thereby allowing for detection of an effect of the test agent on at least one PTM or PTM alteration.

As used herein, an "agent" for use in the methods described herein refers to any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecules having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In such embodiments, the effects of one or more test agents that modify specific PTM or PTM alteration pathways can be determined using the methods described herein. The ability to rapidly screen one or more test agents for effects on a multitude of specific PTM or PTM alteration reactions simultaneously is useful for drug design and discovery purposes. As defined herein, a test agent that modifies or modulates a specific PTM or PTM alteration pathway is one that causes a detectable change in a PTM or PTM alteration reaction mediated by a functional cell extract, such as, changing the kinetics of the reaction (increase or decrease) or preventing the reaction from occurring entirely. In some embodiments, the test agent can replace a missing component of the functional cell extract, such that a PTM or PTM alteration reaction occurs, which did not occur in the absence of the test agent. In such embodiments, the test agent acts to replace or modulate a component of the PTM or PTM alteration pathway. The ability to rapidly and simultaneously screen for the effects of a test agents on PTM or PTM alteration pathway is useful for high-throughput applications, such as screening of compounds for drug discovery applications.

In another embodiment, the methods described herein comprise detecting the PTM or PTM alteration using one or more agents capable of specifically detecting the PTM or PTM alteration. Agents specific for detecting the PTM or PTM alteration include, but are not limited to, antibodies or antigen-binding fragments thereof, natural or recombinant ligands, small molecules; nucleic acid sequence and nucleic acid analogues; intrabodies; aptamers; and other proteins or peptides; and a modifying moiety. In some embodiments, the detecting comprises the use of one or more antibodies which are directly labeled with a tag. In other embodiments, the detecting comprises the use of one or more antibodies than can be detected using a secondary antibody. In some embodiments, the secondary antibody is directly labeled with a tag. In other embodiments, the secondary antibody is detected using a tertiary antibody directly labeled with a tag. In other embodiments, one or more biochemical methods can be used for detecting PTM or PTM alterations. In such embodiments, the biochemical methods can include, but are not limited to, mass spectroscopy, peptide mapping, and amino acid sequencing.

In some embodiments of this aspect and all aspects described herein, the preferred agents specific for detecting the PTM or PTM alteration are antibody agents that specifically bind the PTM or PTM alteration, and can include polyclonal and monoclonal antibodies, and antigen-binding derivatives or fragments thereof. Well-known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art. Accordingly, as used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments may be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings [Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford)]. Such antibodies or antigen-binding fragments specific for CD31, CD105, CD105, CD44, and Sca-1 are available commercially from vendors such as R&D Systems, BD Biosciences, e-Biosciences and Miltenyi, or can be raised against these modifications by methods known to those skilled in the art.

In some embodiments of the aspects described herein, an agent specific for a PTM or PTM alteration, such as an antibody or antigen-binding fragment thereof, a natural or recombinant ligand, a small molecule, or a modifying moiety, is directly labeled with a tag to facilitate the detection of the modification. The terms "label" or "tag", as used herein, refer to a composition capable of producing a detectable signal indicative of the presence of a target, such as, the presence of a specific modification in a biological sample. Suitable labels include fluorescent molecules, radioisotopes, nucleotide chromophores, enzymes, substrates, chemiluminescent moieties, magnetic particles, bioluminescent moieties, peptide tags (c-Myc, HA, VSV-G, HSV, FLAG, V5 or HIS) and the like. As such, a label is any composition detectable by spectroscopic, photochemical, biochemical, immunochemical, electrical, optical or chemical means needed for the methods to identify the PTM or PTM alteration. In some embodiments of the aspects described herein, the modification moiety itself may be labeled directly. For example, one can use a radioactive label or a florescent label so that the protein modification can be read directly (or in combination with other modifications) without the use of antibodies. Naturally, also antibodies may be labeled to assist in their direct detection.

The terms "labeled antibody" or "tagged antibody", as used herein, includes antibodies that are labeled by detectable means and include, but are not limited to, antibodies that are fluorescently, enzymatically, radioactively, and chemiluminescently labeled. Antibodies can also be labeled with a detectable tag, such as c-Myc, HA, VSV-G, HSV, FLAG, V5, or HIS, which can be detected using an antibody specific to the tag, for example, an anti-c-Myc antibody. Various methods of labeling polypeptides and glycoproteins are known in the art and may be used. Non-limiting examples of fluorescent labels or tags for labeling the antibodies for use in the methods of invention include Hydroxycoumarin, Succinimidyl ester, Aminocoumarin, Succinimidyl ester, Methoxycoumarin, Succinimidyl ester, Cascade Blue, Hydrazide, Pacific Blue, Maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorphyll protein, TruRed (PerCP-Cy5.5 conjugate), FluorX, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy2, Cy3, Cy3B, Cy3.5, Cy5, Cy5.5 or Cy7.

In some embodiments of the methods described herein, a PTM comprises ubiquitination, phosphorylation, glycosylation, sumoylation, acetylation, S-nitrosylation or nitrosylation, citrullination or deimination, neddylation, deimination, OClcNAc, ADP-ribosylation, methylation, hydroxylation, fattenylation, ufmylation, prenylation, myristoylation, S-palmitoylation, tyrosine sulfation, formylation, carboxylation, and any combination thereof. In some embodiments, a PTM consists essentially of ubiquitination, phosphorylation, glycosylation, sumoylation, acetylation, S-nitrosylation or nitrosylation, citrullination or deimination, neddylation, OClcNAc, ADP-ribosylation, methylation, hydroxylation, fattenylation, ufmylation, prenylation, myristoylation, S-palmitoylation, tyrosine sulfation, formylation, carboxylation, and any combination thereof. In some embodiments, a PTM consists of ubiquitination, phosphorylation, glycosylation, sumoylation, acetylation, S-nitrosylation or nitrosylation, citrullination or deimination, neddylation, OClcNAc, ADP-ribosylation, methylation, hydroxylation, fattenylation, ufmylation, prenylation, myristoylation, S-palmitoylation, tyrosine sulfation, formylation, carboxylation, and any combination thereof.

In some embodiments of the methods described herein, a PTM alteration comprises deubiquitination (DUB), dephosphorylation, deglycosylation, desumoylation, deacetylation, de-S-nitrosylation or denitrosylation, decitrullination or dedeimination, deneddylation, removal of OClcNAc, de-ADP-ribosylation, demethylation, de-hydroxylation, defattenylation, deufinylation, deprenylation, demyristoylation, de-S-palmitoylation, tyrosine desulfation, deformylation, decarboxylation, deamidation, and any combination thereof. In some embodiments, a PTM alteration consists essentially of deubiquitination (DUB), dephosphorylation, deglycosylation, desumoylation, deacetylation, de-S-nitrosylation or denitrosylation, decitrullination or dedeimination, deneddylation, removal of OClcNAc, de-ADP-ribosylation, demethylation, de-hydroxylation, defattenylation, deufmylation, deprenylation, demyristoylation, de-S-palmitoylation, tyrosine desulfation, deformylation, decarboxylation, deamidation, and any combination thereof. In some embodiments, a PTM alteration consists of deubiquitination (DUB), dephosphorylation, deglycosylation, desumoylation, deacetylation, de-S-nitrosylation or denitrosylation, decitrullination or dedeimination, deneddylation, removal of OClcNAc, de-ADP-ribosylation, demethylation, de-hydroxylation, defattenylation, deufmylation, deprenylation, demyristoylation, de-S-palmitoylation, tyrosine desulfation, deformylation, decarboxylation, deamidation, and any combination thereof.

As used herein, the term "post-translational modification" or "PTM" refers to a reaction wherein a chemical moiety is covalently added to or non-covalently binds to protein. As used herein, the term "PTM alteration" refers to a reaction wherein a chemical moiety covalently attached to or non-covalently bound to a protein is removed or altered (maybe in chain topology, different PTM combinations, etc). "Covalent bonding," as used herein, refers to the form of chemical bonding that is characterized by the sharing of pairs of electrons between atoms, and other covalent bonds. Covalent bonding includes many kinds of interactions, including, but not limited to, $\alpha$-bonding, $\pi$-bonding, metal to non-metal bonding, agostic interactions, and three-center two-electron bonds. "Non-covalent bonding," as used herein, refers to the type of chemical bond, typically between macromolecules, that does not involve the sharing of pairs of electrons, but rather involves more dispersed variations of electromagnetic interactions. Noncovalent bonds are critical in maintaining the three-dimensional structure of large molecules, such as proteins and nucleic acids, and are involved in many biological processes in which large molecules bind specifically but transiently to one another. Examples of noncovalent interactions include, but are not limited to, ionic bonds, hydrophobic interactions, hydrogen bonds, van der Waals forces, i.e. "London dispersion forces", and Dipole-dipole bonds.

Many proteins can be post-translationally modified through the covalent addition or transient non-covalent binding of a chemical moiety (also referred to herein as a "modifying moiety") after the initial synthesis (i.e., translation) of the polypeptide chain. Such chemical moieties usually are added by an enzyme to an amino acid side chain or to the carboxyl or amino terminal end of the polypeptide chain (i.e., PTM), and may be cleaved off by another enzyme (i.e., PTM alteration). Single or multiple chemical moieties, either the same or different chemical moieties, can be added to or bound to a single protein molecule. PTM of a protein can alter its biological function, such as its enzyme activity, its binding to or activation of other proteins, or its turnover, and is important in cell signaling events, development of an organism, and disease. Examples of PTM covered by the methods of the invention described herein include, but are not limited to, ubiquitination, phosphorylation, sumoylation, neddylation, ADP-ribosylation, glycosylation, acetylation, S-nitrosylation or nitrosylation, citrullination or deimination, the addition of OClcNAc, methylation, hydroxylation, fattenylation, ufmylation, prenylation, myristoylation, S-palmitoylation, tyrosine sulfation, formylation, and carboxylation. In some embodiments, a PTM can include both a covalent addition and non-covalent binding of a chemical moiety to a protein. For example, small ubiquitin-related modifiers (SUMOs) can be both covalently conjugated to a protein, and transiently non-covalently bound to the same protein to mediate different effects. In such embodiments, the covalent conjugation and non-covalent binding require different sequence motifs.

Similarly, a PTM alteration can involve removal of a covalently conjugated or a non-covalently bound chemical moiety. Examples of PTM alteration covered by the methods of the invention described herein include, but are not limited to, deubiquitination (DUB), dephosphorylation, deglycosylation, desumoylation, deacetylation, deS-nitrosylation, denitrosylation, decitrullination or dedeimination, deneddylation, de-ADP-ribosylation, removal of OClcNAc, demethylation, de-hydroxylation, defattenylation, deufmylation, deprenylation, demyristoylation, de-S-palmitoylation, tyrosine desulfation, deformylation, decarboxylation, and deamidation.

As used herein, "ubiquitination" or "ubiquitylation" refers to the post-translational modification of a protein by the covalent attachment (via an isopeptide bond) of one or more ubiquitin monomers. The ubiquitylation cascade is started by the E1 enzyme. The amino acid sequence of human ubiquitin is:

(SEQ ID NO: 1)

MQIFVKTLTGKTITLEVEPSDTIENVKAKIQDKEGIPPDQQRLI

FAGKQLEDGRTLSDYNIQKESTLHLVLRLRGG.

As used herein, removal of one or more ubiquitin molecules is known as "deubiquitination."

As used herein, "phosphorylation" refers to the addition of a phosphate ($PO_4$) group to a protein or other organic molecule. As used herein, "dephosphorylation" refers to the removal of a phosphate group from a protein or other organic molecule.

As used herein, "sumoylation" refers to the process whereby Small Ubiquitin-like Modifier or "SUMO" proteins are covalently attached to other proteins in cells to modify their function. SUMO proteins are similar to ubiquitin, and SUMOylation is directed by an enzymatic cascade analogous to that involved in ubiquitination. As defined herein, "desumoylation" refers to the process whereby SUMO proteins are removed from proteins in cells.

As used herein, "neddylation" refers to the process by which the ubiquitin-like protein Nedd8 is conjugated to its target proteins. This process is analogous to ubiquitination, although it relies on its own E1 and E2 enzymes. As used herein, "deneddylation" refers to the process by which the ubiquitin-like protein Nedd8 is unconjugated from its target proteins.

As used herein, "ADP-ribosylation" refers to the PTM of proteins that involves the addition of one or more ADP and ribose moieties. As used herein, "de-ADP-ribosylation" refers to the removal of one or more ADP and ribose moieties.

As defined herein, "glycosylation" refers to the enzymatic process that links saccharides to produce glycans, attached to proteins, lipids, or other organic molecules. For the methods described herein, glycosylation includes N-linked glycosylation, O-linked glycosylation (O—N-acetylgalactosamine (O-GalNAc), O-fucose, O-glucose, O—N-acetylglucosamine (O-GlcNAc), O—N-acetylglucosamine, O-mannose, Collagen Glycosylation, Hydroxyproline Glycosylation, Glycosylation of Glycogenin, Glycosylation of Ceramide, Proteoglycans), phospho-Serine Glycosylation and C-mannosylation. As defined herein, "deglycosylation" refers to the enzymatic process that removes saccharides attached to proteins, lipids, or other organic molecules.

As used herein, "acetylation" (or in IUPAC nomenclature "ethanoylation") refers to the reaction that introduces an acetyl functional group into a chemical compound, and includes N-alpha-terminal acetylation and lysine acetylation. As used herein, "deacetylation" (or in IUPAC nomenclature "de-ethanoylation") refers to the reaction that removes an acetyl functional group from a chemical compound.

As defined herein, "S-nitrosylation" or "nitrosylation" refer to the addition of a nitroso group to a sulfur atom of an amino acid residue of a protein. As defined herein, "de-S-nitrosylation" or "de-nitrosylation" refer to the removal of a nitroso group from a sulfur atom of an amino acid residue of a protein.

As used herein, "citrullination" or "deimination" are the terms used for the post-translational modification of the amino acid arginine in a protein into the amino acid citrulline. As used herein, "decitrullination" or "de-deimination" are the terms used for the removal of the amino acid citrulline from a protein.

As used herein, "methylation" is the term used to denote the addition of a methyl group to a substrate or the substitution of an atom or group by a methyl group. Methylation is a form of alkylation with specifically a methyl group. Protein methylation typically takes place on arginine or lysine amino acid residues in the protein sequence. Arginine can be methylated once (monomethylated arginine) or twice, with either both methyl groups on one terminal nitrogen (asymmetric dimethylated arginine) or one on both nitrogens (symmetric dimethylated arginine) by peptidylarginine methyltransferases (PRMTs). Lysine can be methylated once, twice or three times by lysine methyltransferases. As used herein, "demethylation" refers to the removal of a methyl group from a protein.

As used herein, "hydroxylation" refers to the chemical process that introduces one or more hydroxyl groups (—OH) into a compound (or radical) thereby oxidizing it. The principal residue to be hydroxylated in proteins is proline. The hydroxylation occurs at the Cγ atom, forming hydroxyproline (Hyp). In some cases, proline may be hydroxylated instead on its Cβ atom. Lysine may also be hydroxylated on its Cδ atom, forming hydroxylysine (Hyl). As used herein, "dehydroxylation" refers to the chemical process that removes one or more hydroxyl groups (—OH) from a protein.

As used herein, "ufmylation" refers to the process whereby the ubiquitin-like modifier Ufm-1 is covalently attached to a protein. As used herein, "deufinylation" refers to the process whereby the ubiquitin-like modifier Ufm-1 is removed from a protein.

As used herein, "fattenylation" refers to the process whereby the ubiquitin-like modifier FAT10 is covalently attached to a protein. As used herein, "defattenylation" refers to the process whereby the ubiquitin-like modifier FAT10 is removed from a protein.

As used herein, the terms "prenylation," "isoprenylation," or "lipidation" refers to the addition of hydrophobic molecules to a protein. Protein prenylation involves the transfer of either a farnesyl or a geranyl-geranyl moiety to C-terminal cysteine(s) of the target protein. As used herein, the terms "deprenylation," "desoprenylation," or "delipidation" refers to the removal of hydrophobic molecules from a protein.

As used herein, "myristoylation" refers to the PTM process wherein myristoyl group (derived from myristic acid) is covalently attached via an amide bond to the alpha-amino group of an N-terminal amino acid of a polypeptide. It is more common on glycine residues but also occurs on other amino acids. Myristoylation occurs post-translationally, for example when previously internal glycine residues become exposed by caspase cleavage during apoptosis. As used herein, "demyristoylation" refers to the PTM alteration wherein myristoyl group (derived from myristic acid) is removed from the alpha-amino group of an N-terminal amino acid of a polypeptide.

As used herein, "S-palmitoylation" refers to the covalent attachment of fatty acids, such as palmitic acid, to cysteine residues of proteins. As used herein, "de-S-palmitoylation" refers to the removal of fatty acids, such as palmitic acid, to cysteine residues from proteins.

As used herein, "tyrosine sulfation" is a PTM where a sulfate group is added to a tyrosine residue of a protein molecule. As used herein, "tyrosine desulfation" is a PTM alteration where a sulfate group is removed from a tyrosine residue of a protein molecule.

As used herein, "deamidation" refers to the chemical reaction in which an amide functional group is removed from a protein. The reaction damages the amide-containing side chains of the amino acids asparagine and glutamine.

As used herein, "formylation" is a type of PTM in which a formyl group is added to the N-terminus of a protein. As used herein, "deformylation" is a type of PTM alteration in which a formyl group is removed from the N-terminus of a protein.

As used herein, "carboxylation" is a PTM in which a carboxylic acid group is added to glutamate residues in proteins. It occurs primarily in proteins involved in the blood clotting cascade, specifically factors II, VII, IX, and X, protein C, and protein S, and also in some bone proteins. As used herein, "decarboxylation" is a PTM alteration in which a carboxylic acid group is removed from glutamate residues in proteins.

In some embodiments of the present invention, the PTM reaction is a modification of proteins with a ubiquitin-like modifier selected from the group consisting of ISG15, UCRP, FUB1, NEDD8, FAT10, SUMO-1, SUMO-2, SUMO-3, Apg8, Apg12, Urm1, UBL5, and Ufm1 (see Table 1 for further description). In other embodiments of the present invention, the PTM reaction is one of ubiquitination, sumoylation, and neddylation.

The methods described herein can be used to detect changes both in PTM enzyme activity and its cognate protein targets in a patient through the analysis of a patient sample, such as plasma, CSF, or from an extract prepared from biopsy tissue. There is great need for a method that is capable of rapidly detecting biomarkers of diseases such as Alzheimer's disease or cancer in a patient sample, and to distinguish the disease from the normal state. Detecting PTMs of a large number of proteins provides a detailed fingerprint of the PTM enzymes released from tissues during disease.

In some embodiments, the functional cell extract for use in the methods described herein is obtained from a biological sample. As used herein, a "biological sample" includes, but is not limited to, saliva, blood, umbilical cord blood, serum, plasma, urine, cerebrospinal fluid (CSF), chorionic villus, lymph fluid, placenta, breast milk, nipple aspirates, pleural fluid, mucus, semen, vaginal secretions, any cell sample (heterogenous or homogenous), any solid tissue, a tumor, amniotic fluid, and a tissue culture sample. Tissue samples include but are not limited to, skin tissue, lung tissue, adipose tissue, connective tissue, sub-epithelial tissue, epithelial tissue, liver tissue, kidney tissue, uterine tissue, respiratory tissues, gastrointestinal tissue, and genitourinary tract tissue. In some embodiments, the sample is from a resection, bronchoscopic biopsy, or core needle biopsy of a primary or metastatic tumor, or a cell block from pleural fluid. In addition, fine needle aspirate samples can be used. A cell sample includes, for example, a population of cells obtained from a single-cell suspension of a tissue, for example, spleen, lymph node, or thymus. In some embodiments, a cell sample can be a heterogenous population of cells, such as the population of immune cells found in the spleen. In other embodiments, a cell sample refers to a purified population of cells, such as purified T or B cells isolated from lymph node tissue by methods known to one of skill in the art. In other embodiments, the functional cell extract can be directly prepared from a tissue or tumor by homogenization of the tissue or tumor. In some embodiments, the tumor sample refers to a biopsy of a tumor. Regarding extracellular fluids, such as interstitial fluids, lymph, CSF, blood, serum, plasma, urine, saliva, umbilical cord blood, amniotic fluid, breast milk, mucus, semen, and vaginal secretions, it is still unclear how certain intracellular proteins are deposited in such extracellular fluids, though they are expected to result from cellular turnover; nevertheless, many examples of intracellular proteins in such fluids are known. For example, it is known that cytoskeletal proteins such as tau and post-translationally modified forms thereof (phospho-tau) can be readily detected in CSF from patients suffering from Alzheimer's disease. Prior to the present invention, however, it was unknown whether functional PTM enzymes are present in extracellular fluid samples such as CSF and plasma and could be used to modify target proteins. Thus, the invention now provides a means to assay PTM enzyme activities in samples that were previously not used for such analysis.

In other embodiments, the methods described herein are useful for assaying PTM or PTM alterations of frozen or cryopreserved biological samples. Biological samples that can be frozen or cryopreserved include, but are not limited to, any of the biological samples described herein. Previously, the methods used to assay PTM or PTM alterations were limited to the use of fresh biological samples, i.e., those taken from a subject and processed immediately, or those extracts obtained from an in vivo source and processed ex vivo (i.e., isolated cells). As used herein, "cryopreservation" refers to the process where cells or whole tissues are preserved by cooling to low sub-zero temperatures, such as, 77 K or −196° C. (the boiling point of liquid nitrogen). For example, machines can be used that freeze biological samples, to be used in the methods described herein, using programmable steps, or controlled rates, before it is deep frozen, or by cryopreserving such samples in liquid nitrogen. Such machines can be used for freezing any of the biological samples described herein, including blood products, embryo, sperm, stem cells, and general tissues. Freezing must be regulated carefully to preserve the integrity of the biological sample, and lethal intracellular freezing can be avoided, for example, if cooling is slow enough to permit sufficient water to leave the cell during progressive freezing of the extracellular fluid. That rate differs between cells of differing size and water permeability: a typical cooling rate around 1° C./minute is appropriate for many mammalian cells after treatment with cryoprotectants such as glycerol or dimethyl sulphoxide (DMSO), but the rate is not a universal optimum. In some embodiments, vitrification can be performed to prepare the cryopreserved biological sample. In clinical cryopreservation, vitrification usually requires the addition of cryoprotectants prior to cooling. Cryoprotectants lower the freezing temperature and increase the viscosity of the biological sample, such that instead of crystallizing, the syrupy solution turns into an amorphous ice, i.e., it vitrifies. Vitrification of water is promoted by rapid cooling, and can be achieved without cryoprotectants by an extremely rapid drop in temperature (megakelvins per second). Many solutes do both, but larger molecules generally have larger effect, particularly on viscosity. Rapid cooling also promotes vitrification. In established methods of cryopreservation, the solute must penetrate the cell membrane in order to achieve increased viscosity and depress freezing temperature inside the cell. Sugars do not readily permeate through the membrane. Those solutes that do, such as dimethyl sulfoxide, a common cryoprotectant, are often toxic in high concentration. One of the difficult compromises faced in vitrifying cryopreservation is limiting the damage produced by the cryoprotectant itself. In general, cryopreservation is easier for thin samples and small clumps of individual cells, because these can be cooled more quickly and so require lower doses of toxic cryoprotectants. Examples of biological samples that can be cryopreserved using vitrifying cryopreservation include, but are not limited to, semen; blood and blood products such as serum and plasma; cells; stem cells; umbilical cord blood; tissue samples like tumors and histological cross sections; oocytes; 2, 4, or 8 cell embryos; and ovarian tissue. Cryoprotectant media may be, for example, supplemented with either egg yolk or soy lecithin.

The ability to use frozen or cryopreserved biological samples provides a significant and useful improvement over the standard biochemical methods used to detect PTM or PTM alterations, as such samples can be assayed long after they are obtained, and can be used to make comparisons between samples obtained at different timepoints, and from different locations. Further, if multiple biological replicates of these samples are prepared prior to the freezing or cryopreservation, a frozen or cryopreserved biological sample can be assayed multiple times. For example, the effect of a drug or treatment on PTM and PTM alterations can be assayed using cryopreserved samples taken at different timepoints from a subject being treated for a disorder. Also, cryopreserved samples can be used to compare PTM or PTM alterations between biological samples, such as a tumor biopsy, obtained from different subjects at different locations, to determine whether one or more PTM or PTM alterations or patterns of PTM or PTM alterations are shared between the same types of tumors in different subjects.

As used herein, the term "functional extract" refers to the extract of a biological sample, either in its entirety (i.e., not diluted) or any unfractionated portion or volume portion thereof, or any dilution or concentrations thereof. The term "functional extract" also includes an extracellular fluid sample obtained from a patient, applied undiluted, diluted or concentrated, in its entirety or as any mass portion or volume portion thereof. Preferably, the functional extract is not subjected to a protein purification process prior to use in a PTM or PTM alteration reaction on a solid state array, such as a protein microarray. The extract as used for a PTM or PTM alteration reaction can be supplemented with any reagent, including salts, buffers, gases, substrates, enzymes, inhibitors, etc., as desired or as appropriate for the particular PTM or PTM alteration reaction being performed.

A functional cell extract derived from a biological sample for use in the methods described herein to detect PTMs and PTM alterations can be an undiluted or concentrated extract. Accordingly, in some embodiments, the functional cell extract is not diluted prior to contacting with a solid state array. In some embodiments, functional cell extracts of patient samples or biological samples are preferably maintained at a protein concentration approaching that of in the body of the subject, so that protein-protein interactions that might affect activity are retained in the extract. In other embodiments, the functional cell extract is concentrated prior to contacting with a solid state array. In some such embodiments, the functional cell extract is highly concentrated prior to contacting with a solid state array. In such embodiments where a concentrated functional cell extract is used, the method of concentration does not involve protein purification or protein removal from the extract, but rather removal of extra cellular fluid or buffers used to isolate and prepare the cellular extract. For example, when a cell lysis solution is used to lyse a biological sample for use in the methods described herein, methods of protein concentration known to those of skill in the art can be used to concentrate the sample to form the functional cell extract prior to contacting with a solid state array for detection of a PTM or PTM alteration reaction in the extract. Non-limiting examples of methods to concentrate a functional cell extract include membrane filtering (microfiltration and ultrafiltration techniques), the use of high-speed vacuums, membrane dialysis, and TCA precipitation.

Highly concentrated cellular extracts have been shown to have demonstrable function. Such cellular extracts from Xenopus and from somatic cells that demonstrated a function specified for a particular phase of the cell cycle have allowed for the recapitulation of complex events, such as the ordered degradation of mitotic substrates (1). Also, in recent years, these systems have been employed for an in vitro expression cloning (IVEC) screening approach (2) and were used successfully to identify proteins that undergo mitosis-specific degradation (3, 4), apoptotic protease substrates (5), protein kinase substrates (5), and other binding interactions (6).

A functional cell extract derived from a biological sample for use in the methods described herein to detect PTMs and PTM alterations is essentially devoid of detergents or surfactants, as well as toxins or substances that could inhibit the biological function of components of the extract, e.g., enzymes and co-factors involved in PTM reactions, or that could denature or alter the protein targets in the microarray. In contrast to the methods described in US2008/0138836, where a commercial buffer containing three detergents are used to prepare an extract, the methods described herein allow an artisan to use a detergent-free or essentially devoid of detergents functional cell extract for detecting PTM or PTM alterations on a solid state array. Accordingly, in some embodiments, an essentially detergent-free functional cell extract is contacted with a solid state array for detecting a PTM or PTM alteration. In some embodiments, a functional cell extract is prepared from a biological sample using one or more detergent-free or essentially detergent-free solutions. In some embodiments, the functional cell extract is detergent-free. Negligible amounts of detergents, toxins, or other factors that do not affect PTM activity may be present.

A non-limiting example of a method for preparing a functional extract from a cell sample is to use a gentle, minimally diluting method such as one or more cycles of freeze-thaw, optionally combined with mildly hypotonic lysis of cells that may be present in the sample. The amount of sample material used to prepare the extract will depend on the scale of the experiment, such as the number and size of the microarrays used, but generally at least one million cells or at least an amount of tissue or bodily fluid equivalent to 50 microliters of an undiluted lysed tissue sample or cell extract, or at least about 20 μl of a bodily fluid such as plasma or cerebrospinal fluid is sufficient for preparing an extract to cover a single 1×3 inch microarray.

In order to prepare a functional extract from a cell sample, cells are first harvested using standard techniques for collecting cells, e.g., from culture or from a specimen obtained from a patient. Such techniques can include, for example, single-cell suspension preparation, tissue homogenization, treatment of tissue or cell culture with trypsin, collagenase, or other enzymes, passage through a needle, sonication, or separation by centrifugation or passage through a column, such as an affinity column. In other embodiments, purified cells can be obtained using methods and techniques known to skilled artisan for cell purification and isolation, such as magnetic bead isolation using columns, or via flow cytometric sorting techniques. Cells can be swelled in a buffer such as 25 mM HEPES, pH 7.5, containing 1.5 mM $MgCl_2$, 5 mM KCl, 1 mM DTT, optionally containing a preferred mixture of protease inhibitors, such as COMPLETE™ protease inhibitors (Roche). In some embodiments, in order to concentrated the functional cell extract, the ratio of lysis or homogenization solution preferably is kept to a minimum, e.g., similar to or less than the volume of cells being extracted, in order to minimize the dilution of extracted material. In some embodiments, a ratio of about 0.5 to 1 volume of lysis solution to cell volume can be used to concentrate the functional cell extract. In some embodiments, preferably 0.8 volumes or less of lysis solution is used for each volume of cells to be disrupted to form the concentrated functional cell extract. After homogenization, the crude cell extract can be treated to remove membranes and whole or fragmented cells, such as by centrifugation.

In some embodiments, the functional cell extract for use in the methods described herein is derived from one or more specified cellular compartments. In such embodiments, the functional cell extract derived from one or more specified cellular compartments can also be concentrated prior to contact with a solid state array. In one embodiment, the cellular compartment is nucleus. In another embodiment, the cellular compartment is cytosol. In another embodiment, the cellular compartment is mitochondria. In one embodiment, the cellular compartments are nucleus and cytosol. In one embodiment, the cellular compartments are nucleus and mitochondria. In one embodiment, the cellular compartments are cytosol and mitochondria. In some embodiments, the functional cell extract for use in the methods described herein lacks one or more specified cellular compartments. In one embodiment, the functional extract lacks nucleus. In one embodiment, the functional extract lacks cytosol. In one embodiment, the functional extract lacks mitochondria. Functional extracts can be made from these different cellular compartments according to published protocols known to one of skill in the art.

Functional extracts can be prepared from any suitable source of cells, tissue, or biological fluid that can be obtained from a patient or subject. The patient or subject can be a human or a non-human animal. The terms "subject", "patient" and "individual" are used interchangeably herein, and refer to an animal, for example a human, from whom the biological sample can be obtained from. For treatment of disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like are also encompassed in the term subject. Sources of cells or tissue for extraction can include, for example, a biopsy specimen, such as a tumor or suspected tumor, serum, plasma, cerebrospinal fluid, saliva, urine. Non-cellular (e.g., bodily fluid, interstitial fluid) samples usually contain intracellular content that is sufficient for analysis; such content may be derived, for example, from directed secretion from cells, from inflammation, or tissue damage. In other embodiments, a non-cellular biological sample comprises the media obtained from tissue culture samples.

A functional extract can be supplemented with one or more substances to aid in the analysis of a specific post-translational state or a specific PTM enzyme or PTM modifying enzyme activity. For example, an extract can be supplemented with a reagent, a substrate, an enzyme, an enzyme inhibitor, a drug, an antibody, or any mixture thereof. Alternatively, an extract can be depleted using antibodies directed to a chosen protein, protein complex, or modified protein. An extract lacking a particular protein component also can be prepared from knockout or knockdown cells. In some embodiments of the methods described herein, an additional cellular energy source in the form of, for example, ATP is provided to the functional cell extract. In one embodiment, a biochemical energy source such as ATP plus an ATP regenerating system is added to the extract or fluid to establish a reaction on the microarray. A high concentration of creatine phosphate (e.g. 150 mM) is a suitable ATP-regenerating system. Creatine phosphokinase can also be added in addition to creatine phosphate, but may be omitted if sufficiently present in the extract or fluid. Preferably, a substrate for a PTM enzyme, such as ubiquitin, is also added to the extract or fluid to establish a specific PTM reaction.

For some PTM reactions (e.g., ubiquitination, requiring E1, E2, and E3 enzymes), more than one enzyme is necessary to carry out the reaction, and while one or more enzyme is supplied by the extract or fluid sample, one or more other enzymes required for optimal activity may be limited or missing. In such cases the missing or limited enzyme or enzymes can be added to the extract or fluid to establish an optimal PTM reaction or PTM alteration reaction. A further useful strategy is to add to the extract an inhibitor of an enzyme that inhibits a particular type of PTM or PTM alteration. Examples include methyl-ubiquitin and dominant-negative E2 enzymes for ubiquitination or sumoylation. An exemplary list of enzymes that might be added to supplement a PTM reaction is provided in Table 1. One skilled in the art can readily identify additional enzymes and enzyme combinations based on existing or acquired knowledge of PTM pathways and reactions. The methods of the invention do not depend on specific combination of components.

TABLE 1

| Ubiquitin-Like Modifier | Ubiquitin Sequence Homology (%) | E1-E2-E3 Conjugating Enzymes Deconjugating Enzyme (DCE) | Substrates | Functions |
|---|---|---|---|---|
| ISG15 (UCRP) (2 ubiquitins) | 29, 27 | E1: UBE1L; E2: UBCH8 | PLCγ1, JAK1, STAT1, ERK1/2, serpin 2a | Positive regulator of IFN-related immune response, potentially involved in cell growth and differentiation |
| FUB1 (MNSFβ) | 37 | NA | TCR-α-like protein, Bcl-G | Negative regulator of leukocyte activation and proliferation |
| NEDD8 (Rub1) | 58 | E1: APPBP1-UBA3; E2: UBC12; E3: Roc1, Mdm2; DCE: DEN1/NEDP1, UCH-L1, UCH-L3, USP21, COP9 | cullins, p53, Mdm2, synphilin-1 | Positive regulator of ubiquitin E3s; directs to proteasomal degradation |
| FAT10 (2 ubiquitins) | 29, 36 | NA | MAD2 | Cell cycle checkpoint for spindle assembly, directs to proteasomal degradation |

TABLE 1-continued

| Ubiquitin-Like Modifier | Ubiquitin Sequence Homology (%) | E1-E2-E3 Conjugating Enzymes Deconjugating Enzyme (DCE) | Substrates | Functions |
|---|---|---|---|---|
| SUMO-1 (SMT3C, GMP1, UBL1) | 18 | E1: SAE-1/-2 (AOS1-UBA2); E2: UBC9; E3: RanBP2, Pc2, PIAS superfamily; DCE: SENP-1 and-2 (Ulp-1 and-2), SUSP4 | Glut1, Glut4, c-Jun, 1κBα, p53, Mdm2, SOD-1, RXRα, NEMO, PML, Sam68, RanGAP1, RanBP2, ADAR1, PCNA, Drp1, STAT-1, Sp3, thymine-DNA glycosylase, topoisomerase II | Control of protein stability, function, and localization, antagonist to ubiquitin, overlap with SUMO-2/-3 |
| SUMO-2 (SMT3B); SUMO-3 (SMT3A) | 16 | E1: SAE-1/-2; E2: UBC9; DCE: SENP-3 and-5 | RanGAP1, C/EBPβ1, topoisomerase II, thymine-DNA glycosylase | Transcription regulation, cell cycle progression |
| Apg 8 | 10 | E1: Apg7; E2: Apg3; DCE: Apg4 | Phosphatidylethanolamine | Autophagy, cytoplasm-to-vacuole targeting |
| Apg 12 | 17 | E1: Apg7; E2: Apg10 | Apg 5 | Autophagy, cytoplasm-to-vacuole targeting |
| Urm1 | 12 | E1: Uba4 | Ahp1 | Potential role in oxidative stress response |
| UBL5 (Hub1) | 25 | NA | CLK4, Snu66, Sph1, Hbt1 | Pre-mRNA splicing, appetite regulation |
| Ufm1 | 16 | E1: Uba5; E2: Ufc1 | NA | Potential role in endoplasmic stress response |

Small molecule inhibitors may also be used in a PTM reaction. Additionally, adenosine 5'-(gamma-thio)triphosphate can be added as an inhibitor of ATP-dependent processes in an extract. Also, certain proteases can be inhibited, removed, or supplemented into the reaction in order to check their effect or to find specific targets.

Any solid state array can be used for the methods described herein. A "solid state array," as used herein, refers to any combination of one or more target proteins or peptides attached to a solid support. Such a support can be a microchip, a bead, a glass slide, or any other support suitable for arraying a target protein or peptide. An array for use in the invention also can be fabricated in any desired format or dimensions and with any desired number of target proteins, as long as the position of each target protein is known and the target can be identified by its position within the array. Accordingly, in some embodiments, the solid state array for use in the methods described herein includes protein arrays on microchips, ELISA plates with immobilized proteins attached on the plates, protein-coated beads, and microfluidic chips coated with desired proteins. In some embodiments of this aspect, 2-10 PTM or PTM alterations are identified simultaneously. For example, 2, 3, 4, 5, 6, 7, 8, 9, 10 or more PTM or PTM alterations can be screened in one assay with suitable detection methods, such as labeled antibodies. In some embodiments, the multiple PTMs, PTM alterations, or combinations thereof are detected in parallel. In some embodiments, multiple PTMs, PTM alterations, or combinations thereof are detected sequentially. In such embodiments, the first PTM may affect the second PTM. Such sequential identification of PTM or PTM alteration allows one to determine PTM pathways and screen for different agents affecting various parts of the PTM or PTM alteration pathway. In some embodiments, multiplex analysis of 10-15, 10-100 PTM and/or PTM alteration reactions can be performed.

A protein microarray for use in the methods of the invention can be selected from commercially available or in-house microarrays. The array has a substrate upon which proteins are deposited in a two-dimensional array (i.e., an ordered plurality of proteins), such that each position in the array contains a single type of known protein whose PTM or PTM alteration can be investigated. The substrate of the array can be made of a material such as a glass slide, to which protein molecules are covalently or non-covalently bound. Optionally, glass can be coated with nitrocellulose or derivatized with expoxy or amino groups to provide desirable surface properties, to reduce non-specific binding, or to provide attachment points for proteins. An example of a commercially available protein microarray suitable for use in the invention is the PROTO-ARRAY® Human Protein Microarray from Invitrogen, which contains over 8000 human proteins. Other commercially available or user prepared arrays or microarrays can be used as well. In some embodiments of the methods described herein, the array comprises at least one protein, protein fragment, or peptide attached to the array with a C-terminal or N-terminal tag. Selected proteins, for example recombinant proteins that are N-terminally or C-terminally tagged and purified, can be used to prepare any desired protein microarray for use in the invention. In other embodiments, the array comprises at least one protein, protein fragment or peptide attached to the array without an added tag or moiety to facilitate binding to the solid support.

A protein array for use with the invention can have at least 2, 5, 10, 100, 1000, 8000, 10,000, 30,000, or 100,000 or more individual protein spots or wells in the array, in addition to which other locations can be added to the array for controls or background determination, or other purposes as desired. The individual proteins in the array can be all distinct, or the proteins at some positions can be identical to proteins at other positions, or can be variants (e.g., sequence mutants or differently modified versions) of proteins at other positions.

An alternative to using a protein microarray for detection is to use an array constructed from a microtiter plate or any similar container having a plurality of wells. Individual target proteins can be added to individual wells at known locations for carrying out the PTM or PTM alteration reaction and detection. It is only necessary to retain the proteins at their respective locations throughout the reaction, washing, and detection steps. For example, recombinant proteins bearing a tag, such as a GST, FLAG, or myc tag, can be coupled to glass beads that are deposited at specific locations in a microtiter plate. The beads can be retained in the wells during solution exchange, and offer the possibility to uncouple and release the modified proteins for further study, e.g., by mass spectrometry. In other embodiments, the recombinant proteins are directly deposited at specific locations in a microtiter plate, and binding is mediated by the properties of the microtiter plate. For example, untreated and irradiated polystyrene microtiter plates permit hydrophobic and hydrophilic interactions between the polystyrene and the protein being deposited.

Another alternative to using a protein microarray for detection is to use a solid state array comprising beads to which the protein targets of the PTM or PTM alteration are attached, such as a multiplex bead assay. For example, in some embodiments, protein targets of a PTM or PTM alteration are attached to beads of different sizes or colors (emission spectra) in a multiplex bead based assay. In such embodiments, a plurality of beads of different sizes is coated with different protein targets of a PTM or PTM alteration, wherein each bead of a specific size is conjugated to a specific protein target. Accordingly, each bead can be differentiated by its unique light scatter characteristics. A biological sample, such as a blood sample, to be assayed for the presence of at least one PTM or PTM alteration is then contacted with a plurality of beads of different sizes having different protein targets, thus allowing the PTM or PTM alteration to occur on one or more protein targets attached to specific beads.

In some embodiments of this aspect, such bead-based technology can be employed wherein bead populations are identified by one type of fluorescence, while the PTM or PTM alteration of the protein target on the bead is generated by one or more detection reagents carrying a second type of fluorescent signal, thus creating a bead set specific for detecting a plurality of PTM or PTM alteration. In preferred embodiments, the distinguishable bead populations are prepared by staining the beads with two or more fluorescent dyes at various ratios. Each bead having a specific ratio of the two or more fluorescent dyes is conjugated to a specific protein target, thus assigning each bead-protein target a unique fluorescent signature. The immunoassay signal is generated by detection reagents, coupled to a third type of fluorescent dye. A biological sample to be assayed for the presence of at least PTM or PTM alteration is then contacted with the plurality of beads with unique fluorescent signatures and protein target specificity, forming a PTM or PTM alteration on specific beads having the protein target of that PTM or PTM alteration. The presence of each of the at least one PTM or PTM alteration can be ascertained by flow cytometric analyses on the bead bound-target proteins. For example, in some embodiments, beads are dyed with fluorochromes having different fluorescence intensities. In some embodiments, the beads are 7.5 μm in diameter. In some embodiments, the fluorescent dye incorporated in the beads fluoresces strongly at 650 nm upon excitation with an argon laser. Each bead population of a given fluorescence intensity represents a discrete population for constructing an immunoassay for a single protein target. Each bead population having a given fluorescence intensity upon excitation is covalently coupled with a specific protein target. For example, a target of an E1 ligase. These target protein-bound bead populations, each of which are unique in their fluorescence emission intensity, serve as targets for specific PTM or PTM alteration enzymes present in a biological sample.

Accordingly, as defined herein a "capture bead" is a bead having a unique fluorescence emission intensity conjugated to a specific target protein. When these capture beads specific for different target proteins are used as a mixture, different PTM or PTM alterations, can be simultaneously measured within a given sample. In some embodiments, detection is mediated by the binding of a specific detection antibody, for example, an antibody that detects any PTM or PTM alteration present in a sample, that is directly conjugated with a fluorescent tag, such as phycoerythrin (PE), to each of the modified protein targets present after contacting with the biological sample, thus providing a second fluorescent signal for each capture bead. The fluorescent signal is proportional to the concentration of the biomarker in the sample. Separately established calibration curves can be used to determine the degree of PTM or PTM alteration in the test sample, using dedicated analysis software, such as CBA software.

The data collected using a flow cytometer includes information about the physical and spectral parameters of the beads, such as size and the fluorescence emission characteristics of each bead population. These fluorescence emission characteristics include the fluorescent emission of the dyed beads, and the potential fluorescent emissions of the detection fluorochrome (for example, phycoerythrin). When samples are analyzed using a flow cytometer in conjunction with a typical data acquisition and analysis package (for e.g., BD CellQuest™ software), a list-mode data file is saved using a flow cytometry standard file format, FCS. The data stored in the FCS files can be reanalyzed to determine the median fluorescence intensities (MFI) of the various bead populations, defined by their unique physical and spectral characteristics, to then compare reference samples with unknowns. The PTM or PTM alterations being assayed within individual samples can then be calculated from calibration curves generated by serial dilutions of standard solutions having known PTM or PTM alterations. An automated or semiautomated analysis method can be used for rapid reanalysis of the data stored in each FCS file. For example, BD CBA Software is written in the MICROSOFT® Excel Visual Basic for Applications (VBA) programming language. The CBA Software can recognize FCS 2.0 and 3.0 format data files and automates the identification of CBA bead populations and the determination of detector fluorochrome MFI values for each bead population within the data file for a single sample. Using this data analysis function of the CBA Software for multiple standard files, the MFI values for standards are then determined and plotted. From the plotted standard curve and complex mathematical interpolation, values for unknown samples can be rapidly determined in comparison to known standards using the software.

A functional extract is contacted with a solid state array, such as a protein microarray, usually by depositing an aliquot or portion of the extract, optionally after dilution or supplementation with a reagent or buffer, which may include an energy source, such as ATP and/or one or more enzymes that take part in the PTM or PTM alteration reaction, onto the surface of the microarray where proteins are deposited. Alternatively, supplements can be added after the extract is deposited onto the microarray. Once contacted with the microarray, the extract can be incubated under any desired conditions, such as at room temperature or another temperature (e.g., 30 or 37° C.), suitable to promote the protein-protein interactions and enzyme reactions necessary to allow a PTM state to be established. Generally, the incubation will last for a period ranging from several minutes to hours. The incubation conditions should be sufficient to permit a steady state level for the particular PTM reaction under consideration to be established.

One method of the invention involves detection and analysis of altered states of PTM in one or more proteins in a biological sample from a patient compared to a biological sample from a control patient, or control data, or data obtained from the same patient at an earlier time. A state of PTM can be altered, for example, if there is a change in the average number of a given chemical group attached per protein molecule, if there is a change in the type of chemical group or groups attached per protein molecule, or if there is a different mixture of protein molecules having distinct modification patterns in a patient sample. Alteration of a PTM state of a protein includes going from an unmodified protein to a modified one and vice-versa, as well as changes in the number or type of chemical moieties added to the protein.

Thus, one embodiment of the invention is a method of identifying an altered PTM state of a protein in a patient. The method includes the steps of (i) contacting a functional extract of a sample from the patient with a protein microarray containing proteins that are representative of proteins in the patient; (ii) establishing a specific PTM reaction on the microarray, whereby the reaction results in a PTM of one or more proteins in the microarray through the activity of one or more enzymes present in the extract; (iii) determining the level of PTM of proteins in the microarray; and (iv) comparing the levels of PTM with PTM levels of corresponding proteins in a control sample to identify altered PTM states of one or more proteins in the patient.

A specific PTM reaction can be established on an array by adding a substrate (e.g., ubiquitin) to the extract or fluid sample that is required for a single PTM reaction. An assay also can be rendered specific for a single PTM reaction by the use of an antibody that detects only one specific PTM state. Methods according to the invention can be addressed to either a single specific PTM reaction at a time or more than one specific PTM reactions performed simultaneously in the same reaction mixture (multiplex format).

The particular target proteins in the microarray can be selected so as to be representative of the proteins available in the patient. For example, the microarray can include a large number of human proteins if the patient is a human patient. In one embodiment, the proteins in the microarray are initially in an unmodified state, such as that obtained by expressing the proteins in a recombinant expression system that does not modify the proteins. In another embodiment, the proteins in the microarray have various states of PTM; such proteins can be further modified by a functional extract, providing differential modification signals. Alternatively, in another embodiment the target proteins in the array can be biochemically stripped of certain PTMs prior to exposure to the functional extract for analysis. During the step of contacting the functional extract with the microarray, one or more proteins in the array will become post-translationally modified by the enzymes, cofactors, and substrates in the extract.

Following an appropriate incubation period, the cell extract can be washed off the microarray by standard techniques, including spin drying, centrifugation, or blowing a stream of gas (e.g., air or nitrogen) over the surface of the microarray followed by application of a buffer solution to the microarray. The washing step can be repeated as needed to remove components from the cell extract from the microarray, leaving the modified target proteins attached to the microarray for subsequent detection. A suitable washing solution is a Tris buffered saline solution (TBS), optionally supplemented with one or more detergents (e.g., 0.05% Tween, or for more stringent conditions 0.5% SDS) to dissociate non-specifically bound proteins from the proteins in the array.

After the cell extract has been removed, the next step is to determine the level of PTM of individual proteins in the microarray. This can be accomplished, for example, using an antibody that specifically binds all proteins having a specific type of modification. Many such antibodies are commercially available, such as Anti-Polyubiquitin (BioMol), anti-ubiquitin (with specific linkages, Cell Signaling), anti-sumo1 (Cell Signaling, BioMol), anti-sumo2/3 (Cell Signaling, Biomol), anti-NEDD8 (Biomol, MB1, Sigma), anti-APG8 (Boston Biochem), anti-FAT10 (Boston Biochem), and anti-UFM1 (Boston Biochem). Examples of commercially available antibodies that can be used to specifically detect different PTM and PTM alteration states are listed in Table 2.

TABLE 2

| PTM Detected/Antibody | Catalog Number | Company |
|---|---|---|
| Ubiquitin monoclonal mouse monoclonal | AB-001 | Cell Signaling |
| SUMO2 polyclonal mouse polyclonal | AB-S80 | Cell Signaling |
| SUMO2 monoclonal mouse monoclonal | AB-S81 | Cell Signaling |
| SUMO3 MaxPab polyclonal mouse polyclonal | AB-S90 | Cell Signaling |
| SUMO3 polyclonal mouse polyclonal | AB-S91 | Cell Signaling |
| SUMO3 monoclonal mouse monoclonal | AB-S92 | Cell Signaling |
| SUMO3 monoclonal mouse monoclonal | AB-S93 | Cell Signaling |
| SUMO4 MaxPab polyclonal mouse polyclonal | AB-S95 | Cell Signaling |
| SUMO4 polyclonal rabbit polyclonal | AB-S96 | Cell Signaling |
| SUMO4 polyclonal rabbit polyclonal | AB-S97 | Cell Signaling |
| Anti-NEDD8 rabbit polyclonal | A-812 | Cell Signaling |

TABLE 2-continued

| PTM Detected/Antibody | Catalog Number | Company |
|---|---|---|
| Anti-UBE1L (E1) rabbit polyclonal | A-306 | Cell Signaling |
| Anti-ISG15 rabbit polyclonal | A-600 | Cell Signaling |
| UBE2L6 (UbcH8) MaxPab polyclonal mouse polyclonal | AB-242 | Cell Signaling |
| UBE2L6 polyclonal mouse polyclonal | AB-243 | Cell Signaling |
| UBE2L6 (UbcH8) monoclonal mouse monoclonal | AB-244 | Cell |
| Ubiquitin monoclonal mouse monoclonal | AB-001 | Cell Signaling |
| SUMO2 polyclonal mouse polyclonal | AB-S80 | Cell Signaling |
| SUMO2 monoclonal mouse monoclonal | AB-S81 | Cell Signaling |
| SUMO3 MaxPab polyclonal mouse polyclonal | AB-S90 | Cell Signaling |
| SUMO3 polyclonal mouse polyclonal | AB-S91 | Cell Signaling |
| SUMO3 monoclonal mouse monoclonal | AB-S92 | Cell Signaling |
| SUMO3 monoclonal mouse monoclonal | AB-S93 | Cell Signaling |
| SUMO4 MaxPab polyclonal mouse polyclonal | AB-S95 | Cell Signaling |
| SUMO4 polyclonal rabbit polyclonal | AB-S96 | Cell Signaling |
| SUMO4 polyclonal rabbit polyclonal | AB-S97 | Cell Signaling |
| Anti-NEDD8 rabbit polyclonal | A-812 | Cell Signaling |
| Anti-UBE1L (E1) rabbit polyclonal | A-306 | Cell Signaling |
| Anti-ISG15 rabbit polyclonal | A-600 | Cell Signaling |
| UBE2L6 (UbcH8) MaxPab polyclonal mouse polyclonal | AB-242 | Cell Signaling |
| UBE2L6 polyclonal mouse polyclonal | AB-243 | Cell Signaling Signaling |
| ISG15 MaxPab polyclonal rabbit polyclonal | AB-I10 | Cell Signaling |
| ISG15 monoclonal clonal mouse monoclonal | AB-I11 | Cell Signaling |
| Anti-UFM1 rabbit polyclonal | A-500 | Cell Signaling |
| APG3 polyclonal mouse recombinant | AB-A10APG3 | Cell Signaling |
| APG3 monoclonal mouse monoclonal | AB-A11APG3 | Cell Signaling |
| APG4B polyclonal rabbit polyclonal | AB-A20APG4B | Cell Signaling |
| APG4C MaxPab polyclonal mouse polyclonal | AB-A21APG4C | Cell |
| Ubiquitin monoclonal mouse monoclonal | AB-001 | Cell Signaling |
| SUMO2 polyclonal mouse polyclonal | AB-S80 | Cell Signaling |
| SUMO2 monoclonal mouse monoclonal | AB-S81 | Cell Signaling |
| SUMO3 MaxPab polyclonal mouse polyclonal | AB-S90 | Cell Signaling |
| SUMO3 polyclonal mouse polyclonal | AB-S91 | Cell Signaling |
| SUMO3 monoclonal mouse monoclonal | AB-S92 | Cell Signaling |
| SUMO3 monoclonal mouse monoclonal | AB-S93 | Cell Signaling |
| SUMO4 MaxPab polyclonal mouse polyclonal | AB-S95 | Cell Signaling |
| SUMO4 polyclonal rabbit polyclonal | AB-S96 | Cell Signaling |
| SUMO4 polyclonal rabbit polyclonal | AB-S97 | Cell Signaling |
| Anti-NEDD8 rabbit polyclonal | A-812 | Cell Signaling |
| Anti-UBE1L (E1) rabbit polyclonal | A-306 | Cell Signaling |

TABLE 2-continued

| PTM Detected/Antibody | Catalog Number | Company |
|---|---|---|
| Anti-ISG15 rabbit polyclonal | A-600 | Cell Signaling |
| UBE2L6 (UbcH8) MaxPab polyclonal mouse polyclonal | AB-242 | Cell Signaling |
| UBE2L6 polyclonal mouse polyclonal | AB-243 | Cell Signaling |
| | | Signaling |
| APG4C polyclonal rabbit polyclonal | AB-A22APG4C | Cell Signaling |
| APG5 monoclonal mouse monoclonal | AB-A25APG5 | Cell Signaling |
| APG7 MaxPab polyclonal mouse polyclonal | AB-A30APG7 | Cell Signaling |
| APG7 polyclonal rabbit polyclonal | AB-A31APG7 | Cell Signaling |
| APG9A polyclonal rabbit polyclonal | AB-A40APG9 | Cell Signaling |
| APG10 polyclonal rabbit polyclonal | AB-A50APG10 | Cell Signaling |
| APG10 polyclonal rabbit polyclonal | AB-A51APG10 | Cell |
| Ubiquitin monoclonal mouse monoclonal | AB-001 | Cell Signaling |
| SUMO2 polyclonal mouse polyclonal | AB-S80 | Cell Signaling |
| SUMO2 monoclonal mouse monoclonal | AB-S81 | Cell Signaling |
| SUMO3 MaxPab polyclonal mouse polyclonal | AB-S90 | Cell Signaling |
| SUMO3 polyclonal mouse polyclonal | AB-S91 | Cell Signaling |
| SUMO3 monoclonal mouse monoclonal | AB-S92 | Cell Signaling |
| SUMO3 monoclonal mouse monoclonal | AB-S93 | Cell Signaling |
| SUMO4 MaxPab polyclonal mouse polyclonal | AB-S95 | Cell Signaling |
| SUMO4 polyclonal rabbit polyclonal | AB-S96 | Cell Signaling |
| SUMO4 polyclonal rabbit polyclonal | AB-S97 | Cell Signaling |
| Anti-NEDD8 rabbit polyclonal | A-812 | Cell Signaling |
| Anti-UBE1L (E1) rabbit polyclonal | A-306 | Cell Signaling |
| Anti-ISG15 rabbit polyclonal | A-600 | Cell Signaling |
| UBE2L6 (UbcH8) MaxPab polyclonal mouse polyclonal | AB-242 | Cell Signaling |
| UBE2L6 polyclonal mouse polyclonal | AB-243 | Cell Signaling |
| | | Signaling |
| APG12 MaxPab polyclonal mouse polyclonal | AB-A64APG12 | Cell Signaling |
| APG12 polyclonal rabbit polyclonal | AB-A65APG12 | Cell Signaling |
| APG12 monoclonal mouse monoclonal | AB-A66APG12 | Cell Signaling |
| URM1 polyclonal rabbit polyclonal | AB-O30 | Cell Signaling |
| Anti Fat10 (Protein derived) | PW9680-002 | Biomol |
| anti-Fat10 Polyclonal | PW9585-0025 | Biomol |
| anti-URM1 polyclonal | PW9595-0025 | Biomol |
| anti-FUB1 polyclonal | PW9615-0025 | Biomol |
| Mouse Anti-O-GlcNAc Monoclonal Antibody | sc-81483 | Santa Cruz |
| Ubiquitin monoclonal mouse monoclonal | AB-001 | Cell Signaling |
| SUMO2 polyclonal mouse polyclonal | AB-S80 | Cell Signaling |
| SUMO2 monoclonal mouse monoclonal | AB-S81 | Cell Signaling |
| SUMO3 MaxPab polyclonal mouse polyclonal | AB-S90 | Cell Signaling |
| SUMO3 polyclonal mouse polyclonal | AB-S91 | Cell Signaling |
| SUMO3 monoclonal mouse monoclonal | AB-S92 | Cell Signaling |
| SUMO3 monoclonal mouse monoclonal | AB-S93 | Cell Signaling |

TABLE 2-continued

| PTM Detected/Antibody | Catalog Number | Company |
|---|---|---|
| SUMO4 MaxPab polyclonal mouse polyclonal | AB-S95 | Cell Signaling |
| SUMO4 polyclonal rabbit polyclonal | AB-S96 | Cell Signaling |
| SUMO4 polyclonal rabbit polyclonal | AB-S97 | Cell Signaling |
| Anti-NEDD8 rabbit polyclonal | A-812 | Cell Signaling |
| Anti-UBE1L (E1) rabbit polyclonal | A-306 | Cell Signaling |
| Anti-ISG15 rabbit polyclonal | A-600 | Cell Signaling |
| UBE2L6 (UbcH8) MaxPab polyclonal mouse polyclonal | AB-242 | Cell Signaling |
| UBE2L6 polyclonal mouse polyclonal | AB-243 | Cell Signaling |
| S-nitrosocysteine antibody | ab50185 | Abcam |
| Acetylated-Lysine Antibody | #9441 | Cell Signaling |
| acetyl Lysine antibody | ab76 | Abcam |
| Citrulline polyclonal antibody | PAB0068 | Abnova |

In order to visualize the specifically bound antibody molecules on the microarray, the unbound first antibody is first washed away and a second antibody (e.g., an anti-immunoglobulin that specifically binds the first antibody) can be added to the microarray and allowed to bind with the first antibody. The second antibody can be labeled, e.g., by conjugation to a label moiety such as a fluorescent dye, so as to generate a signal permitting detection by a microarray scanner, such as a GenePix 4000B (Molecular Devices). Preferably, the signal emitted to detect post-translationally modified proteins in the microarray is a light signal, though other signals such as radioactivity can be used as well. The scanner can detect both the amount of signal and its position within the microarray. Two or more PTMs or PTM alterations can be detected simultaneously by using a selection of different first antibodies, each binding specifically to a different protein modification and each recognized by a different second antibody, with each second antibody conjugated to a different labeling moiety (e.g., different fluorescent dyes having excitation and emission wavelengths selected to enable simultaneous detection). An alternative method is to use labeled primary antibodies specific for the PTM or PTM alterations instead of using secondary antibodies. The data can be output as an image, or as an amount of signal detected in each spot of the microarray.

An alternative method for detecting PTM of proteins in the microarray is to add the modifying moiety (e.g., a protein such as ubiquitin or sumo that is added during the PTM reaction) in a tagged form, such as a His-, GST-, or Myc-tagged moiety, and to detect the tagged molecule using a specific antibody for the tag (e.g., anti-His, anti-GST, or anti-Myc antibody. In yet another alternative method of detection, a modification moiety can be labeled with a labeling moiety such as biotin or a $^{35}$S-labeled or radioiodinated amino acid. Phosphorylation of proteins can be detected using an antibody specific for a phosphoprotein or by adding gamma-$^{32}$P-ATP into the reaction. Many techniques, such as streptavidin binding or autoradiography, can be used to visualize such labeled modification moieties instead of using antibodies, or where an appropriate antibody is not available.

Yet another method of detecting modification of proteins in the microarray is to harvest the proteins from individual spots in the array and to perform biochemical analysis, e.g., by mass spectrometry, to identify the nature of the modification, such as the number and position of modified amino acids in the protein sequence. This can be accomplished, for example, by treating individual protein-containing spots with a proteolytic enzyme such as trypsin, or by using a specifically labile chemical linkage to the substrate of the array. Quantities of individual proteins in the pg to ng range can be recovered from microarray spots; such amounts are sufficient for a wide variety of biochemical analyses, including peptide mapping, amino acid sequencing, and mass spectroscopy.

In such embodiments, the modification of proteins in the microarray can be determined by mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference in their entirety.

The terms "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., "Proteinchip surface enhanced laser desorption/ionization (SELDI) mass spectrometry: a novel protein biochip technology for detection of prostate cancer biomarkers in complex protein mixtures," Prostate Cancer and Prostatic Diseases 2: 264-76 (1999); and Merchant and Weinberger, "Recent advancements in surface-enhanced laser desorption/ionization-time of flight-mass spectrometry," Electrophoresis 21: 1164-67 (2000), each of which is hereby incorporated by reference in its entirety, including all tables, figures, and claims. Mass spectrometry methods are well known in the art and have been used to quantify and/or identify biomolecules, such as proteins and hormones (see, e.g., Li et al., (2000), Tibtech. 18:151-160; Starcevic et. al., (2003), J. Chromatography B, 792: 197-204; Kushnir M M et. al. (2006), Clin. Chem. 52:120-128; Rowley et al. (2000), Methods 20: 383-397; and Kuster and Mann (1998), Curr. Opin. Structural Biol. 8: 393-400). Further, mass spectrometric techniques have been developed that permit at least partial de novo sequencing of isolated proteins. Chait et al., (1993), Science, 262:89-92; Keough et al., (1999), Proc. Natl. Acad. Sci. USA. 96:7131-6; reviewed in Bergman (2000), EXS 88:133-44.

Various methods of ionization are known in the art. For examples, Atmospheric Pressure Chemical Ionisation (APCI) Chemical Ionisation (CI) Electron Impact (EI) Electrospray Ionisation (ESI) Fast Atom Bombardment (FAB) Field Desorption/Field Ionisation (FD/FI) Matrix Assisted Laser Desorption Ionisation (MALDI) and Thermospray Ionisation (TSP). In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937 (Hillenkamp et al.), and U.S. Pat. No. 5,045,694 (Beavis & Chait).

In SELDI, the substrate surface is modified so that it is an active participant in the desorption process. In one variant, the surface is derivatized with adsorbent and/or capture reagents that selectively bind the protein modification of interest. In another variant, the surface is derivatized with energy absorbing molecules that are not desorbed when struck with the laser. In another variant, the surface is derivatized with molecules that bind the protein modification of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material. For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094. Detection and quantification of the biomarker will typically depend on the detection of signal intensity. For example, in certain embodiments, the signal strength of peak values from spectra of a first sample and a second sample can be compared (e.g., visually, by computer analysis etc.), to determine the relative amounts of particular biomarker. Software programs such as the Biomarker Wizard program (Ciphergen Biosystems, Inc., Fremont, Calif.) can be used to aid in analyzing mass spectra. The mass spectrometers and their techniques are well known to those of skill in the art.

The methods described herein involves detection and analysis of PTMs and PTM alterations using any composition or agent that can be detected by spectroscopic, photochemical, biochemical, immunochemical, electrical, optical or chemical means, thus providing a detectable signal to identify the PTM or PTM alteration. A PTM or PTM alteration can be detected using the methods described herein, for example, if there is a change in the average number of a given chemical group attached per protein molecule, if there is a change in the type of chemical group or groups attached per protein molecule, or if there is a different mixture of protein molecules having distinct modification patterns in a patient sample with respect to a control sample. Alteration of a PTM state of a protein includes going from an unmodified protein to a modified one and vice-versa, as well as changes in the number or type of chemical moieties added to the protein. A control sample or level is used herein to describe a control patient, control or reference data, or data obtained from the same patient at an earlier time. For example, in some embodiments, a control sample is a functional cell extract obtained from a biological sample obtained from a subject not suffering from the disease being examined in the test sample. In another example, a control sample is a functional cell extract obtained population of cells obtained from the same biological source that has been treated with identical media, culture condition, temperature, confluency, flask size, pH, etc., with the exception of a test agent.

Accordingly, in some embodiments, an increase in the signal from a solid-state array compared to a background or the reaction with a control is indicative of increased PTM. The terms "increased," "increase," or "enhance" are all used herein to generally mean an increase by a statically significant amount; for the avoidance of any doubt, the terms "increased," "increase," or "enhance" mean an increase, as compared to a reference level, of at least about 10%, of at least about 15%, of at least about 20%, of at least about 25%, of at least about 30%, of at least about 35%, of at least about 40%, of at least about 45%, of at least about 50%, of at least about 55%, of at least about 6o %, of at least about 65%, of at least about 70%, of at least about 75%, of at least about 80%, of at least about 85%, of at least about 90%, of at least about 95%, or up to and including a 100%, or at least about a 2-fold, or at least about a 3-fold, or at least about a 4-fold, or at least about a 5-fold, at least about a 6-fold, or at least about a 7-fold, or at least about a 8-fold, at least about a 9-fold, or at least about a 10-fold increase, or any increase of 10-fold or greater, as compared to a control sample or level.

In some embodiments, a decrease in the signal from a solid-state array compared to a background or the reaction with a control is indicative of a PTM alteration. The terms "decreased," "decrease," or "reduce" are all used herein to generally mean a decrease by a statically significant amount; for the avoidance of any doubt, the terms "decreased," "decrease," or "reduce" mean a decrease, as compared to a reference or control level, of at least about 10%, of at least about 15%, of at least about 20%, of at least about 25%, of at least about 30%, of at least about 35%, of at least about 40%, of at least about 45%, of at least about 50%, of at least about 55%, of at least about 6o %, of at least about 65%, of at least about 70%, of at least about 75%, of at least about 80%, of at least about 85%, of at least about 90%, of at least about 95%, or up to and including a 100%.

Preferably, the microarray includes control spots (e.g., spotted with buffer but no protein or of GST spotted on the array) distributed across the array which can be used for background subtraction or normalization. Analysis of the distribution of background signal intensities as well as the distribution of control modified protein signal intensities, taking into account the signal-to-noise ratio, will suggest an appropriate threshold level of signal intensity considered to be significant enough to represent a positive result (i.e., detection of a post-translationally modified protein).

After the level of the PTM state for one or more proteins in the solid state array, such as a microarray has been detected, alteration of this state can be identified by comparing the results for each individual protein to similar results obtained using a control sample. The control sample can be obtained from another patient, for example, or obtained from the same patient at an earlier date or from a control tissue sample obtained from another subject. A functional extract prepared from the control is used in the same method as for the test subject and applied to a second protein microarray, preferably an identical microarray to the first microarray used for the test subject, having the same proteins as the first microarray. Alternatively, comparison data can be used that have been generated using a set of patients, or data representing known or defined ratios of certain modifications. The level of a PTM state for a given protein in the first microarray (results for the test subject) is compared to the level obtained for the corresponding protein in the second microarray. Analysis of the change in state, e.g., the direction and extent of change, or the presence or absence of any change, optionally can be used to diagnose a disease or medical condition, to determine a physiological, metabolic, or developmental state, to assess the effectiveness of a drug in the patient, or to identify target proteins for treatment based on either different modification activity or different modification state.

The analysis of functional extracts using protein microarrays can also be applied to a method for identifying a PTM state of a protein. This method can be applied either to a patient sample, or to any specimen of cells or living tissue. A functional extract is prepared from the patient sample or cell or tissue specimen, as outlined above. The extract, or a portion or dilution of the extract, is contacted with a protein microarray as described earlier, and one or more proteins in the microarray becomes post-translationally modified, or a PTM becomes altered (e.g., degree of polyubiquitination) or is removed, i.e., PTM alteration. Optionally, the extract is supplemented with one or more reagents, co-factors, substrates, enzymes, or antibodies either prior to or during the step of contacting the microarray. A signal is then detected from the modified proteins in the array, such as the fluorescence signal obtained from primary and labeled secondary antibodies as described previously. The signal, preferably background subtracted, is correlated with the identity of the protein in the respective position in the microarray, which results in identification of a PTM state of a particular protein.

A method of diagnosing a disease or medical condition related to a pattern of protein PTM can be carried out using the strategies outlined above. A functional extract is prepared from a sample of a patient suspected of having a certain disease or medical condition. The extract, or a portion or dilution of the extract, optionally substituted with one or more reagents to promote and/or stabilize a particular PTM reaction, is contacted with a protein microarray. The microarray contains an ordered array of proteins corresponding to proteins in the patient. During the incubation of the extract on the microarray, one or more target proteins in the array become post-translationally modified. The extract is washed away and the modified proteins in the microarray are detected, using a strategy such as described earlier, for example, by detecting a fluorescence signal from a primary/secondary antibody pair. The pattern of signals from the microarray are measured and recorded to form a PTM data set for the patient sample. The patient data set is compared to a standard data set containing a pattern of PTM states that is characteristic or diagnostic for the disease or medical condition.

This type of diagnostic assay can be applied to a wide variety of diseases, medical conditions, and biological states. A number of diseases or conditions for which PTMs are known or suspected to play a role are summarized in Table 3. The methods of the present invention are particularly suited to diagnosing diseases or medical conditions including, but not limited to: cancer, such as breast cancer, ovarian cancer, uterine cancer, brain cancer, including astrocytoma, renal cell carcinoma, and vascular tumors of the central nervous system; neurodegenerative diseases, such as Alzheimer's disease, Parkinson's disease, Huntington's disease, amyelotrophic lateral sclerosis, multiple sclerosis, prion diseases, neuronal intranuclear disease, Rett syndrome, and Rubenstein-Taybi syndrome; metabolic diseases, such as diabetes mellitus, diabetic ventricular dysfunction, and gaut; immune diseases, including autoimmune diseases, rheumatoid arthritis, collagen-induced arthritis, systemic lupus erythematosus, celiac disease, encephalomyelitis, and IgA neuropathy; infectious diseases, such as viral diseases; cardiovascular diseases, such as cardiac dysfunction and atherosclerosis; and biological states such as cell cycle progression, DNA damage and repair, apoptosis, the NFkB pathway, Fanconi anemia, tumorigenesis, cellular, tissue, and embryonic differentiation, and aging. PTMs that may contribute to tumorigenesis include phosphorylation, acetylation, methylation, glycosylation, prolyl isomerization, hydroxylation, oxidation, glutathionylation, and ubiquitination.

TABLE 3

| PTM | DISEASE | MODIFIED PROTEIN | REFERENCE | TITLE |
|---|---|---|---|---|
| Ubiquitination | Cancer/tumor | cMyc, HectH9 (E3 ligase) | 33 | The ubiquitin ligase HectH9 regulates transcriptional activation by Myc and is essential for tumor cell proliferation |
| Ubiquitination | Cancer/tumor, Breast and ovarian cancer | BRCA1 (E3 ligase) | 34 | Ubiquitination and proteasomal degradation of the BRCA1 tumor suppressor is regulated during cell cycle progression. |

TABLE 3-continued

| PTM | DISEASE | MODIFIED PROTEIN | REFERENCE | TITLE |
|---|---|---|---|---|
| SUMOylation | Cancer/tumor | Ubc9 (E2 conjugating enzyme) | 35 | A role for Ubc9 in tumorigenesis |
| Ubiquitination | Alzheimers disease | Bcl-2 | 36 | Inhibition of the ubiquitin-proteasome system in Alzheimer's Disease |
| Glycosylation | Alzheimers disease | tau | 37 | Glycosylation of microtubule-associated protein tau: an abnormal posttranslational modification in Alzheimer's disease |
| K48-linked and K63-linked ubiquitination | Parkinson's disease | synphilin-1, parkin, α-synuclein, UCHL1 | 38 | Parkin mediated lysine 63-linked polyubiquitination: a link to protein inclusions formation in Parkinson's and other conformational diseases? |
| Ubiquitination | Parkinson's Disease, Autophagy | Parkin | 39 | Parkin-mediated K63-linked polyubiquitination: a signal for targeting misfolded proteins to the aggresome-autophagy pathway. |
| Ubiquitination | Neurodegenerative Diseases | P62 | 40 | Lysine 63-linked polyubiquitin potentially partners with p62 to promote the clearance of protein inclusions by autophagy. |
| Acetylation, deacetylation, methylation | Neurologic and psychiatric disorders including Huntington's disease, Parkinson's disease, anxiety and mood disorders, Rubinstein-Taybi syndrome, and Rett syndrome | HDAC | 41 | Epigenetic targets of HDAC inhibition in neurodegenerative and psychiatric disorders. |
| Nedd8ylation | Neurodegenerative Diseases, Parkinson's disease and Rosenthal fibres in astrocytoma | NEDD8 | 42 | Accumulation of NEDD8 in neuronal and glial inclusions of neurodegenerative disorders. |
| | Neurodegenerative diseases | Mad2, BubR1 associated to cDc20 | 43 | Inhibitory factors associated with anaphase-promoting complex/cylosome in mitotic checkpoint. |
| Ubiquitination | Cell Cycle progression | | 44 | Ubiquitin dependence of selective protein degradation demonstrated in the mammalian cell cycle mutant ts85. |
| | Cell Cycle progression | cyclin | 45 | Cyclin: a protein specified by maternal mRNA in sea urchin eggs that is destroyed at each cleavage division. |
| | Cell Cycle progression | APC/C (cDc20, CDH1 and MAD2) | 46 | Control of mitotic transitions by the anaphase-promoting complex. |
| Conjugation | Cell Cycle progression | cyclin | 47 | Cyclin is degraded by the ubiquitin pathway. |
| Ubiquitination | Cell Cycle progression | Cdc34, CDK activity-by degrading CDK activators or inhibitors | 48 | How proteolysis drives the cell cycle |
| Ubiquitination | Cell Cycle progression | APC/C (cDc20, MAD2) | 49 | Ubiquitination by the anaphase-promoting complex drives spindle checkpoint inactivation. |
| Ubiquitination, phosphorylation, methylation DNA damage and repair | DNA damage and repair | ATR/MRN complex | 50 | Twists and turns in the function of DNA damage signaling and 5 repair proteins by PTMs. |

TABLE 3-continued

| PTM | DISEASE | MODIFIED PROTEIN | REFERENCE | TITLE |
|---|---|---|---|---|
| Acetylation, methylation, phosphorylation, ubiquitination and SUMOylation | Huntington disease | Histone (H2A, H2B, H3 and H4) | 51 | Mechanisms of disease: Histone modifications in Huntington's disease. |
| SUMOylation | Huntington disease | Huntingtin (Httex1p) | 52 | SUMO modification of Huntingtin and Huntington's disease pathology. |
| Ubiquitination, SUMOylation, phosphorylation, acetylation and nitrosylation | NFkB pathway | IkappaB kinase (IKK) complex, the IkappaB proteins and the NF-kappaB | 53 | PTMs regulating the activity and function of the nuclear factor kappa B pathway. |
| SUMOylation | Neuronal Intranuclear Inclusion disease (NIID) | SUMOylation substrates: Promyelocytic leukaemia protein (PML) and RanGAP1.HDAC4 | 54 | SUMOylation substrates in neuronal intranuclear inclusion disease. |
| SUMOylation | Type 1 diabetes | M55V substitution of SUMO4 | 55 | SUMO wrestling with type 1 diabetes. |
| SUMOylation | Polyglutamine Diseases | ESCA1 and ESCA2 | 56 | Enhanced SUMOylation in polyglutamine diseases |
| Ubiquitination | Kidney cancers | HIF-alpha | 57 | The role of von Hippel-Lindau tumor suppressor protein and hypoxia in renal clear cell carcinoma. |
| Neddylation, SUMOylation, | Renal cell carcinomas, pheochromocytomas, and vascular tumors of the central nervous system | pVHL, NEDD8 conjugation to Cul-2 | 58 | The von Hippel-Lindau tumor suppressor gene product promotes, but is not essential for, NEDD8 conjugation to cullin-5 2. |
| SUMOylation | Diabetes mellitus, diabetic ventricular dysfunction | ERK5, Ubc9 (SUMO E2 conjugase) or PIAS1 (E3 ligase) | 59 | Effects of MEK5/ERK5 association on small ubiquitin-related modification of ERK5: implications for diabetic ventricular dysfunction after myocardial infarction. |
| Ubiquitination, SUMOylation | Parkinson's, Alzheimer's, Huntington's, Prion and amyotrophic lateral sclerosis | αSYN (PARK1), UCH-L1, DJ-1 binds to the SUMO E3 PIASx, Aβ and tau, UBB + 1etc . . . | 60 | The ubiquitin proteasome system in neurodegenerative diseases: sometimes the chicken, sometimes the egg. |
| Methylation, deimination, and phosphorylation | Multiple Sclerosis | MBP | 61 | Multiple sclerosis: an important role for PTMs of myelin basic protein in pathogenesis. |
| Glycosylation | Autoimmunity, Rheumatoid arthritis and IgA nephropathy | IgG and IgA1 | 62 | Plasma proteins glycosylation and its alteration in disease. |
| SUMOylation | Parkinson | DJ-1 | 63 | Proper SUMO-1 conjugation is essential to DJ-1 to exert its full activities. |
| SUMOylation | Parkinson | DJ-1, and pyrimidine tract-binding protein-associated splicing factor (PSF) | 64 | DJ-1 transcriptionally up-regulates the human tyrosine hydroxylase by inhibiting the sumoylation of pyrimidine tract-binding protein-associated splicing factor. |
| Ubiquitination, phosphorylation and acetylation | Cancer | p53 | 65 | Ubiquitination, phosphorylation and acetylation: the molecular basis for p53 regulation. |
| Phosphorylation | Cancer | Fra-1 | 66 | Accumulation of Fra-1 in ras-transformed cells depends on both transcriptional autoregulation and MEK-dependent posttranslational stabilization. |
| Phophorylation | Cancer | NF-kappa B | 67 | Inhibition of constitutive NF-kappa B activity by I kappa B alpha M suppresses tumorigenesis. |

TABLE 3-continued

| PTM | DISEASE | MODIFIED PROTEIN | REFERENCE | TITLE |
|---|---|---|---|---|
| Ubiquitination, SUMOylation | Cancer | Smad4 | 68 | Sumoylation of Smad4, the common Smad mediator of transforming growth factor-beta family signaling. |
| Phophorylation | Uterine leiomyomas | Ref-1 | 69 | Altered PTM of redox factor 1protein in human uterine smooth muscle tumors. |
| Phophorylation | tumorigenesis, differentiation and apoptosis | p53, GSK3beta | 70 | Glycogen synthase kinase3 beta phosphorylates serine 33 of p53 and activates p53's transcriptional activity. |
| Phophorylation | tumorigenesis | pp60c-src | 71 | pp60c-src in human melanocytes and melanoma 30 cells exhibits elevated specific activity and reduced tyrosine 530 phosphorylation compared to human fibroblast pp60c-src. |
| Phophorylation | tumorigenesis | P120 | 72 | Abelson murine leukemia virus transformationdefective mutants with impaired P120 associated protein kinase activity. |
| Glycosylation | Prion Disease | PrP | 73 | Asparagine-linked glycosylation of the scrapie and cellular prion proteins. |
| Ubiquitination | Fanconi anemia | FANCD2 | 74 | Fanconi anemia: causes and consequences of genetic instability. |
| Ubiquitination | Fanconi anemia | FANCD2, catalytic subunit PHF9(FANCL) | 75 | A novel ubiquitin ligase is deficient in Fanconi anemia. |
| Ubiquitination | Aging | BRCA1; PCNA; NFκB; p27; $SNEV^{Prp19/Pso4}$ | 76 | Aging and the ubiquitinome: traditional and non-traditional functions of ubiquitin in aging cells and tissues. |
| Ubiquitination, SUMOylation, Oxydation | Aging | | 77 | Aging and dietary restriction effects on ubiquitination, sumoylation, and the proteasome in the heart. |
| Ubiquitination | Aging | DAF-16, RLE-1 (E3 ligase) | 78 | RLE-1, an E3 ubiquitin ligase, regulates *C. elegans* aging by catalyzing DAF-16 polyubiquitination. |
| SUMOylation | Aging | POMP-1 | 79 | Effects of aging and dietary restriction on ubiquitination, sumoylation, and the proteasome in the spleen. |
| | Aging | Decrease of expressed Proteasome proteins: S9: Rpn6 (p44.5), Rpn5 (p55), a2 (HC3), a7(HC8), S7: Rpt1 (MSS1) and S10b: Rpt4 (p42) | 80 | Caretaker or undertaker? The role of the proteasome in aging |
| S-nitrosylation, Ubiquitination | Parkinson's disease | parkin | 81 | Nitrosative stress linked to sporadic Parkinson's disease: S-nitrosylation of parkin regulates its E3 ubiquitin ligase activity. |
| Glycosylation | Virus related diseases | penv9, penv14 | 82 | Glycosylation inhibitors block the expression of LAV/HTLV-III (HIV) glycoproteins. |

TABLE 3-continued

| PTM | DISEASE | MODIFIED PROTEIN | REFERENCE | TITLE |
|---|---|---|---|---|
| Glycosylation | Virus related diseases | gp46 | 83 | Immunogenicity and conformational properties of an N-linked glycosylated peptide epitope of human T-lymphotropic virus type 1 (HTLVI). |
| Glycosylation | Virus related diseases | peroxiredoxin 1 and HTLV-1-p24-(gag) | 84 | Posttranslational glycosylation of target proteins implicate molecular mimicry in the pathogenesis of HTLV-1 associated neurological disease. |
| Glycosylation | Virus related diseases | gp 100 | 85 | A glycopolypeptide (gp 100) is the main antigen detected by HTLV-III antisera. |
| Citrullination/deimination | Multiple Sclerosis, Diabetes, Alzheimer's | Myelin basic protein (MBP) | 86 | A tale of two citrullines-structural and functional aspects of myelin basic protein deimination in health and 5 disease. |
| OGlcNAc | Cardiac dysfunction | SP1, eNOS, | 87 | O-GlcNAc modification of nucleocytoplasmic proteins and diabetes. |
| OGlcNAc | Diabetes, Alzheimer's disease | tau, β-amyloid precurssor, AP-3, synapsin-I, Neurofilament H, L, M. IRS, GS, PDX-1, eNOS, SP1 | 88 | O-GlcNAc modification in diabetes and Alzheimer's disease. |
| OGlcNAc | Diabetes | | 89 | A bittersweet modification: O-GlcNAc and cardiac dysfunction. |
| OGlcNAc | Diabetes | Sp1(but also metionned the serum response factor, c-myc, estrogen receptors and RNA pol II) | 90 | PTM by O15 GlcNAc: another way to change protein function. |
| Various PTMs | Atherosclerosis; celiac disease; autoimmune encephalomyelitis; multiple sclerosis; systemic lupus erythematosus; collagen-induced arthritis; rheumatoid arthritis | αB-crystallin, MBP, Fibrin, Type II collagen, MBP Ac1-1, Sm D1, D3, Wheat gliadin, LDL, SnRNP D | 91 | Posttranslational protein modifications: new flavors in the menu of autoantigens. |
| Various PTMs | Multiple sclerosis/EAE, Collagen-induced arthritis, Rheumatoid arthritis, systemic lupus erythematosus. | Fillagrin, Vimentin, H2B | 92 | Posttranslational modifications of self-antigens. |
| Various PTMs | Rheumatoid arthritis; Multiple sclerosis; Systemic lupus erythematosus | trichohyalin, filaggrin and keratin, myelin basic protein(MBP), fibrin, vimentin and nucleophosmin/B23, histones, Sm-D1, Sm-D3, Sm-ByB9, LSm4 | 93 | Modifications of arginines and their role in autoimmunity. |
| Citrullination | Rheumatoid arthritis | Fibrin | 94 | Autoantigenic posttranslational modifications of proteins: does it apply to rheumatoid arthritis? |

The methods of the invention can be applied to identify a set of biomarkers for a disease or medical condition. The set of biomarkers can include information such as the identity of two or more proteins whose level of a given PTM is altered (i.e., either increased, decreased, or modified in terms of the number or position of attached modifying moieties) in the disease or medical condition. The set can be established, for example, by comparing the protein PTM profile of one or more patients having the disease or medical condition with similar profiles from one or more control subjects who do not have the disease or medical condition. The profiles are obtained by separately contacting functional extracts from the patients and control subjects with a microarray containing an ordered plurality of proteins, such as proteins encoded by the human genome, and determining the level of PTM of one or more proteins in the microarray. The presence or absence, or the observed level, of PTM of proteins in the microarray for the patients is then compared with the presence or absence or level of PTM of the corresponding proteins for the control subjects. A set of biomarkers is formed from proteins of the patients whose level of PTM is altered compared to control levels. The biomarker set in some cases can be specific for a certain type of patient sample (e.g., plasma, cerebrospinal fluid, tissue, or cell type). Biomarker sets so identified can be used in any of the methods according to the invention, e.g., in a method of diagnosis.

Methods of the invention can be used to screen for and identify substrates of protein modifying enzymes. For example, a protein microarray containing a set of proteins that include candidate proteins for one or more selected types of PTM can be incubated with a solution containing one or more enzymes that catalyze PTM reactions. The methods described above can be employed to label and identify proteins in the array that serve as substrates for the enzyme(s). Optionally, the array can include variations of one or more protein substrates, e.g., sequence variants or proteins having one or more known modifications at different sites. The array can include only a single protein and its variants, or it can include proteins representative of an entire genome, or proteins expressed by a given cell or tissue, or any subset thereof. Such screening methods can be used to define the specificity of a protein modifying enzyme with respect to protein substrates or with respect to the enzyme recognition sequence, for example, or to analyze signaling pathways.

A further use for the methods of the invention is to characterize the activity of one or more protein modifying enzymes in a functional extract. A functional extract can be analyzed using methods described earlier, while supplementing only with chemical compounds that supply energy for the PTM reaction carried out by a particular enzyme or which serve as cofactors. The protein substrates for the enzyme are supplied in the protein microarray. Further characterization of the functional extract can then be obtained by supplementing it with one or more protein modifying enzymes. Depending on the nature of the signaling pathway, the functional extract can be supplemented with additional enzymes in different combinations in parallel assays. For example, in the case of polyubiquitination, one assay can be performed with the functional extract alone (i.e., no supplementation with exogenous enzymes), another assay can involve the supplementation of the functional extract with an E1 enzyme, and additional assays can involve supplementation with an E1 enzyme plus different combinations of E2 enzymes. In this way a full signaling pathway or any portion thereof can be characterized for a given functional extract using a large number of potential protein substrates by performing only a few reactions.

The invention also includes kits that are useful in practicing the methods presented here, e.g., diagnostic kits. A kit for the diagnosis of a disease or medical condition by the analysis of a PTM state of a protein in a patient sample contains a standard set of one or more functional extracts capable of producing a known pattern of protein PTM states on a protein microarray. Optionally, the kit also contains instructions for carrying out one or more of the methods outlined above. The kit can also optionally contain one or more reagents, such as substrates, co-factors, biochemical agents, buffers, enzymes, enzyme inhibitors, antibodies, or labeling moieties such as fluorophores or radiolabeled compounds. The kit also can include computer software for analysis, one or more protein microarrays, blocking reagents for such microarrays, and packaging material for any of the kit components.

Previous protein-based diagnostic tests typically have assayed the abundance of a protein, and in certain cases its activity. However, the present invention is unique in utilizing functional samples from patients to determine global PTMs or PTM alterations for diagnostics purposes. These methods may serve both for diagnosis of different diseases as described herein, and as a tool for the discovery of new biomarkers and drug targets.

There are many assays available to detect binding interactions, but up to now they have used either dilute protein solutions or detergent-containing cell lysates. The number and strength of the interactions detected are therefore distorted by the change in relative concentration of ligand and target, or by the presence of detergents. In addition, the modification profile can be affected by a change in the relative amounts of, for example, kinase/phosphatase pairs. In the methods according to the present invention, however, undiluted extract (functional extract) can be used without adding detergent, preserving the original physiological state. In addition to examining cytoplasmic fractions, nuclear fractions and smaller organelles can be applied to the microarray as well.

The present methods have far greater dynamic range than available mass spectrometry methods, since thousands of proteins can be spotted on an individual chip in pure form and at high concentration, removing the effect of their relative abundance. Proteins can also be attached to the microarray in different orientations to ensure that binding to different parts of the protein can be detected. The present methods are more straightforward compared to mass spectrometry, and considerably less time-consuming than SDS gels and similar techniques.

As used herein the term "comprising" or "comprises" is used in reference to compositions, methods, and respective component(s) thereof, that are essential to the invention, yet open to the inclusion of unspecified elements, whether essential or not. As used herein the term "consisting essentially of" refers to those elements required for a given embodiment. The term permits the presence of additional elements that do not materially affect the basic and novel or functional characteristic(s) of that embodiment of the invention. The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Example I

Protein Ubiquitination Patterns Upon Escape from the Spindle Assembly Checkpoint in Mammalian Cells Protein microarrays were used to identify the polyubiquitination state of proteins under specific cellular conditions. Highly concentrated cellular extracts that have demonstrable function specific for a particular phase of the cell cycle were used to modify the polyubiquitination state of human proteins on a microarray.

Specifically, the degradation of proteins involved in mitosis was examined by determining the polyubiquitination state of certain proteins at specific stages of the cell cycle. During mitosis, rapid degradation of the mitotic cyclins (11, 12) causes abrupt shut-down of mitotic kinase activity, allowing the cell to enter anaphase. The Anaphase Promoting Complex (APC), a multi-subunit E3 ligase, targets cyclins and other mitotic substrates for proteasomal degradation (13, 14) which in turn leads to the metaphase to anaphase transition. Thus, cell division is highly controlled by the degradation of polyubiquitinted proteins (15).

The experimental strategy was to use nocodazole arrested HeLa S3 functional cytoplasmic extracts and to follow protein polyubiquitination during release from the checkpoint by incubation on protein microarrays by assaying reactivity with labeled antibodies against polyubiquitin chains. Differentially modified proteins were examined in APC-inhibited versus APC-active extracts. The polyubiquitin signature of G1 extracts was also examined.

Tissue Culture and Cell Synchronization

HeLa S3 cells were synchronized in prometaphase by treatment with nocodazole, or in G1 by a release from nocodazole arrest. Cells were incubated in thymidine-containing (2 mM) medium, and then released into fresh medium, followed by a nocodazole arrest (0.1 g/ml). For G1 cells, nocodazole-arrested cells were released into fresh medium for 4 h. Cells were harvested, washed with phosphate buffered saline (PBS), and processed for extraction as described below.

Extract Preparation

HeLa S3 cells were synchronized with thymidine for 20 hours, released for 3 hours, and then arrested in mitosis by the addition of nocodazole for an additional 11 hours. Synchronized cells (CP-extracts) were then harvested, washed with PBS, lysed in Swelling Buffer (25 mM HEPES pH 7.5, 1.5 mM $MgCl_2$, 5 mM KCl, 1 mM dithiothreitol, 1 tablet of Complete protease inhibitors (Roche)), and homogenized by freeze-thawing and passage through a needle. G1-extracts were prepared in the same manner with an additional 4 hour release from nocodazole arrest. Extracts were cleared by subsequent centrifugation (5 min at 5,000 r.p.m. followed by 60 min at 14,000 r.p.m.). Extract (20 μl) was supplemented with Degradation Cocktail (1 μL) containing 1.5 mg/ml ubiquitin (Boston Biochem), 150 mM creatine phosphate, 20 mM ATP (pH 7.4), 2 mM EGTA (pH 7.7), 20 mM $MgCl_2$).

Incubation of Extracts with Microarrays

Human PROTO-ARRAY® microarrays (Invitrogen) were washed three times (10 min each) with TBS containing 0.05% Tween 20 (TBS-T) and then blocked for 4 hours at 4° C. with microarray blocking solution (ARRAYIT® brand BLOCKIT™ (TeleChem International, Inc.)). Extracts were pre-incubated with either Emi1 (1 mg/ml) or $H_20$ for 30 minutes. 100 μl of CP or G1 extracts (~25 mg/nil) were then supplemented with UbcH10 (5 μl, 1 mg/ml; Boston Biochem) and incubated under a coverslip on the microarrays for 1 hour at RT. The arrays were then washed and incubated overnight with anti-polyubiquitin antibody (FK1, 1 mg/ml; Biomol) diluted 1:250. To label modified (polyubiquitinated) proteins, an anti-mouse Cy3-conjugated secondary antibody (3 μl; 1 mg/ml, Jackson ImmunoResearch Laboratories) was incubated for 1 hour at RT. The arrays were washed again, spin-dried (200 g, 5 min) and scanned with a GenePix 4000B scanner.

Images and Data Processing

Figure 10A:
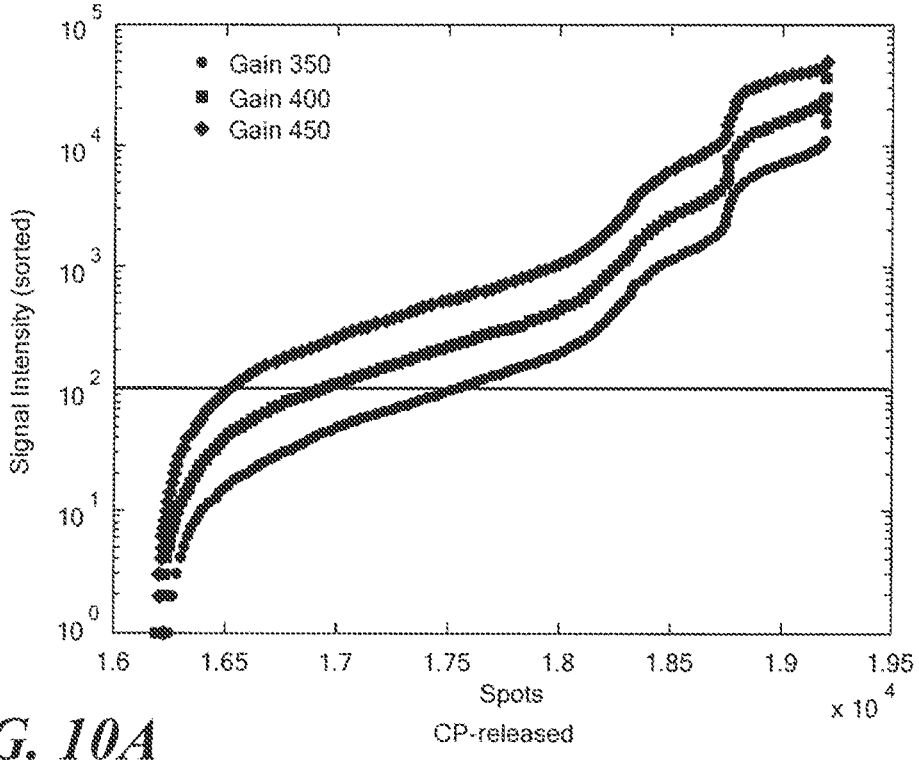
FIGS. 10A and 10B show the signal intensity distribution of all the spots on a protein microarray.
Figure 10B:
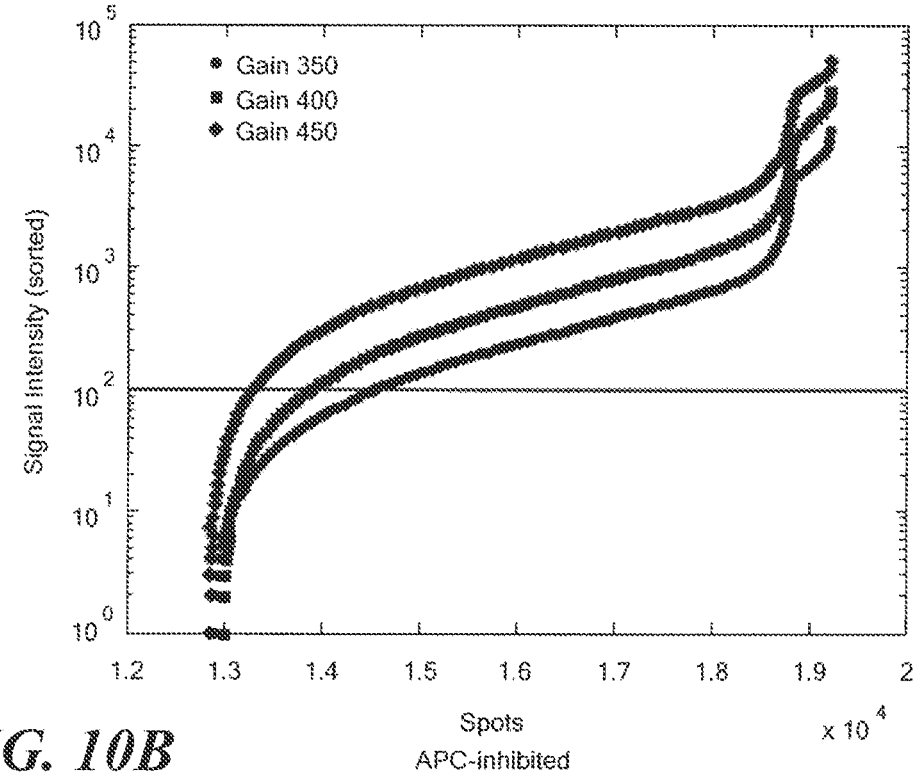

Results were recorded as TIFF files and images were quantified using Gene Pix Pro 5 feature extraction software (version 4000B). Scanning parameters were set so that none of the spots showed saturation: PMT gain value=400; laser power=30% (see FIG. 10). For each spot, the local background intensity was subtracted from the median spot intensity.

Data Filtering and Normalization

The processed data set was organized in a matrix where each column contains the reactivities measured for a given array and each row contains the reactivities measured for a given protein over all arrays. The negative values were set to zero and the data was then normalized using the quantile normalization algorithm (32).

Data Analysis

To determine subsets of proteins that were differentially modified on the different microarrays a two-sample t-test was used. Each protein was tested separately by comparing its signal intensity values in two different conditions (2 replicates per chip; 2 chips for each tested condition). Thus four signal intensities were measured for each protein and each condition. 1000 permutations were performed (within rows, i.e., all values for each protein were shuffled) and permutation-based p-values were calculated based on the new t-scores. P-values lower than 0.01 were considered significant.

Degradation Assays

Coupled in vitro transcription and translation were performed from pCS2+ constructs using a rabbit reticulocyte lysate system (TnT SP6, Promega) or wheat germ extracts. $^{35}$S-labelled substrates were added to G1 or CP extracts of synchronized HeLa S3 cells (see extract preparation). Aliquots were removed at 0, 30, 60, and 90 min and analyzed by SDS-PAGE (4-15%) and autoradiography. Additionally, endogenous protein levels (actin (Sigma), securin (Mb1), calmodulin (Upstate), and p27 (Upstate)) were determined in the extracts by Western blotting at the indicated times.

Results

The E2-conjugating enzyme, UbcH10, has been shown to overcome the metaphase-anaphase transition (16). After arresting cells in nocodazole, concentrated extracts (apprx 25 mg/ml) were made and these retain the checkpoint state (CP extracts). It is known that addition of UbcH10 to a concentration of 5 uM (approx. 25 mg protein/ml) to nocodazole-arrested, concentrated cell extracts inactivates the metaphase state and leads to APC-dependant substrate degradation (17).

Figure 2A:
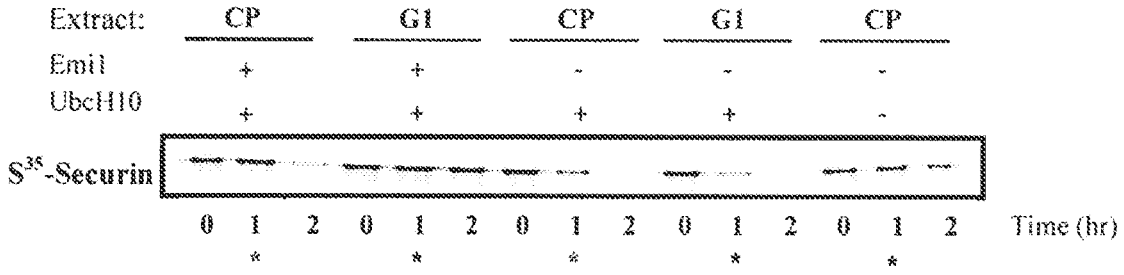
FIG. 2A shows the degradation of $^{35}$S-labeled securin, added as a control to functional extracts, as a function of time at selected points during the cell cycle. The reactions were stopped at the indicted times by the addition of sample buffer and were then analyzed by SDS-PAGE and autoradiography. The star (*) labeled lanes reflect the state of the extracts at the time when incubation on the protein microarrays were stopped.
Figure 2B:
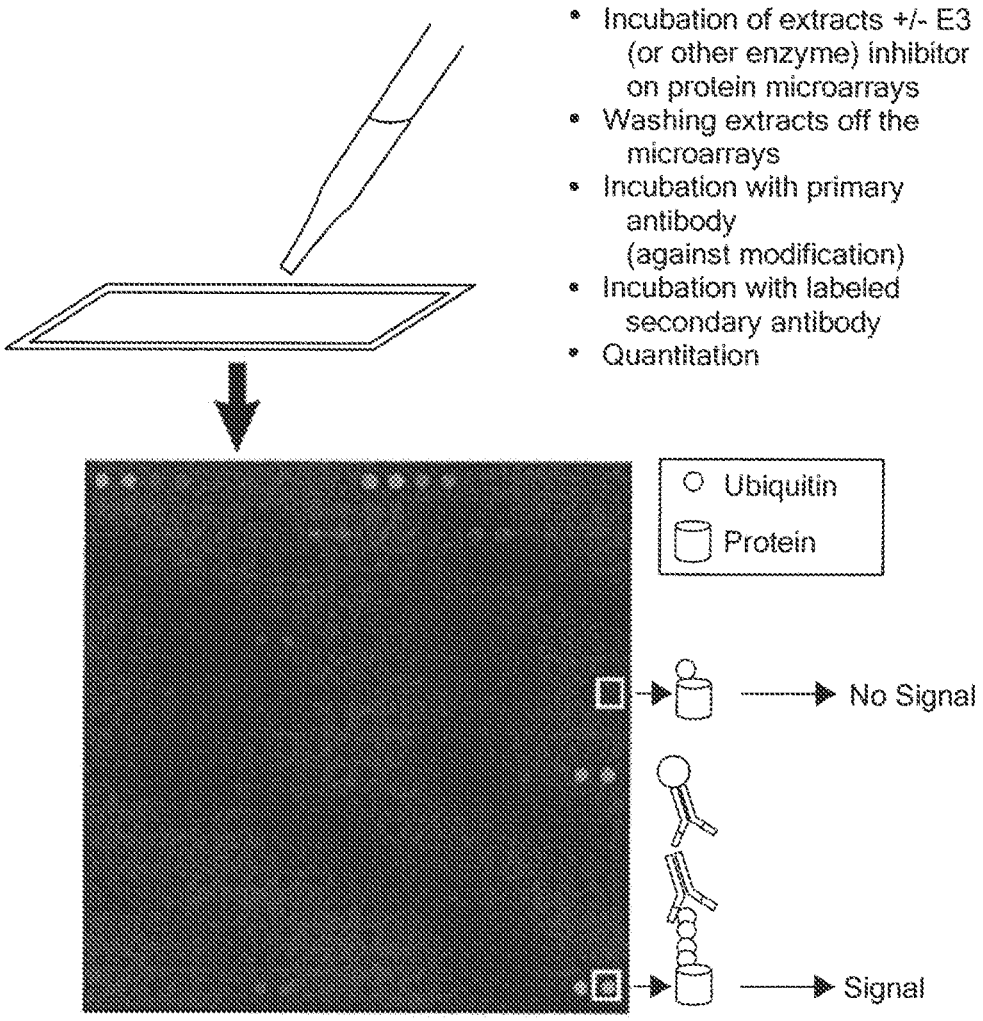
FIG. 2B is a schematic illustration of the use of a protein microarray for the detection of posttranslational modifications. An example of one block/subarray out of the 48 on each chip is given (16 rows×16 columns).
Figure 2C:
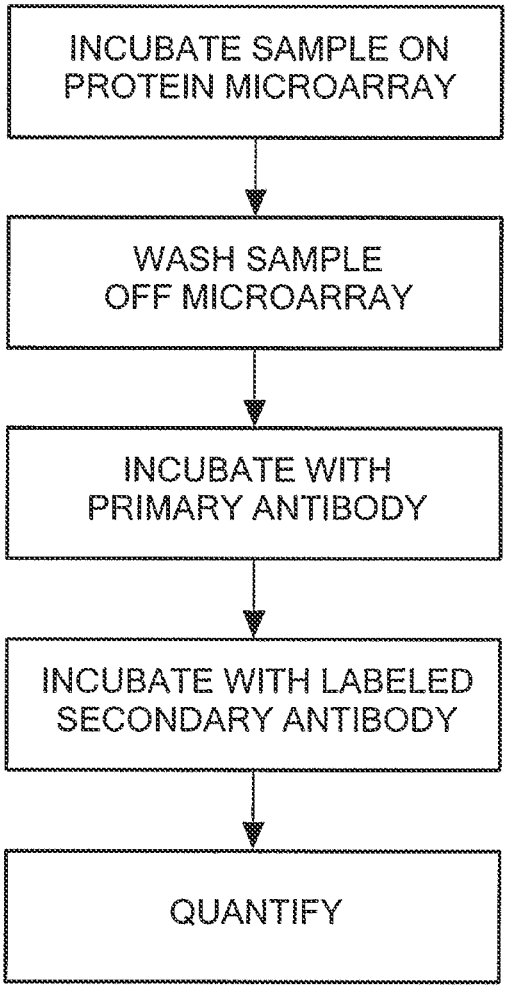
FIG. 2C is a schematic description of the steps of using a protein microarray for the detection of PTMs and PTM alterations.
Figure 5A:
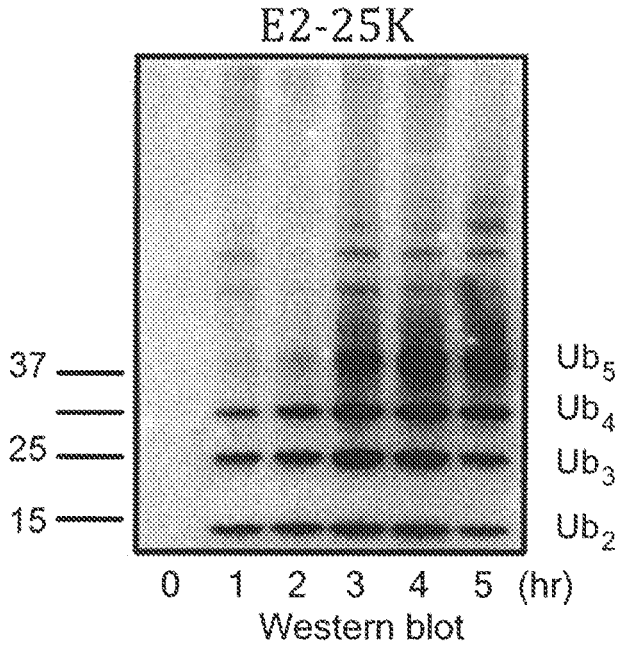
FIGS. 5A and 5B show the results of experiments to test the recognition of polyubiquitinated proteins with FK1 antibody.
Figure 5B:
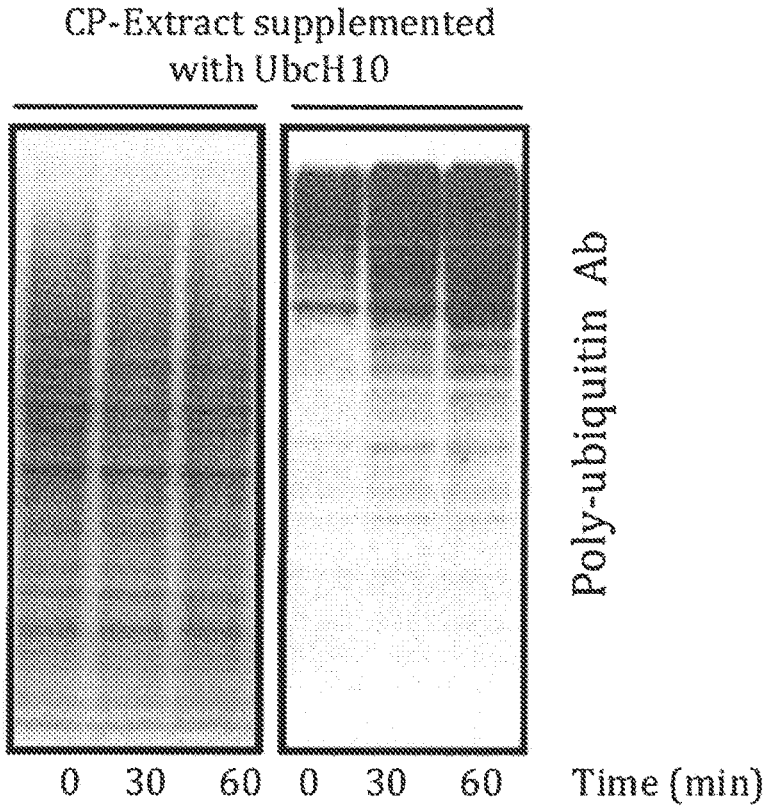

Extracts were prepared from synchronized HeLa S3 cells arrested in mitosis or in G1. CP extracts were divided into three aliquots; one was retained, one was supplemented with UbcH10, and the third received UbcH10 and an inhibitor of APC, emi1. The samples were placed on the protein microarray for 60 minutes at room temperature (FIG. 2B). In order to control for the activity of the extracts, an aliquot of each sample was removed and $^{35}S$ labeled-securin, a well-characterized APC substrate, was added to record its degradation (FIG. 2A). Securin remained stable in CP extracts even after 60 minutes at room temperature (FIG. 2A, right panel) which is consistent with the inhibition of APC by the spindle checkpoint. CP extract supplemented with UbcH10 (CP-released) degraded securin rapidly while the addition of the APC inhibitor Emi1 (APC-inhibited) stabilized securin for at least sixty minutes. To label modified proteins on the arrays, an anti-polyubiquitin antibody (FK1) was used (FIG. 5) with a Cy3-conjugated secondary antibody. Microarrays were then scanned and the median signal intensity and local background of each spot was measured. FIG. 2B illustrates the process and depicts one representative scanned subarray (out of 48 on each chip) and its reactivity.

Figure 3A:
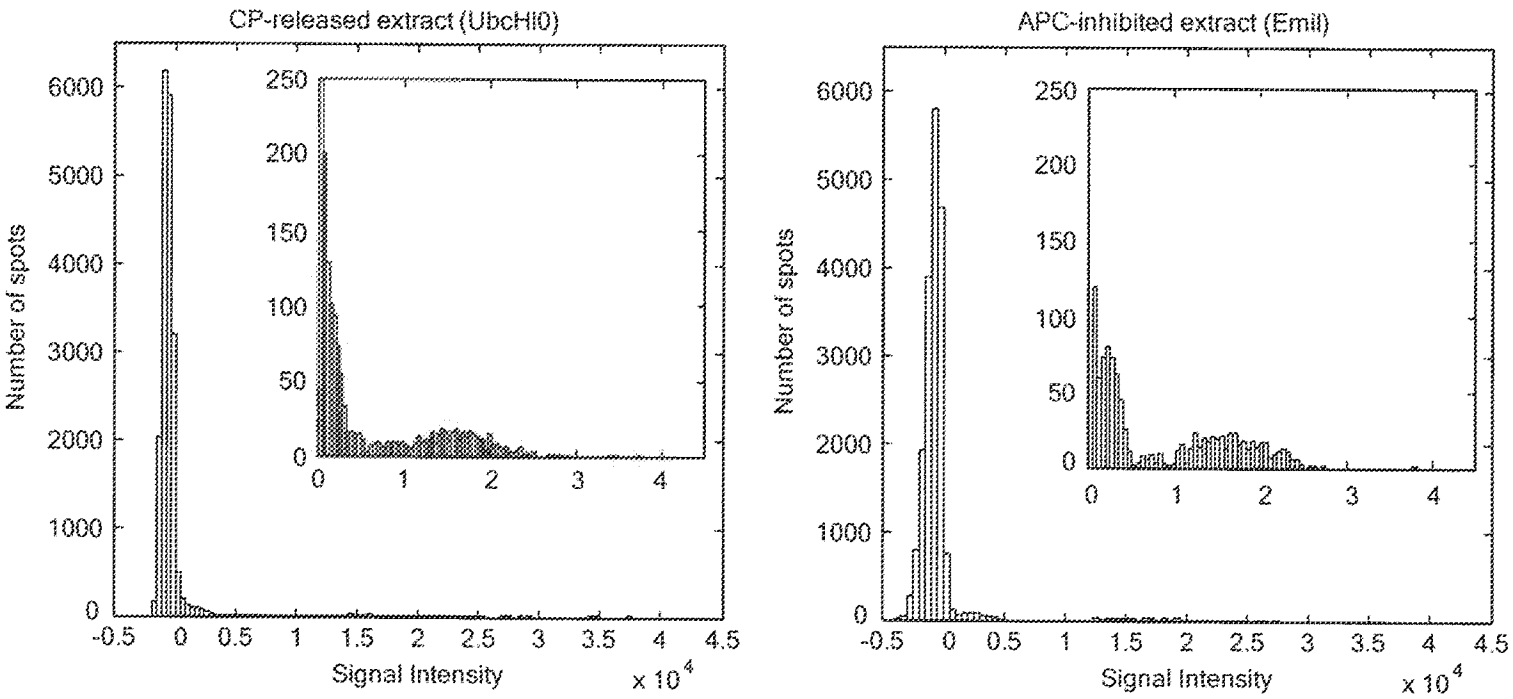
FIG. 3A shows the distribution of signal intensity minus background values of all the spots on a protein microarray after detection of polyubiquitinated proteins. Reactivities were divided into 100 equally-sized bins, and the number of spots (y-axis) at different intensity levels (x-axis) of CP-released (left) and APC-inhibited (right) cell extracts was plotted. The inset represents a 20× magnification of the positive signals where the y-axis ranges between 0 and 250 and the x-axis ranges between 0 and 45,000.
Figure 6:
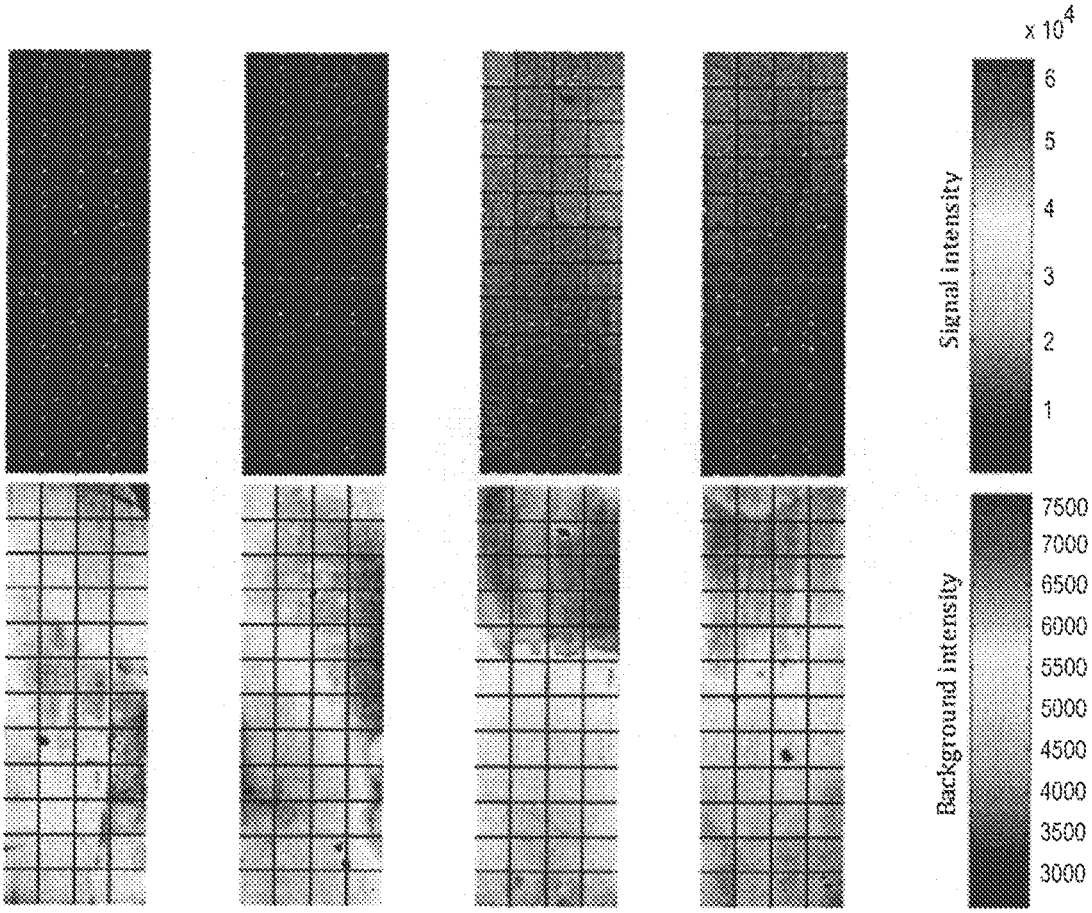
FIG. 6 shows the distribution of signal and background levels observed on four representative protein microarrays.
Figure 7:
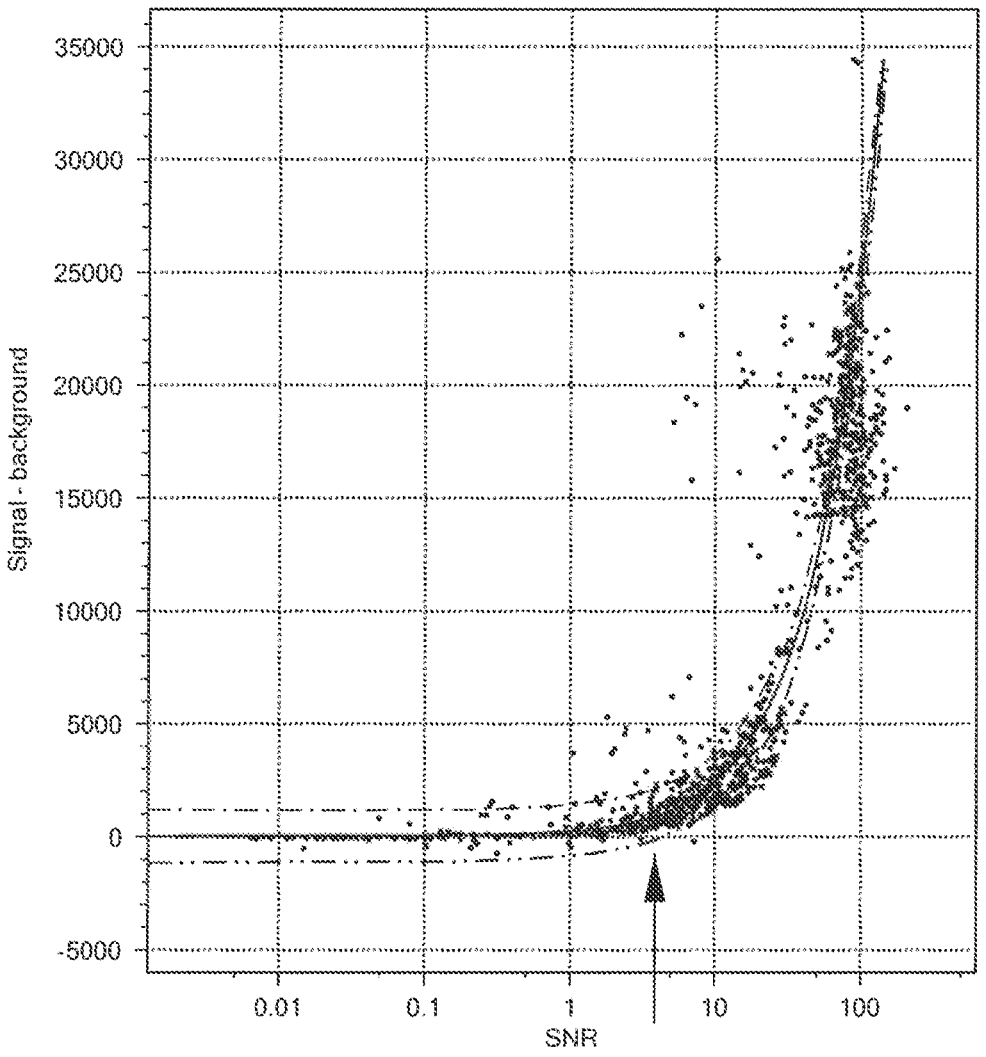
FIG. 7 shows the signal-to-noise ratio for all spots on a protein microarray chip.

Most of the spots in the microarray revealed a signal of low intensity or similar to the background level. Only 9-11% of the spots on each chip gave a positive signal after subtracting the local background intensity. FIG. 3A shows the distribution of the data of two representative chips under the CP-released (left panel) and APC-inhibited condition (right panel); the inset depicts the positive signal reactivity that was detected. A commonly accepted criterion for determining minimum signal (threshold) that can be accurately quantified is the measure of Signal to Noise Ratio (SNR) where a higher SNR indicates higher signal over background noise; a signal-to-noise ratio of 3 is commonly considered the lower limit for accurate detection. Thus, the SNR ratio for every spot on the chip was calculated as follows: SNR=(signal mean−background mean)/(standard deviation of the background) (18). Even though the background signal within each microarray was variable (FIG. 6), the SNR per spot revealed a clear signal (SNR>3) even for spots with a low signal intensity of about 1500 units (FIG. 7).

Figure 3B:
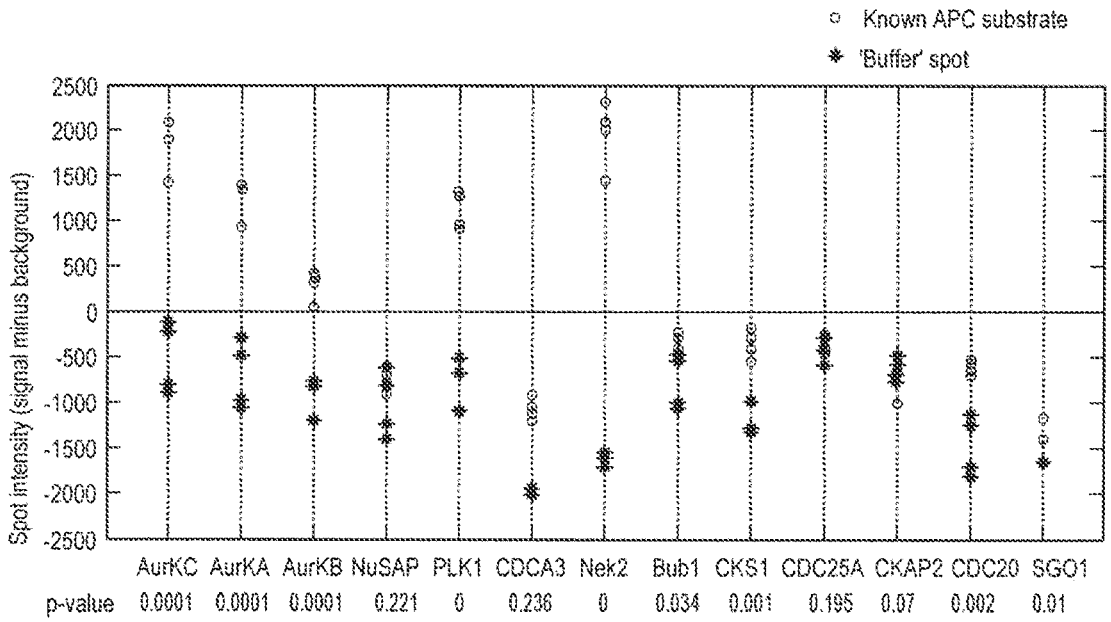
In FIG. 3B the reactivity level of 13 known APC substrates (dots) was compared to the reactivity level of the 'buffer' spots located in the same subarray (stars). The reactivities were then compared using a two-sample t-test to determine their significance, and the p-values were labeled below each substrate.
Figure 8:
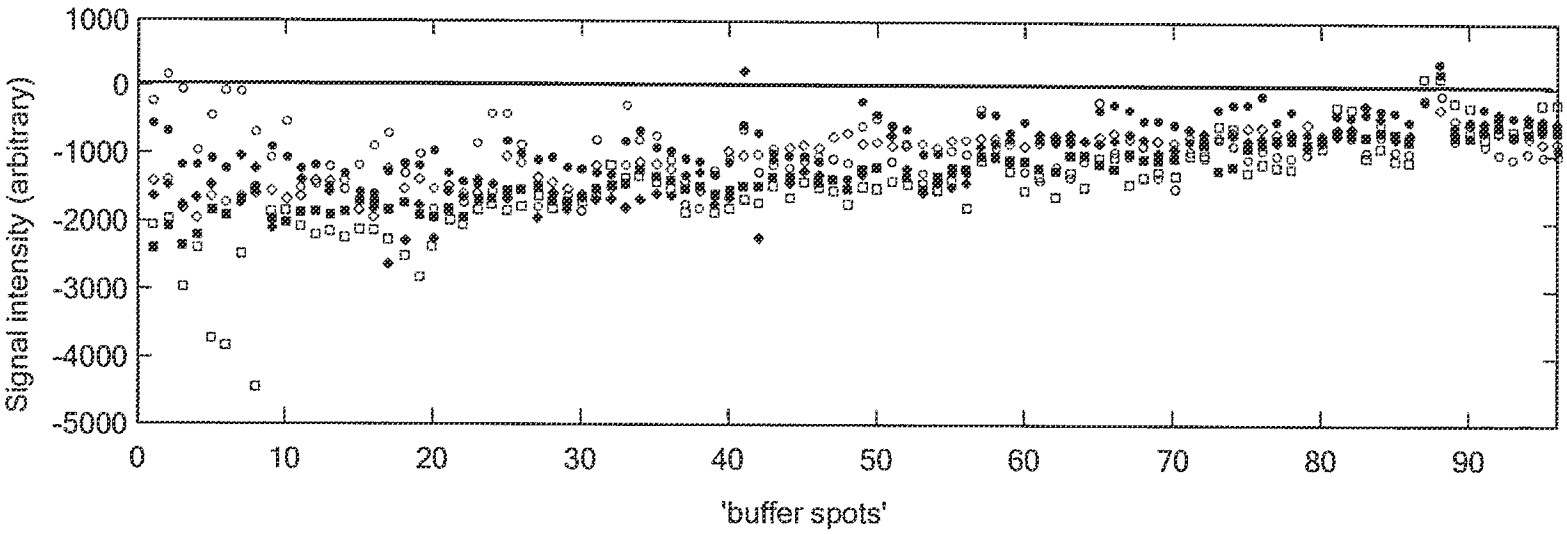
FIG. 8 shows the signal-background values for the buffer spots on five representative protein microarrays.
Figure 9:
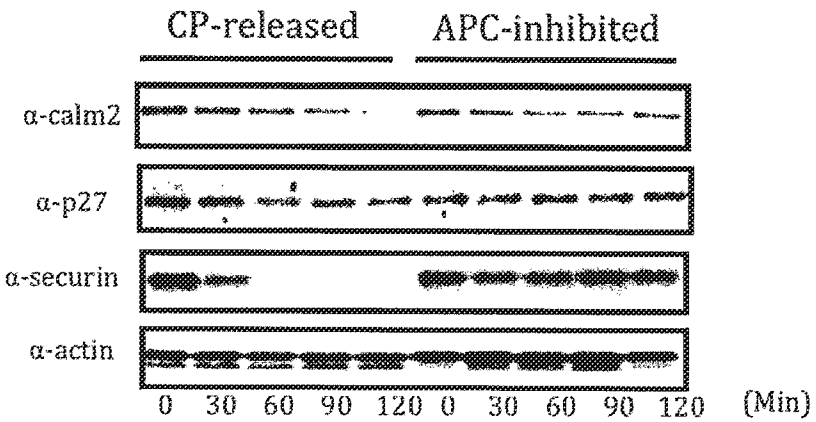
FIG. 9 shows the levels of the indicated endogenous proteins in functional extracts as a function of time as detected by Western blotting.

The threshold level defining a significant polyubiquitination signal was determined using the signal from 96 'buffer' spots on each microarray. When subtracting the local background from the signal, 99% of the buffer spots on each chip gave a negative value (mean value of −1130; see FIG. 8). The signal of thirteen known APC substrates was determined on each chip was compared with the signal of the 'buffer' spots located adjacent to them (i.e., in the same subarray). As shown in FIG. 3B, nine of these substrates appeared to have a signal that was significantly higher than the buffer spots ($p<0.05$) but only five of them gave a positive signal. In order to reduce the potential false positive rate, only positive values were considered as reflecting real modification signals in this study.

Figure 3C:
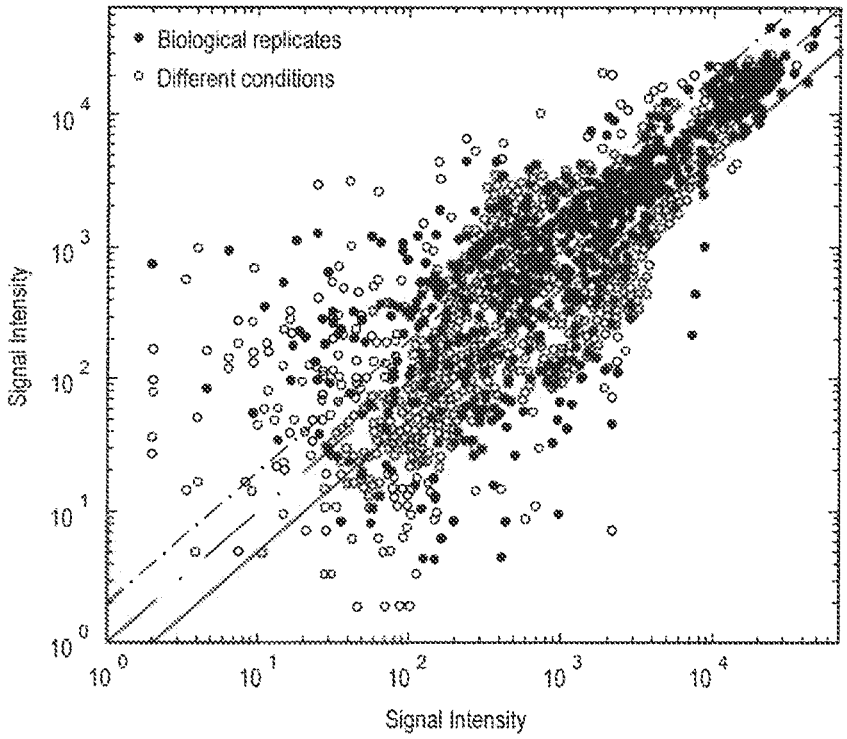
FIG. 3C shows scatter plots of the positive signal intensities on each chip. The plots show the variability between two biological replicates (black dots; x-axis: CP-released, y-axis: CP-released) vs. the variability between signals from two different conditions (red dots; x-axis: APC-inhibited, y-axis: CP-released).
Figure 4A:
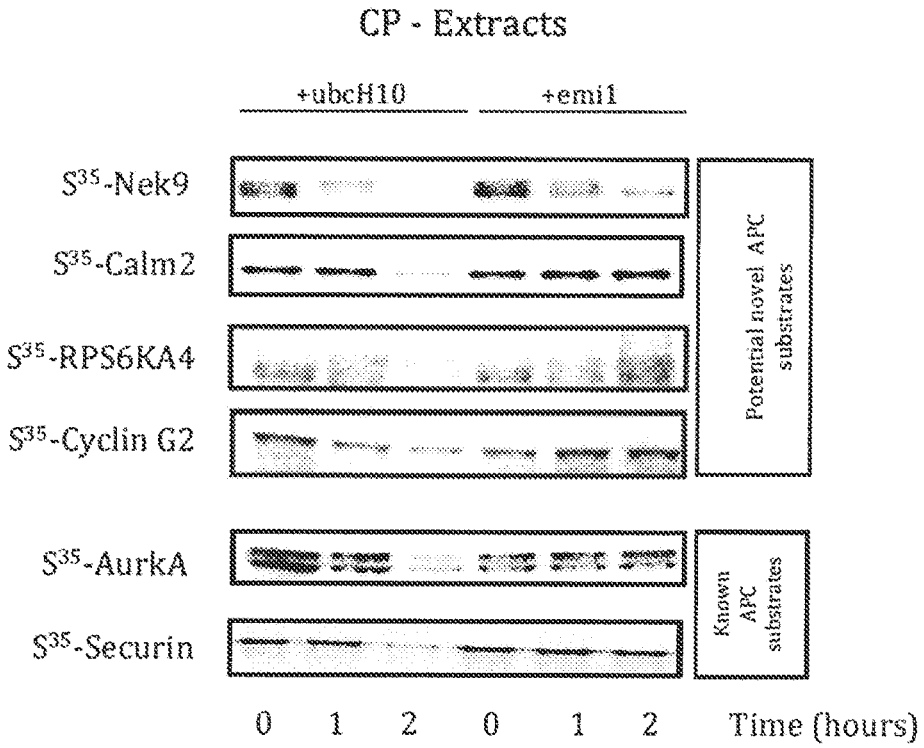
FIG. 4A shows analysis by SDS-PAGE (4-15% gels) and autoradiography of $^{35}$S-labelled substrates (Nek9, Calm2, RPS6KA4 and cyclin G2) added to CP synchronized HeLa S3 extracts with and without the addition of the APC-inhibitor emi1.
Figure 4B:
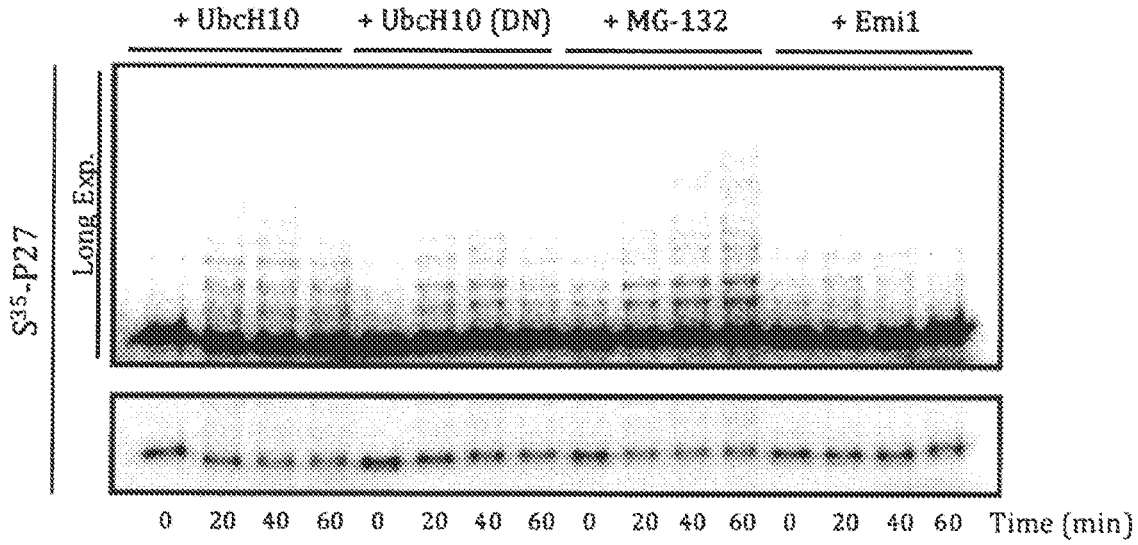
FIG. 4B shows a similar analysis in which $^{35}$S-labelled p27 was added to CP synchronized HeLa S3 extracts with the addition of UbcH10, DN-UbcH10, or MG-132, or Emi1; the bottom panel shows the change in stability of p27 under this condition. The top panel is the same gel exposed for 4 days (long exposure) to detect p27-conjugated ubiquitin chains.

To test the reproducibility of the assay and its ability to detect differential PTMs between different conditions, microarrays that were incubated with different extract preparations (biological replicates) were compared, and microarrays with extracts under different conditions (CP released vs. APC-inhibited) were also compared. FIG. 3C depicts the scatter plots of the positive spot reacitivities in each comparison (log scale). Visually the two different conditions (red dots) produced a signal that was more spread and variable compared to the biological replicates (black dots), which are closer to the diagonal. These distributions differ very significantly by statistical tests. Two microarrays were compared from each condition, and the p-value of the differences between corresponding proteins (each comprised of 4 spots) was calculated using a two-sample t-test. To control for the multiple hypothesis testing, the p-value determination was based on 1000 permutations (per protein) of the data. More than a hundred proteins yielded a significant p-value ($p<0.01$); these proteins are listed in Table 4. While these proteins varied greatly in their attributed functions and cellular processes, several known APC substrates are among the significantly detected proteins, including all three aurora kinases. Given the state of knowledge of APC substrates it was to be expected that some new substrates should have been detected by this approach. Five proteins (Nek9, Calm2, RPS6KA4, cyclin G2 and p2'7) that were detected as differentially modified in these microarrays had previously been reported to play a role in mitosis. These five proteins, together with two proteins (Zap-70 and MAP3K11) that were not previously shown to be involved in mitosis, were selected for a biochemical assay to test their ability to serve as APC substrates. Zap-70 and MAP3K11 showed no detectable ubiquitination or degradation in the biochemical assay for mitosis dependent degradation. It should be noted that not all substrates would be expected to score in such an assay, due to lack of cofactors, poor folding, lack of post-translational modification, or other factors, and therefore a negative result is not dispositive. However, Nek9, Calm2, RPS6KA4 and cyclin G2 proteins were found to be degraded in the CP extracts, and their degradation was inhibited by the addition of emi1 (FIG. 4A). Interestingly, p27 appeared to be degraded in the CP-released extracts as well; however, a longer exposure (FIG. 4B) revealed that the protein accumulated polyubiquitin chains (causing a gel shift) and was not rapidly degraded (compare with the addition of the proteasome inhibitor MG-132). While the addition of emi1 did not inhibit completely the formation of ubiquitin chains, it appeared to yield a lower signal then seen in the CP-released extract; this conjugation might have occurred during the pre-incubation of the emi1 with the extracts. The endogenous level of calm2 and p27 in CP-released and APC-inhibited extracts was examined by Western blot. Both p27 and calm2 were degraded in the extracts from cells released into an anaphase-like state, and their degradation was inhibited by the addition of emi1.

TABLE 4

| Protein Name | Accession | p-value |
|---|---|---|
| histone UNFRAC. WHOLE HISTONE - known Autoantigen | | 0.0002 |
| ring finger protein 128 (RNF128) transcript variant 1 | NM_194463.1 | 0.0004 |
| erythrocyte membrane protein band 4.1 like 5 | BC054508.1 | 0.0004 |
| BC013173 *Homo sapiens*, clone MGC: 17340 | BC013173.1 | 0.0004 |
| Clmodulin 2 | NM_001743 | 0.0005 |
| HTGN29 protein (HTGN29) | NM_020199.1 | 0.0006 |
| ankyrin repeat domain 13 | BC032833.2 | 0.0006 |
| ribosomal protein S6 kinase 90 kDa polypeptide 4 (RPS6KA4) transcript variant 2 | NM_001006944.1 | 0.0007 |
| macrophage stimulating 1 receptor (c-met-related tyrosine kinase) (MST1R) | NM_002447.1 | 0.0008 |
| hypothetical protein FLJ11184 | BC011842.2 | 0.0008 |
| PCTAIRE protein kinase 2 | BC033005.1 | 0.0008 |

TABLE 4-continued

| Protein Name | Accession | p-value |
|---|---|---|
| aurora kinase A (AURKA) transcript variant 2 | NM_003600.2 | 0.0009 |
| dolichyl-phosphate mannosyltransferase polypeptide 2 regulatory subunit (DPM2) transcript variant 2 | NM_152690.1 | 0.0009 |
| ems1 sequence (mammary tumor and squamous cell carcinoma-associated (p80/85 src substrate) (EMS1) | NM_138565.1 | 0.0009 |
| cytochrome P450 family 26 subfamily A polypeptide 1 (CYP26A1) transcript variant 2 | NM_057157.1 | 0.0010 |
| KIAA0157 protein (KIAA0157) | NM_032182.2 | 0.0010 |
| solute carrier family 23 (nucleobase transporters) member 2 | BC013112.2 | 0.0011 |
| ring finger protein 111 | BC060862.1 | 0.0011 |
| additional sex combs like 1 (*Drosophila*) | BC064984.1 | 0.0012 |
| cDNA clone MGC: 39273 IMAGE: 5440834 | BC024289.1 | 0.0012 |
| PAS domain containing serine/threonine kinase (PASK) | NM_015148.1 | 0.0013 |
| YY1 transcription factor (YY1) | NM_003403.3 | 0.0013 |
| proteasome (prosome macropain) 26S subunit non-ATPase 4 (PSMD4) transcript variant 1 | NM_002810.1 | 0.0014 |
| hypothetical protein LOC143458 (LOC143458) | NM_174902.2 | 0.0014 |
| selectin ligand interactor cytoplasmic-1 (SLIC1) transcript variant 1 | NM_153337.1 | 0.0015 |
| MAX interacting protein 1 (MXI1) transcript variant 2 | NM_130439.1 | 0.0015 |
| neural precursor cell expressed developmentally down-regulated 8 (NEDD8) | NM_006156.1 | 0.0016 |
| aurora kinase B (AURKB) | NM_004217.2 | 0.0016 |
| src homology three (SH3) and cysteine rich domain | BC020221.1 | 0.0016 |
| hypothetical protein DKFZp762O076 (DKFZp762O076) | NM_018710.1 | 0.0016 |
| Nedd4 family interacting protein 1 (NDFIP1) | NM_030571.2 | 0.0016 |
| hypothetical protein FLJ36175 | BC029520.1 | 0.0017 |
| EGF-like repeats and discoidin I-like domains 3 | BC053656.1 | 0.0018 |
| hypothetical protein MGC4618 (MGC4618) | NM_032326.1 | 0.0019 |
| zeta-chain (TCR) associated protein kinase 70 kDa (ZAP70) transcript variant 1 | NM_001079.3 | 0.0019 |
| ribosomal protein L30 (RPL30) | NM_000989.2 | 0.0019 |
| feline sarcoma oncogene (FES) | NM_002005.2 | 0.0019 |
| met proto-oncogene (hepatocyte growth factor receptor) (MET) | NM_000245.2 | 0.0021 |
| ADP-ribosylation factor-like 7 (ARL7) | NM_005737.3 | 0.0022 |
| Histone_F2a2 H2a(f2a2) - known Autoantigen | | 0.0022 |
| likely ortholog of mouse gene trap locus 3 (GTL3) | NM_013242.1 | 0.0022 |
| immediate early response 3 (IER3) transcript variant short | NM_003897.2 | 0.0023 |
| potassium voltage-gated channel shaker-related subfamily beta member 2 (KCNAB2) | NM_003636.1 | 0.0023 |
| immunoglobulin heavy constant gamma 1 (G1m marker) | BC014667.1 | 0.0024 |
| ring finger protein 4 (RNF4) | NM_002938.2 | 0.0025 |
| proteasome (prosome macropain) 26S subunit non-ATPase 4 (PSMD4) transcript variant 2 | NM_153822.1 | 0.0026 |
| chromosome 6 open reading frame 145 (C6orf145) | NM_183373.2 | 0.0027 |
| neurotrophic tyrosine kinase receptor type 1 (NTRK1) transcript variant 3 | NM_001007792.1 | 0.0028 |
| pleckstrin homology domain containing family G member 5 (PLEKHG5) transcript variant 1 | NM_020631.2 | 0.0028 |
| Sjogren syndrome antigen A1 (52 kDa ribonucleoprotein autoantigen SS-A/Ro) (SSA1) | NM_003141.2 | 0.0028 |
| interferon stimulated gene 20 kDa (ISG20) | NM_002201.3 | 0.0028 |
| WD repeat domain 45 (WDR45) transcript variant 1 | NM_007075.3 | 0.0029 |
| TANK-binding kinase 1 (TBK1) | NM_013254.2 | 0.0029 |
| chromosome 16 open reading frame 5 | BC002882.1 | 0.0030 |
| insulin-like growth factor 1 receptor (IGF1R) | NM_000875.2 | 0.0030 |
| ring finger protein 111 | BC010369.1 | 0.0031 |
| G protein-coupled receptor kinase 4 (GRK4) transcript variant 2 | NM_001004056.1 | 0.0032 |
| v-yes-1 Yamaguchi sarcoma viral related oncogene homolog (LYN) | NM_002350.1 | 0.0033 |
| RAS-like family 10 member B | BC041133.1 | 0.0034 |
| hypothetical protein MGC11257 (MGC11257) | NM_032350.3 | 0.0035 |
| chromosome 7 open reading frame 2 (C7orf2) | NM_022458.2 | 0.0035 |
| expressed in T-cells and eosinophils in atopic dermatitis (ETEA) | NM_014613.1 | 0.0036 |
| mitogen-activated protein kinase kinase kinase 11 (MAP3K11) | NM_002419.2 | 0.0036 |
| casein kinase 1 alpha 1 (CSNK1A1) transcript variant 1 | NM_001025105.1 | 0.0038 |
| zeta-chain (TCR) associated protein kinase 70 kDa transcript variant 1 | BC053878.1 | 0.0038 |
| hypothetical gene LOC128439 (LOC128439) | NM_139016.2 | 0.0038 |
| hypothetical protein MGC17403 (MGC17403) | NM_152634.1 | 0.0039 |
| N-glycanase 1 (NGLY1) | NM_018297.2 | 0.0039 |
| signal recognition particle 19 kDa | BC010947.1 | 0.0040 |
| DNA fragmentation factor 40 kDa beta polypeptide (caspase-activated DNase) (DFFB) transcript variant 3 | NM_001004285.1 | 0.0040 |
| casein kinase 1 delta (CSNK1D) transcript variant 1 Not full-length. | NM_001893.3 | 0.0042 |
| dendritic cell-derived ubiquitin-like protein (DC-UbP) | NM_152277.1 | 0.0043 |
| cDNA clone MGC: 3432 IMAGE: 2959461 | BC013957.1 | 0.0043 |
| DnaJ (Hsp40) homolog subfamily B member 12 (DNAJB12) transcript variant 1 | NM_001002762.1 | 0.0043 |
| solute carrier family 36 (proton/amino acid symporter) member 4 | BC047374.1 | 0.0044 |
| SMT3 suppressor of mif two 3 homolog 1 (yeast) (SUMO1) transcript variant 1 | NM_003352.4 | 0.0044 |
| similar to hypothetical protein FLJ25555 | BC044239.1 | 0.0049 |
| lysosomal-associated protein transmembrane 4 alpha (LAPTM4A) | NM_014713.2 | 0.0050 |
| KIAA1458 protein | BC031691.2 | 0.0051 |
| interleukin 17E (IL17E) transcript variant 1 | NM_022789.2 | 0.0053 |
| serum/glucocorticoid regulated kinase (SGK) | NM_005627.1 | 0.0053 |
| hypothetical protein FLJ10156 | BC005004.1 | 0.0054 |
| thousand and one amino acid protein kinase (TAO1) | NM_004783.1 | 0.0054 |
| ADP-ribosylation-like factor 6 interacting protein 4 (ARL6IP4) | NM_016638.1 | 0.0054 |
| zinc finger protein 313 (ZNF313) | NM_018683.2 | 0.0055 |

TABLE 4-continued

| Protein Name | Accession | p-value |
|---|---|---|
| solute carrier family 6 (neurotransmitter transporter) member 15 | BC022253.1 | 0.0055 |
| XM_378350.2 | XM_378350.2 | 0.0057 |
| low density lipoprotein receptor-related protein 10 (LRP10) | NM_014045.1 | 0.0060 |
| arrestin domain containing 3 (ARRDC3) | NM_020801.1 | 0.0062 |
| cyclin-dependent kinase inhibitor 1B (p27 Kip1) (CDKN1B) | NM_004064.2 | 0.0062 |
| p53-regulated DDA3 (DDA3) | NM_032636.2 | 0.0065 |
| calcium/calmodulin-dependent protein kinase IV (CAMK4) | NM_001744.2 | 0.0066 |
| BC015569 *Homo sapiens*, Similar to SRp25 nuclear protein | BC015569.1 | 0.0066 |
| chromosome 6 open reading frame 201 (C6orf201) | NM_206834.1 | 0.0067 |
| tripartite motif-containing 52 (TRIM52) | NM_032765.1 | 0.0067 |
| hypothetical protein FLJ38628 (FLJ38628) | NM_152267.2 | 0.0071 |
| vasopressin-induced transcript | BC000877.1 | 0.0074 |
| Ro-52 Ro-52 - known Autoantigen | | 0.0074 |
| cyclin G2 | BC032518.1 | 0.0076 |
| mitogen-activated protein kinase kinase 6 (MAP2K6) transcript variant 2; mutant protein: MAP2K6 mutant | NM_031988.1 | 0.0077 |
| conserved helix-loop-helix ubiquitous kinase (CHUK) | NM_001278.3 | 0.0078 |
| aurora kinase C (AURKC) transcript variant 1 | NM_001015878.1 | 0.0079 |
| dual-specificity tyrosine-(Y)-phosphorylation regulated kinase 3 (DYRK3) transcript variant 2 | NM_001004023.1 | 0.0080 |
| cullin 3 (CUL3) | NM_003590.2 | 0.0080 |
| hepatocyte growth factor-regulated tyrosine kinase substrate (HGS) | NM_004712.3 | 0.0084 |
| B lymphoid tyrosine kinase (BLK) | NM_001715.2 | 0.0084 |
| hypothetical protein MGC40579 (MGC40579) | NM_152776.1 | 0.0086 |
| NIMA (never in mitosis gene a)-related kinase 9 (NEK9) | NM_033116.2 | 0.0086 |
| solute carrier family 1 member 1 (SLC1A1) nuclear gene encoding mitochondrial protein | NM_004170.2 | 0.0086 |
| *Homo sapiens*, SWI/SNF related, matrix associated, actin dependent regulator of chromatin, subfamily d, member 2 | BC018953.1 | 0.0086 |
| calcium binding protein 4 | BC033167.1 | 0.0088 |
| chromosome 19 open reading frame 28 (C19orf28) | NM_174983.2 | 0.0088 |
| ubiquitin-activating enzyme E1-like (UBE1L) | NM_003335.2 | 0.0090 |
| regenerating islet-derived 1 alpha (pancreatic stone protein pancreatic thread protein) | BC005350.1 | 0.0090 |
| DnaJ (Hsp40) homolog subfamily B member 6 transcript variant 2 | BC000177.2 | 0.0091 |
| calcium/calmodulin-dependent protein kinase (CaM kinase) II beta (CAMK2B) transcript variant1 | NM_001220.3 | 0.0093 |
| ubiquitin-conjugating enzyme E2-like | BC064566.1 | 0.0094 |
| melanoma antigen family B 1 (MAGEB1) | NM_002363.1 | 0.0097 |
| secretory carrier membrane protein 3 (SCAMP3) transcript variant 1 | NM_005698.2 | 0.0097 |
| hypothetical protein LOC255330 | BC042038.1 | 0.0099 |

Example II

Ubiquitination of Human Brain Proteins in Alzheimer's Disease

Human brain specimens are collected from deceased human subjects at autopsy after obtaining informed consent from the next of kin under protocols approved by the Partners Human Research Committee at Brigham and Women's Hospital. Weighed frozen human temporal or frontal cortices containing white and gray matter are added to freshly prepared, ice-cold TBS (20 mM Tris-HCl, 150 mM NaCl, pH 7.4) at a ratio of 4:1 (TBS volume/brain wet weight) and homogenized with 25 strokes at a setting of 10 on a mechanical Dounce homogenizer. The homogenate is centrifuged at 175,000×g in a TLA100.2 rotor on a Beckman TL 100 centrifuge, and then the supernatant is aliquoted and stored at −80° C.

For analysis of ubiquitination, samples are thawed on ice, supplemented with 5 μM ubiquitin, 2 mM ATP, and 150 mM creatine phosphate, and then incubated on a microarray to carry out the ubiquitination reaction. Optionally, E1 and/or E2 enzymes can be added to the extract, to determine if they are limiting the ubiquitination reaction.

Example III

Protein Ubiquitination in Cerebrospinal Fluid (CSF) from a Patient with Brain Tumor Undiluted CSF from a patient with brain tumor was analyzed for enzyme activity responsible for PTM (ubiquitination) of human proteins. Conditions were similar to conditions used for cellular extracts. An ATP regenerating system and ubiquitin were added to the CSF sample, and the mixture was reacted with a protein microarray containing 8000 human proteins. A control reaction contained the same CSF sample but was not supplemented with ubiquitin or the energy mix.

A specific subset of proteins that are disproportionately expressed in brain (compared to a background of all the proteins that were on the chip) were found to be ubiquitinated (i.e., showed at least 2.5-fold higher signal than in the control), as shown in FIG. 11. The proteins that underwent CSF-mediated ubiquitination were distinct from background modification seen under control conditions. The functional annotation categories (gene ontology ('GO') terms) of these proteins were analyzed using the FatiGO online tool. List #1 shown in FIG. 11 holds the accession numbers for proteins that were highly ubiquitinated in comparison to the control (i.e. predicted list). List #2 holds the accession numbers of all the proteins on the microarray (i.e. background list). The 'GO' terms that are labeled with an asterisk (*) were shown to be enriched in this analysis, and the percentages of their appearance in the predicted list and in the background list is given in the third column. For comparison, terms associated with stress response (second row) showed no difference percentage of appearance in the ubiquitinated list when compared to the background list.

Example IV

Figure 12:
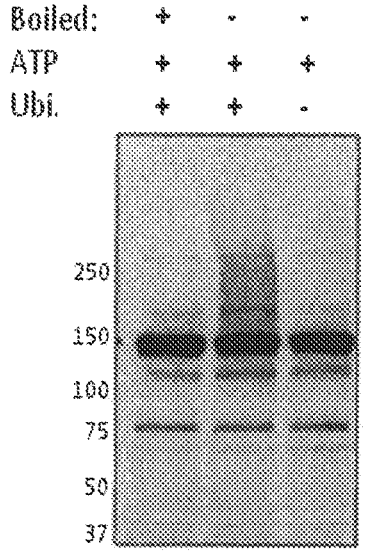
FIG. 12 shows a Western blot of normal human CSF proteins that were polyubiquitinated using enzyme activity in CSF.

Analysis of Protein Ubiquitination in Normal Human Cerebrospinal Fluid (CSF) Sample The ubiquitinating activity in a normal human CSF sample was tested by Western blotting. The ubiquitination reaction was started by adding an ATP regenerating system (2 mM ATP and 150 mM creatine phosphate) and ubiquitin (5 μM) to an aliquot of the CSF sample, and the reaction was run for 1 hour at 30° C. After the reaction was completed, the reaction mixture was subjected to SDS-PAGE and detection was performed with an anti-polyubiquitin antibody (FK1, Biomol). The results are shown in FIG. 12. There was a high molecular weight smear of ubiquitinated proteins in the reaction that included CSF and added ubiquitin, as compared to negative controls (CSF treated at 95° C. for 5 min or ubiquitin omitted).

Figure 13:
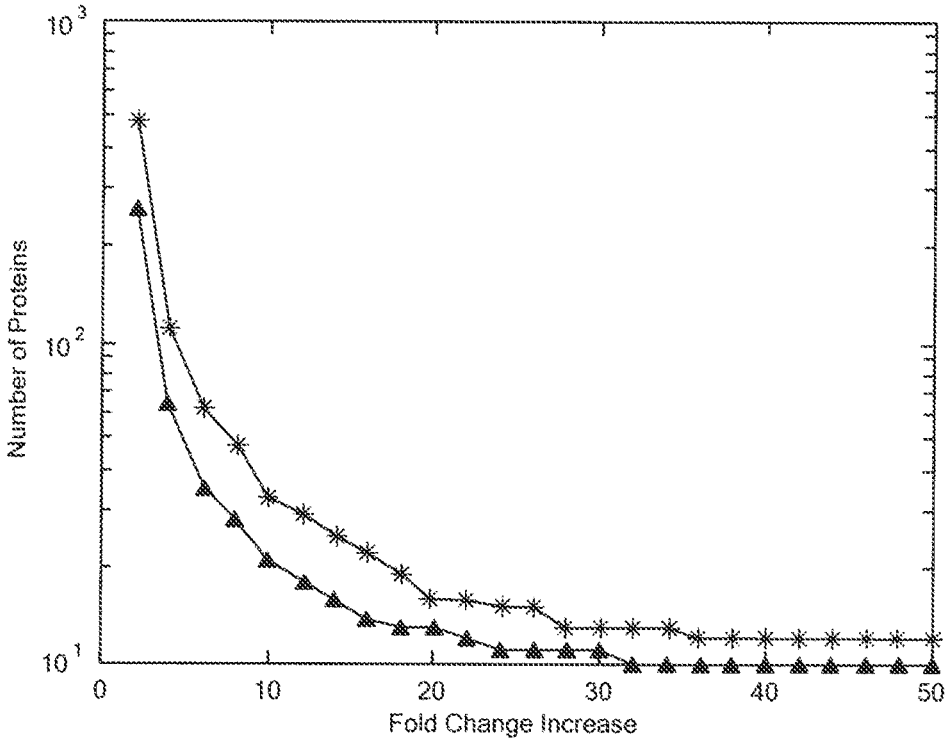
FIG. 13 shows the results of ubiquitination of a microarray of human proteins using normal human CSF. The number of ubiquitinated proteins detected is represented as a function of the fold increase of fluorescence over background.
Figure 14:
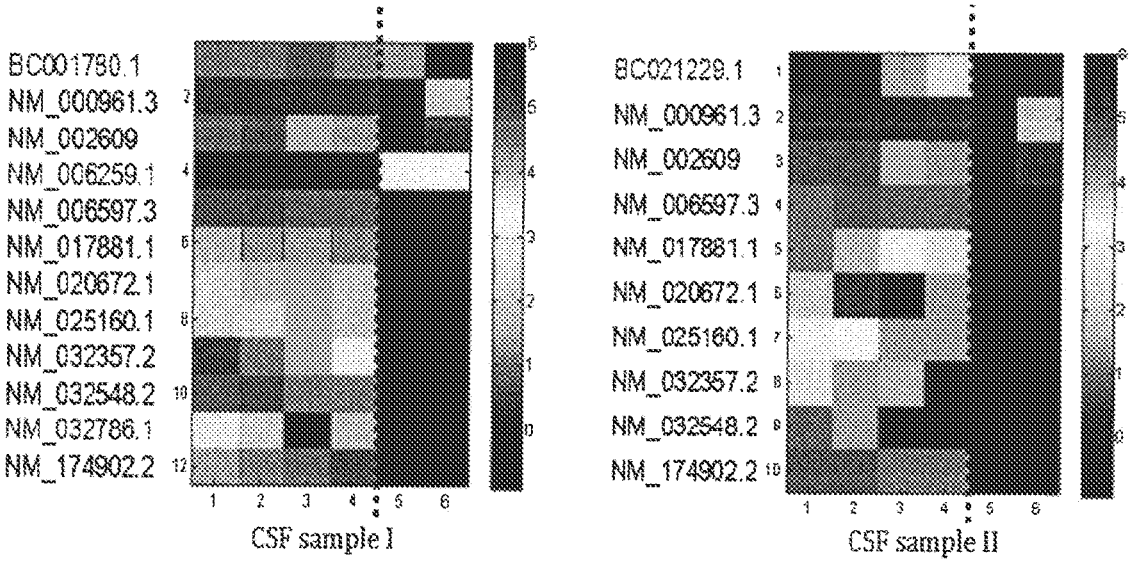
FIG. 14 shows human proteins detected on a microarray as polyubiquitinated by enzymes present in two normal human CSF samples. The proteins shown revealed a fluorescence signal at least 50-fold over background.

Next, the ubiquitinating activity of CSF was tested by allowing it to ubiqutinate proteins in a human protein microarray. The CSF sample was supplemented with 2 mM ATP and 150 mM creatine phosphate and ubiquitin (5 μM). The sample was then incubated on a Human PROTOARRAY® (Invitrogen) protein microarray in order to identify the basal ubiquitination activity in the sample. After incubation of the samples on the arrays for 60 min at 25° C., the activity was stopped by washing the microarrays with TBS containing 0.05% Tween-20, and the modified proteins were identified using a first antibody specific for the polyubiqutinated state, and a second antibody (DyLight 649-conjugated goat anti-mouse IgM with minimal cross-reactivity to human, (catalog #115-495-075), Jackson ImmunoResearch) directed to the first antibody. The second antibody carried a fluorescent label (DyLight 649) for detection. The signal intensity of each spot in the microarray (reflecting the ubiquitination of the protein on that spot) was used to statistically identify ubiquitinated proteins (i.e., those spots having signal statistically significant over background fluorescence or a control spot). Ubiquitinated proteins in the array showed a difference of between 2- and 50-fold compared to a control reaction without added CSF (FIG. 13). The number of proteins that met the criteria ranged from 12 to 485 proteins in one CSF sample (lower line, •) and from 10 to 265 in the other (upper line, +). FIG. 14 presents a list of proteins that showed increased modification signal in each of the two CSF samples at a level of more than 50-fold when compared to the control (non-CSF) reaction, together with the fluorescence intensity of four spots for each protein. The scale indicates the value (log transformed) of each of the 4 duplicate spots of these proteins (2 microarrays; 2 spots per microarray, lanes 1-4) compared to the values on the control array on the right (lanes 5-6). A colorbar is given on the right (blue (bottom of the scale), low reactivity; red (top of the scale), high reactivity). A list of proteins that showed at least a 50-fold increase in their level of ubiquitination by the CSF (vs. no CSF) is presented in Table 5.

TABLE 5

| Accession | Protein Description |
|---|---|
| NM_006259 | S100 calcium binding protein A14 (S100A14), mRNA |
| NM_020672 | Williams Beuren syndrome chromosome region 22, mRNA (cDNA clone MGC: 2022 IMAGE: 3544156) |

TABLE 5-continued

| Accession | Protein Description |
|---|---|
| BC001780 | zinc finger CCCH-type containing 10 (ZC3H10), mRNA |
| NM_032786 | chemokine (C-X-C motif) ligand 11 (CXCL11), mRNA |
| NM_032357 | ankyrin repeat and BTB (POZ) domain containing 1 (ABTB1), transcript variant 1, mRNA |
| NM_006597 | interleukin 1, alpha (IL1A), mRNA |
| NM_032548 | v-akt murine thymoma viral oncogene homolog 3 (protein kinase B, gamma) (AKT3), transcript variant 1, mRNA |
| NM_174902 | serine carboxypeptidase 1, mRNA (cDNA clone IMAGE: 4328599), partial cds |
| NM_000961 | v-raf murine sarcoma 3611 viral oncogene homolog (ARAF), mRNA |
| NM_002609 | tec protein tyrosine kinase (TEC), mRNA |
| NM_025160 | myotilin (MYOT), transcript variant 1, mRNA |
| NM_017881 | platelet-derived growth factor receptor, beta polypeptide (PDGFRB), mRNA |
| NM_033505 | SELI selenoprotein I (SLE1) |

Example V

Proteins Modified with Ubiquitin-Like Modifiers Upon Mitotic Release

The PTM of human proteins in a microarray was studied using functional cell extracts from HeLa S3 cells obtained after release from the mitotic checkpoint (CP). Growth, cell cycle modulation, preparation of extracts of the cells, and microarray measurements were as described in Example 1. Separate reactions were performed using each of the following modifying moieties (ubiquitin-like modifiers): ubiquitin, sumo1, sumo2/3, FAT10, UFM1, and ISG15. Table 1 describes further details of selected ubiquitin-like modifiers. In each case, the cell extract was supplemented with energy mix plus 5 μM of the respective modifying moiety.

Checkpoint extracts from HeLa S3 cells arrested with nocodazole were divided into two aliquots, one was denoted as the checkpoint-arrested extract (CP-arrested), and one was supplemented with UbcH10 to relieve the checkpoint arrest (CP-released). Microarrays were incubated with these extracts to allow the proteins on the array to be modified. Each microarray contained approximately 8000 proteins spotted in duplicates at a reported level of around 10 pg per spot (median diameter approximately 150 μm). After washing the reaction off the microarray, an antibody specific to the modifying moiety used in the reaction was added to detect modified proteins on the microarray. Microarrays were scanned, and the median signal intensity and local background of each spot was measured. Then, the anti-modifier antibody was detected by adding a fluorescently-labeled secondary antibody. Microarrays were scanned and the median signal intensity and local background of each spot was measured. The data were then organized in a matrix where each column contains the reactivity measured for a given array, and each row contains the reactivity measured for a given protein over all arrays. The negative values were set to zero, and the data were then normalized using a quantile normalization algorithm. Table 6 summarizes the proteins that were either differentially modified in anaphase over metaphase or were highly modified. The highly modified (but not differentially modified) proteins are indicated with an asterisk, and the remaining proteins were differentially modified.

TABLE 6

| GenBank Accession | Gene Symbol | Name |
|---|---|---|
| Ubiquitin | | |
| BC001396 | C9ORF32 | CHROMOSOME 9 OPEN READING FRAME 32 |
| BC004967 | UBAC1 | UBIQUITIN ASSOCIATED DOMAIN CONTAINING 1 |
| BC007581 | ALDH4A1 | ALDEHYDE DEHYDROGENASE 4 FAMILY, MEMBER A1 |
| BC008720 | CRELD1 | DKFZP566D213 PROTEIN |
| BC010369 | RNF111 | RING FINGER PROTEIN 111 |
| BC011399 | SYK | SPLEEN TYROSINE KINASE |
| BC013173 | RSPRY1 | RING FINGER AND SPRY DOMAIN CONTAINING 1 |
| BC015219 | RBCK1 | CHROMOSOME 20 OPEN READING FRAME 18 |
| BC020221 | STAC | SH3 AND CYSTEINE RICH DOMAIN |
| BC021988 | NDFIP2 | NEDD4 FAMILY INTERACTING PROTEIN 2 |
| BC032518 | CCNG2 | CYCLIN G2 |
| BC036540 | LOC400120 | HYPOTHETICAL LOC400120 |
| BC041133 | RASL10B | RAS-LIKE, FAMILY 10, MEMBER B |
| BC044239 | ANKRD13D | ANKYRIN REPEAT DOMAIN 13 FAMILY, MEMBER D |
| BC046151 | TOM1 | TARGET OF MYB1 (CHICKEN) |
| BC048970 | TTLL7 | TUBULIN TYROSINE LIGASE-LIKE FAMILY, MEMBER 7 |
| BC056240 | SPRR1B | SMALL PROLINE-RICH PROTEIN 1B (CORNIFIN) |
| BC066340 | BLOC1S1 | BIOGENESIS OF LYSOSOME-RELATED ORGANELLES COMPLEX-1, SUBUNIT 1 |
| NM_000875 | IGF1R | INSULIN-LIKE GROWTH FACTOR 1 RECEPTOR |
| NM_001004056 | GRK4 | G PROTEIN-COUPLED RECEPTOR KINASE 4 |
| NM_001220 | CAMK2B | CALCIUM/CALMODULIN-DEPENDENT PROTEIN KINASE (CAM KINASE) II BETA |
| NM_002103 | GYS1 | GLYCOGEN SYNTHASE 1 (MUSCLE) |
| NM_002378 | MATK | MEGAKARYOCYTE-ASSOCIATED TYROSINE KINASE |
| NM_002648 | PIM1 | PIM-1 ONCOGENE |
| NM_002810 | PSMD4 | PROTEASOME (PROSOME, MACROPAIN) 26S SUBUNIT, NON-ATPASE, 4 |
| NM_003045 | SLC7A1 | SOLUTE CARRIER FAMILY 7 (CATIONIC AMINO ACID TRANSPORTER, Y+ SYSTEM), MEMBER 1 |
| NM_003403 | YY1 | YY1 TRANSCRIPTION FACTOR |
| NM_004438 | EPHA4 | EPH RECEPTOR A4 |
| NM_004712 | HGS | HEPATOCYTE GROWTH FACTOR-REGULATED TYROSINE KINASE SUBSTRATE |
| NM_004783 | TAOK2 | TAO KINASE 2 |
| NM_005030 | PLK1 | POLO-LIKE KINASE 1 (*DROSOPHILA*) |
| NM_005727 | TSPAN1 | TETRASPANIN 1 |
| NM_005737 | ARL4C | ADP-RIBOSYLATION FACTOR-LIKE 4C |
| NM_006007 | ZFAND5 | ZINC FINGER, A20 DOMAIN CONTAINING 2 |
| NM_006293 | TYRO3 | TYRO3 PROTEIN TYROSINE KINASE |
| NM_013242 | C16ORF80 | GENE TRAP LOCUS 3 (MOUSE) |
| NM_018215 | FLJ10781 | HYPOTHETICAL PROTEIN FLJ10781 |
| NM_018384 | GIMAP5 | GTPASE, IMAP FAMILY MEMBER 5 |
| NM_022905 | TTC23 | TETRATRICOPEPTIDE REPEAT DOMAIN 23 |
| NM_032182 | KIAA0157 | KIAA0157 |
| NM_032765 | TRIM52 | TRIPARTITE MOTIF-CONTAINING 52 |
| NM_080823 | SRMS | SRC-RELATED KINASE LACKING C-TERMINAL REGULATORY TYROSINE AND N-TERMINAL MYRISTYLATION SITES |
| NM_130439 | MXI1 | MAX INTERACTOR 1 |
| NM_152285 | ARRDC1 | ARRESTIN DOMAIN CONTAINING 1 |
| NM_153217 | TMEM174 | HYPOTHETICAL PROTEIN MGC13034 |
| NM_153822 | PSMD4 | PROTEASOME (PROSOME, MACROPAIN) 26S SUBUNIT, NON-ATPASE, 4 |
| NM_173541 | C10ORF91 | CHROMOSOME 10 OPEN READING FRAME 91 |
| NM_194271 | RNF34 | RING FINGER PROTEIN 34 |
| BC016381 | NA | NA |
| BC004967* | UBAC1 | UBIQUITIN ASSOCIATED DOMAIN CONTAINING 1 |
| BC010369* | RNF111 | RING FINGER PROTEIN 111 |
| BC014475* | BIRC7 | LIVIN INHIBITOR-OF-APOTOSIS |
| BC015569* | ARL6IP4 | ADP-RIBOSYLATION-LIKE FACTOR 6 INTERACTING PROTEIN 4 |
| BC021988* | NDFIP2 | NEDD4 FAMILY INTERACTING PROTEIN 2 |
| BC023982* | C5ORF32 | PUTATIVE NUCLEAR PROTEIN ORF1-FL49 |
| BC025700* | AFF4 | AF4/FMR2 FAMILY, MEMBER 4 |
| BC044239* | ANKRD13D | ANKYRIN REPEAT DOMAIN 13 FAMILY, MEMBER D |
| BC053895* | IRS1 | INSULIN RECEPTOR SUBSTRATE 1 |
| BC054049* | ZNF364 | ZINC FINGER PROTEIN 364 |
| BC060833* | PRRG1 | PROLINE RICH GLA (G-CARBOXYGLUTAMIC ACID) 1 |
| NM_001033551* | TOM1L2 | TARGET OF MYB1-LIKE 2 (CHICKEN) |

TABLE 6-continued

| GenBank Accession | Gene Symbol | Name |
|---|---|---|
| NM_002019* | FLT1 | FMS-RELATED TYROSINE KINASE 1 (VASCULAR ENDOTHELIAL GROWTH FACTOR/VASCULAR PERMEABILITY FACTOR RECEPTOR) |
| NM_002110* | HCK | HEMOPOIETIC CELL KINASE |
| NM_002253* | KDR | KINASE INSERT DOMAIN RECEPTOR (A TYPE III RECEPTOR TYROSINE KINASE) |
| NM_002938* | RNF4 | RING FINGER PROTEIN 4 |
| NM_002944* | ROS1 | V-ROS UR2 SARCOMA VIRUS ONCOGENE HOMOLOG 1 (AVIAN) |
| NM_002946* | RPA2 | REPLICATION PROTEIN A2, 32 KDA |
| NM_005053* | RAD23A | RAD23 HOMOLOG A (*S. CEREVISIAE*) |
| NM_005228* | EGFR | EPIDERMAL GROWTH FACTOR RECEPTOR (ERYTHROBLASTIC LEUKEMIA VIRAL (V-ERB-B) ONCOGENE HOMOLOG, AVIAN) |
| NM_012478* | WBP2 | WW DOMAIN BINDING PROTEIN 2 |
| NM_017949* | CUEDC1 | CUE DOMAIN CONTAINING 1 |
| NM_020182* | TMEPAI | TRANSMEMBRANE, PROSTATE ANDROGEN INDUCED RNA |
| NM_020630* | RET | RET PROTO-ONCOGENE (MULTIPLE ENDOCRINE NEOPLASIA AND MEDULLARY THYROID CARCINOMA 1, HIRSCHSPRUNG DISEASE) |
| NM_030636* | EEPD1 | KIAA1706 PROTEIN |
| NM_130465* | TSPAN17 | TETRASPANIN 17 |
| NM_152267* | RNF185 | RING FINGER PROTEIN 185 |
| NM_153229* | TMEM92 | TRANSMEMBRANE PROTEIN 92 |
| NM_153345* | TMEM139 | HYPOTHETICAL PROTEIN FLJ90586 |
| NM_194271* | RNF34 | RING FINGER PROTEIN 34 |
| Sumo2/3 | | |
| NM_014805 | EPM2AIP1 | EPM2A (LAFORIN) INTERACTING PROTEIN 1 |
| NM_177974 | CASC4 | CANCER SUSCEPTIBILITY CANDIDATE 4 |
| BC017789 | CHORDC1 | CYSTEINE AND HISTIDINE-RICH DOMAIN (CHORD)-CONTAINING 1 |
| NM_018393 | TCP11L1 | T-COMPLEX 11 (MOUSE) LIKE 1 |
| NM_017588 | WDR5 | WD REPEAT DOMAIN 5 |
| BC056402 | LOC144097 | HYPOTHETICAL PROTEIN BC007540 |
| NM_003697 | OR5F1 | OLFACTORY RECEPTOR, FAMILY 5, SUBFAMILY F, MEMBER 1 |
| NM_014868 | RNF10 | RING FINGER PROTEIN 10 |
| NM_016269 | LEF1 | LYMPHOID ENHANCER-BINDING FACTOR 1 |
| BC014475 | BIRC7 | LIVIN INHIBITOR-OF-APOTOSIS |
| BC009207 | HIC2 | HYPERMETHYLATED IN CANCER 2 |
| NM_031845 | MAP2 | MICROTUBULE-ASSOCIATED PROTEIN 2 |
| BC020523 | INTS7 | CHROMOSOME 1 OPEN READING FRAME 73 |
| NM_018679 | TCP11 | T-COMPLEX 11 (MOUSE) |
| NM_019087 | ARL15 | ADP-RIBOSYLATION FACTOR-LIKE 15 |
| BC043247 | TLE3 | TRANSDUCIN-LIKE ENHANCER OF SPLIT 3 (E(SP1) HOMOLOG, *DROSOPHILA*) |
| BC002677 | AHDC1 | AT HOOK, DNA BINDING MOTIF, CONTAINING 1 |
| NM_003403 | YY1 | YY1 TRANSCRIPTION FACTOR |
| BC039583 | MGEA5 | MENINGIOMA EXPRESSED ANTIGEN 5 (HYALURONIDASE) |
| NM_015148 | PASK | PAS DOMAIN CONTAINING SERINE/THREONINE KINASE |
| BC010125 | C3ORF37 | CHROMOSOME 3 OPEN READING FRAME 37 |
| NM_001786 | CDC2 | CELL DIVISION CYCLE 2, G1 TO S AND G2 TO M |
| BC005008 | CEACAM6 | CARCINOEMBRYONIC ANTIGEN-RELATED CELL ADHESION MOLECULE 6 (NON-SPECIFIC CROSS REACTING ANTIGEN) |
| NM_144706 | C2ORF15 | CHROMOSOME 2 OPEN READING FRAME 15 |
| NM_007277 | EXOC3 | EXOCYST COMPLEX COMPONENT 3 |
| NM_002648 | PIM1 | PIM-1 ONCOGENE |
| NM_002019 | FLT1 | FMS-RELATED TYROSINE KINASE 1 (VASCULAR ENDOTHELIAL GROWTH FACTOR/VASCULAR PERMEABILITY FACTOR RECEPTOR) |
| NM_152619 | DCLK2 | DOUBLECORTIN AND CAM KINASE-LIKE 2 |
| BC022253 | SLC6A15 | SOLUTE CARRIER FAMILY 6, MEMBER 15 |
| NM_017949 | CUEDC1 | CUE DOMAIN CONTAINING 1 |
| NM_006002 | UCHL3 | UBIQUITIN CARBOXYL-TERMINAL ESTERASE L3 (UBIQUITIN THIOLESTERASE) |
| NM_001278 | CHUK | CONSERVED HELIX-LOOP-HELIX UBIQUITOUS KINASE |
| NM_001219 | CALU | CALUMENIN |
| BC050645 | BYSL | BYSTIN-LIKE |
| BC040272 | IL16 | INTERLEUKIN 16 (LYMPHOCYTE CHEMOATTRACTANT FACTOR) |

TABLE 6-continued

| GenBank Accession | Gene Symbol | Name |
|---|---|---|
| BC023152 | GYG2 | GLYCOGENIN 2 |
| NM_002011 | FGFR4 | FIBROBLAST GROWTH FACTOR RECEPTOR 4 |
| BC024725 | ANKRD50 | ANKYRIN REPEAT DOMAIN 50 |
| NM_138353 | LOC90379 | HYPOTHETICAL PROTEIN BC002926 |
| BC061697 | C3ORF62 | CHROMOSOME 3 OPEN READING FRAME 62 |
| NM_015417 | SPEF1 | CHROMOSOME 20 OPEN READING FRAME 28 |
| NM_181707 | C17ORF64 | CHROMOSOME 17 OPEN READING FRAME 64 |
| NM_199334 | THRA | THYROID HORMONE RECEPTOR, ALPHA (ERYTHROBLASTIC LEUKEMIA VIRAL (V-ERB-A) ONCOGENE HOMOLOG, AVIAN) |
| BC060760 | GIMAP6 | IMMUNE ASSOCIATED NUCLEOTIDE 2 |
| NM_002738 | PRKCB1 | PROTEIN KINASE C, BETA 1 |
| BC000247 | THAP4 | THAP DOMAIN CONTAINING 4 |
| BC013567 | USP48 | HYPOTHETICAL PROTEIN FLJ11328 |
| NM_198498 | C11ORF53 | CHROMOSOME 11 OPEN READING FRAME 53 |
| BC012289 | KIAA0515 | KIAA0515 PROTEIN |
| BC004219 | AGPAT3 | 1-ACYLGLYCEROL-3-PHOSPHATE O-ACYLTRANSFERASE 3 |
| NM_130766 | SKIP | SKELETAL MUSCLE AND KIDNEY ENRICHED INOSITOL PHOSPHATASE |
| NM_001328 | CTBP1 | C-TERMINAL BINDING PROTEIN 1 |
| BC058861 | SULT1C4 | SULFOTRANSFERASE FAMILY, CYTOSOLIC, 1C, MEMBER 2 |
| BC046117 | DNALI1 | DYNEIN, AXONEMAL, LIGHT INTERMEDIATE POLYPEPTIDE 1 |
| NM_032017 | STK40 | SERINE/THREONINE KINASE 40 |
| NM_173822 | FAM126B | HYPOTHETICAL PROTEIN MGC39518 |
| BC032120 | C20ORF11 | CHROMOSOME 20 OPEN READING FRAME 11 |
| NM_001556 | IKBKB | INHIBITOR OF KAPPA LIGHT POLYPEPTIDE GENE ENHANCER IN B-CELLS, KINASE BETA |
| NM_032014 | MRPS24 | MITOCHONDRIAL RIBOSOMAL PROTEIN S24 |
| NM_145796 | POGZ | POGO TRANSPOSABLE ELEMENT WITH ZNF DOMAIN |
| NM_001042599 | ERBB4 | |
| NM_017629 | EIF2C4 | ARGONAUTE 4 |
| NM_032846 | RAB2B | RAB2B, MEMBER RAS ONCOGENE FAMILY |
| BC011234 | SMNDC1 | SURVIVAL MOTOR NEURON DOMAIN CONTAINING 1 |
| NM_017583 | TRIM44 | TRIPARTITE MOTIF-CONTAINING 44 |
| NM_005639 | SYT1 | SYNAPTOTAGMIN I |
| NM_016954 | TBX22 | T-BOX 22 |
| NM_002796 | PSMB4 | PROTEASOME (PROSOME, MACROPAIN) SUBUNIT, BETA TYPE, 4 |
| NM_000666 | ACY1 | AMINOACYLASE 1 |
| NM_032326 | TMEM175 | HYPOTHETICAL PROTEIN MGC4618 |
| NM_001197 | BIK | BCL2-INTERACTING KILLER (APOPTOSIS-INDUCING) |
| NM_170672 | RASGRP3 | RAS GUANYL RELEASING PROTEIN 3 (CALCIUM AND DAG-REGULATED) |
| BC017357 | ZNF765 | HYPOTHETICAL PROTEIN BC001610 |
| BC020233 | IGLC2 | IMMUNOGLOBULIN LAMBDA CONSTANT 1 (MCG MARKER) |
| BC059374 | STK31 | SERINE/THREONINE KINASE 31 |
| NM_014248 | RBX1 | RING-BOX 1 |
| NM_005158 | ABL2 | V-ABL ABELSON MURINE LEUKEMIA VIRAL ONCOGENE HOMOLOG 2 (ARG, ABELSON-RELATED GENE) |
| NM_018668 | VPS33B | VACUOLAR PROTEIN SORTING 33B (YEAST) |
| BC063451 | TCP10L2 | T-COMPLEX 10 (MOUSE) |
| NM_002623 | PFDN4 | PREFOLDIN SUBUNIT 4 |
| BC016652 | BMX | BMX NON-RECEPTOR TYROSINE KINASE |
| NM_153486 | LDHD | LACTATE DEHYDROGENASE D |
| NM_033307 | CASP4 | CASPASE 4, APOPTOSIS-RELATED CYSTEINE PEPTIDASE |
| NM_004113 | FGF12 | FIBROBLAST GROWTH FACTOR 12 |
| NM_005148 | UNC119 | UNC-119 HOMOLOG (*C. ELEGANS*) |
| NM_004838 | HOMER3 | HOMER HOMOLOG 3 (*DROSOPHILA*) |
| NM_016355 | DDX47 | DEAD (ASP-GLU-ALA-ASP) (SEQ ID NO: 2) BOX POLYPEPTIDE 47 |
| NM_014548 | TMOD2 | TROPOMODULIN 2 (NEURONAL) |
| BC016964 | MRGPRF | MAS-RELATED GPR, MEMBER F |
| BC029220 | SOX5 | SRY (SEX DETERMINING REGION Y)-BOX 5 |
| BC030711 | C2ORF13 | CHROMOSOME 2 OPEN READING FRAME 13 |
| NM_001571 | IRF3 | INTERFERON REGULATORY FACTOR 3 |
| BC031830 | KLHL32 | KIAA1900 |
| NM_153498 | CAMK1D | CALCIUM/CALMODULIN-DEPENDENT PROTEIN KINASE ID |
| NM_144602 | C16ORF78 | HYPOTHETICAL PROTEIN MGC32905 |

TABLE 6-continued

| GenBank Accession | Gene Symbol | Name |
|---|---|---|
| NM_012325 | MAPRE1 | MICROTUBULE-ASSOCIATED PROTEIN, RP/EB FAMILY, MEMBER 1 |
| BC057840 | PSMB5 | PROTEASOME (PROSOME, MACROPAIN) SUBUNIT, BETA TYPE, 5 |
| NM_079422 | MYL1 | MYOSIN, LIGHT POLYPEPTIDE 1, ALKALI; SKELETAL, FAST |
| BC029267 | MUC20 | MUCIN 20 |
| NM_020830 | WDFY1 | WD REPEAT AND FYVE DOMAIN CONTAINING 1 |
| NM_033003 | GTF2I | |
| BC009571 | STRA13 | STIMULATED BY RETINOIC ACID 13 HOMOLOG (MOUSE) |
| NM_005030 | PLK1 | POLO-LIKE KINASE 1 (*DROSOPHILA*) |
| NM_022754 | SFXN1 | LIKELY ORTHOLOG OF MOUSE SIDEROFLEXIN 1 |
| BC012997 | SULF1 | SULFATASE 1 |
| NM_001221 | CAMK2D | CALCIUM/CALMODULIN-DEPENDENT PROTEIN KINASE (CAM KINASE) II DELTA |
| BC031691 | SLAIN2 | KIAA1458 PROTEIN |
| NM_014840 | NUAK1 | NUAK FAMILY, SNF1-LIKE KINASE, 1 |
| BC001772 | QARS | GLUTAMINYL-TRNA SYNTHETASE |
| NM_032693 | ARD1B | |
| BC025314 | IGHG1 | IMMUNOGLOBULIN HEAVY CONSTANT GAMMA 1 (G1M MARKER) |
| BC033491 | ADAD2 | TESTIS NUCLEAR RNA-BINDING PROTEIN-LIKE |
| BC009650 | PDS5A | SCC-112 PROTEIN |
| NM_018326 | GIMAP4 | GTPASE, IMAP FAMILY MEMBER 4 |
| NM_005239 | ETS2 | V-ETS ERYTHROBLASTOSIS VIRUS E26 ONCOGENE HOMOLOG 2 (AVIAN) |
| NM_006257 | PRKCQ | PROTEIN KINASE C, THETA |
| NM_152667 | NANP | N-ACETYLNEURAMINIC ACID PHOSPHATASE |
| BC001728* | TFPT | TCF3 (E2A) FUSION PARTNER (IN CHILDHOOD LEUKEMIA) |
| BC001772* | QARS | GLUTAMINYL-TRNA SYNTHETASE |
| BC007048* | ZMYM5 | ZINC FINGER, MYM-TYPE 5 |
| BC010125* | C3ORF37 | CHROMOSOME 3 OPEN READING FRAME 37 |
| BC017314* | ETS1 | V-ETS ERYTHROBLASTOSIS VIRUS E26 ONCOGENE HOMOLOG 1 (AVIAN) |
| BC020985* | COASY | COENZYME A SYNTHASE |
| BC036572* | ZCCHC12 | ZINC FINGER, CCHC DOMAIN CONTAINING 12 |
| BC040949* | MEF2D | MADS BOX TRANSCRIPTION ENHANCER FACTOR 2, POLYPEPTIDE D (MYOCYTE ENHANCER FACTOR 2D) |
| BC056402* | LOC144097 | HYPOTHETICAL PROTEIN BC007540 |
| BC056415* | RPAP3 | HYPOTHETICAL PROTEIN FLJ21908 |
| NM_001014796* | DDR2 | DISCOIDIN DOMAIN RECEPTOR FAMILY, MEMBER 2 |
| NM_001039468* | MARK2 | MAP/MICROTUBULE AFFINITY-REGULATING KINASE 2 |
| NM_001786* | CDC2 | CELL DIVISION CYCLE 2, G1 TO S AND G2 TO M |
| NM_001910* | CTSE | CATHEPSIN E |
| NM_002378* | MATK | MEGAKARYOCYTE-ASSOCIATED TYROSINE KINASE |
| NM_002497* | NEK2 | NIMA (NEVER IN MITOSIS GENE A)-RELATED KINASE 2 |
| NM_002938* | RNF4 | RING FINGER PROTEIN 4 |
| NM_003141* | TRIM21 | TRIPARTITE MOTIF-CONTAINING 21 |
| NM_006257* | PRKCQ | PROTEIN KINASE C, THETA |
| NM_006259* | PRKG2 | PROTEIN KINASE, CGMP-DEPENDENT, TYPE II |
| NM_006937* | SUMO2 | SMT3 SUPPRESSOR OF MIF TWO 3 HOMOLOG 2 (YEAST) |
| NM_015981* | CAMK2A | CALCIUM/CALMODULIN-DEPENDENT PROTEIN KINASE (CAM KINASE) II ALPHA |
| NM_016058* | TPRKB | TP53RK BINDING PROTEIN |
| NM_017838* | NOLA2 | NUCLEOLAR PROTEIN FAMILY A, MEMBER 2 (H/ACA SMALL NUCLEOLAR RNPS) |
| NM_021709* | SIVA1 | CD27-BINDING (SIVA) PROTEIN |
| NM_032752* | ZNF496 | ZINC FINGER PROTEIN 496 |
| NM_130807* | MOBKL2A | MOB1, MPS ONE BINDER KINASE ACTIVATOR-LIKE 2A (YEAST) |
| NM_145173* | DIRAS1 | DIRAS FAMILY, GTP-BINDING RAS-LIKE 1 |
| NM_175907* | ZADH2 | HYPOTHETICAL PROTEIN BC010734 |
| NM_033003* | NA | NA |
| Nedd8 | | |
| BC000178 | KCMF1 | POTASSIUM CHANNEL MODULATORY FACTOR 1 |
| BC000395 | LETMD1 | LETM1 DOMAIN CONTAINING 1 |
| BC001852 | THG1L | INTERPHASE CYCTOPLASMIC FOCI PROTEIN 45 |
| BC002526 | HSPA4 | HEAT SHOCK 70 KDA PROTEIN 4 |
| BC007312 | KIRREL2 | KIN OF IRRE LIKE 2 (*DROSOPHILA*) |

TABLE 6-continued

| GenBank Accession | Gene Symbol | Name |
|---|---|---|
| BC009074 | C8ORF70 | CHROMOSOME 8 OPEN READING FRAME 70 |
| BC009485 | C4ORF16 | CHROMOSOME 4 OPEN READING FRAME 16 |
| BC012945 | C19ORF57 | HYPOTHETICAL PROTEIN MGC11271 |
| BC018953 | SMARCD2 | SWI/SNF RELATED, MATRIX ASSOCIATED, ACTIN DEPENDENT REGULATOR OF CHROMATIN, SUBFAMILY D, MEMBER 2 |
| BC020658 | TMEM40 | TRANSMEMBRANE PROTEIN 40 |
| BC038504 | SNF1LK | SNF1-LIKE KINASE |
| BC050696 | C12ORF48 | CHROMOSOME 12 OPEN READING FRAME 48 |
| BC051849 | RPAIN | RPA INTERACTING PROTEIN |
| BC062736 | CTD-2090I13.4 | BASIC TRANSCRIPTION FACTOR 3, PSEUDOGENE 9 |
| NM_004235 | KLF4 | KRUPPEL-LIKE FACTOR 4 (GUT) |
| NM_004391 | CYP8B1 | CYTOCHROME P450, FAMILY 8, SUBFAMILY B, POLYPEPTIDE 1 |
| NM_005206 | CRK | V-CRK SARCOMA VIRUS CT10 ONCOGENE HOMOLOG (AVIAN) |
| NM_005651 | TDO2 | TRYPTOPHAN 2,3-DIOXYGENASE |
| NM_006251 | PRKAA1 | PROTEIN KINASE, AMP-ACTIVATED, ALPHA 1 CATALYTIC SUBUNIT |
| NM_012328 | DNAJB9 | DNAJ (H5P40) HOMOLOG, SUBFAMILY B, MEMBER 9 |
| NM_013442 | STOML2 | STOMATIN (EPB72)-LIKE 2 |
| NM_014878 | KIAA0020 | KIAA0020 |
| NM_018014 | BCL11A | B-CELL CLL/LYMPHOMA 11A (ZINC FINGER PROTEIN) |
| NM_019895 | CLNS1A | CHLORIDE CHANNEL, NUCLEOTIDE-SENSITIVE, 1A |
| NM_021803 | IL21 | INTERLEUKIN 21 |
| NM_152443 | RDH12 | RETINOL DEHYDROGENASE 12 (ALL-TRANS AND 9-CIS) |
| BC051366 | NA | NA |
| BC005008* | CEACAM6 | CARCINOEMBRYONIC ANTIGEN-RELATED CELL ADHESION MOLECULE 6 (NON-SPECIFIC CROSS REACTING ANTIGEN) |
| BC006323* | ABCB7 | ATP-BINDING CASSETTE, SUB-FAMILY B (MDR/TAP), MEMBER 7 |
| BC011707* | NRBF2 | NUCLEAR RECEPTOR BINDING FACTOR 2 |
| BC012109* | HOMER2 | HOMER HOMOLOG 2 (*DROSOPHILA*) |
| BC020985* | COASY | COENZYME A SYNTHASE |
| BC021906* | FMNL1 | FORMIN-LIKE 1 |
| BC053895* | IRS1 | INSULIN RECEPTOR SUBSTRATE 1 |
| BC056669* | DCUN1D2 | DCN1, DEFECTIVE IN CULLIN NEDDYLATION 1, DOMAIN CONTAINING 2 (*S. CEREVISIAE*) |
| BC058924* | UBE2M | UBIQUITIN-CONJUGATING ENZYME E2M (UBC12 HOMOLOG, YEAST) |
| NM_001004105* | GRK6 | G PROTEIN-COUPLED RECEPTOR KINASE 6 |
| NM_001039468* | MARK2 | MAP/MICROTUBULE AFFINITY-REGULATING KINASE 2 |
| NM_001798* | CDK2 | CYCLIN-DEPENDENT KINASE 2 |
| NM_001895* | CSNK2A1 | CASEIN KINASE 2, ALPHA 1 POLYPEPTIDE |
| NM_003141* | TRIM21 | TRIPARTITE MOTIF-CONTAINING 21 |
| NM_003668* | MAPKAPK5 | MITOGEN-ACTIVATED PROTEIN KINASE-ACTIVATED PROTEIN KINASE 5 |
| NM_005019* | PDE1A | PHOSPHODIESTERASE 1A, CALMODULIN-DEPENDENT |
| NM_005038* | PPID | PEPTIDYLPROLYL ISOMERASE D (CYCLOPHILIN D) |
| NM_006156* | NEDD8 | NEURAL PRECURSOR CELL EXPRESSED, DEVELOPMENTALLY DOWN-REGULATED 8 |
| NM_012247* | SEPHS1 | SELENOPHOSPHATE SYNTHETASE 1 |
| NM_012325* | MAPRE1 | MICROTUBULE-ASSOCIATED PROTEIN, RP/EB FAMILY, MEMBER 1 |
| NM_015417* | SPEF1 | CHROMOSOME 20 OPEN READING FRAME 28 |
| NM_016058* | TPRKB | TP53RK BINDING PROTEIN |
| NM_018014* | BCL11A | B-CELL CLL/LYMPHOMA 11A (ZINC FINGER PROTEIN) |
| NM_022754* | SFXN1 | LIKELY ORTHOLOG OF MOUSE SIDEROFLEXIN 1 |
| NM_030662* | MAP2K2 | MITOGEN-ACTIVATED PROTEIN KINASE KINASE 2 |
| NM_032141* | CCDC55 | COILED-COIL DOMAIN CONTAINING 55 |
| NM_130439* | MXI1 | MAX INTERACTOR 1 |
| NM_138559* | BCL11A | B-CELL CLL/LYMPHOMA 11A (ZINC FINGER PROTEIN) |
| NM_175907* | ZADH2 | HYPOTHETICAL PROTEIN BC010734 |
| NM_212535* | PRKCB1 | PROTEIN KINASE C, BETA 1 |
| FAT10 | | |
| NM_005737 | ARL4C | ADP-RIBOSYLATION FACTOR-LIKE 4C |
| BC013648 | EFHD2 | EF-HAND DOMAIN FAMILY, MEMBER D2 |
| BC031247 | CCDC67 | COILED-COIL DOMAIN CONTAINING 67 |
| NM_015621 | CCDC69 | COILED-COIL DOMAIN CONTAINING 69 |

TABLE 6-continued

| GenBank Accession | Gene Symbol | Name |
|---|---|---|
| NM_024099 | C11ORF48 | CHROMOSOME 11 OPEN READING FRAME 48 |
| NM_016951 | CKLF | CHEMOKINE-LIKE FACTOR |
| BC008919 | TBC1D9B | KIAA0676 PROTEIN |
| NM_032855 | HSH2D | HEMATOPOIETIC SH2 DOMAIN CONTAINING |
| NM_152788 | ANKS1B | ANKYRIN REPEAT AND STERILE ALPHA MOTIF DOMAIN CONTAINING 1B |
| NM_001277 | CHKA | CHOLINE KINASE ALPHA |
| NM_152434 | CWF19L2 | CWF19-LIKE 2, CELL CYCLE CONTROL (*S. POMBE*) |
| NM_004811 | LPXN | LEUPAXIN |
| NM_182739 | NDUFB6 | NADH DEHYDROGENASE (UBIQUINONE) 1 BETA SUBCOMPLEX, 6, 17 KDA |
| BC053602 | C15ORF38 | HYPOTHETICAL PROTEIN FLJ35955 |
| NM_018976 | SLC38A2 | SOLUTE CARRIER FAMILY 38, MEMBER 2 |
| BC004967 | UBAC1 | UBIQUITIN ASSOCIATED DOMAIN CONTAINING 1 |
| BC010360 | LMBRD1 | LMBR1 DOMAIN CONTAINING 1 |
| BC016381 | NA | HYPOTHETICAL PROTEIN |
| BC017101 | POMZP3 | POM (POM121 HOMOLOG, RAT) AND ZP3 FUSION |
| BC026175 | ATF2 | ACTIVATING TRANSCRIPTION FACTOR 2 |
| BC062359 | C8ORF47 | CHROMOSOME 8 OPEN READING FRAME 47 |
| NM_000301 | PLG | PLASMINOGEN |
| NM_002815 | PSMD11 | PROTEASOME (PROSOME, MACROPAIN) 26S SUBUNIT, NON-ATPASE, 11 |
| NM_002854 | PVALB | PARVALBUMIN |
| NM_012198 | GCA | GRANCALCIN, EF-HAND CALCIUM BINDING PROTEIN |
| NM_017727 | FLJ20254 | HYPOTHETICAL PROTEIN FLJ20254 |
| NM_021925 | C2ORF43 | HYPOTHETICAL PROTEIN FLJ21820 |
| NM_138785 | C6ORF72 | CHROMOSOME 6 OPEN READING FRAME 72 |
| NM_144686 | TMC4 | TRANSMEMBRANE CHANNEL-LIKE 4 |
| NM_012416 | RANBP6 | RAN BINDING PROTEIN 6 |
| NM_006899 | IDH3B | ISOCITRATE DEHYDROGENASE 3 (NAD+) BETA |
| BC001726 | NOL11 | NUCLEOLAR PROTEIN 11 |
| BC015219 | RBCK1 | CHROMOSOME 20 OPEN READING FRAME 18 |
| BC034801 | ZDHHC19 | ZINC FINGER, DHHC-TYPE CONTAINING 19 |
| BC022244 | PYCR1 | PYRROLINE-5-CARBOXYLATE REDUCTASE 1 |
| NM_006399 | BATF | BASIC LEUCINE ZIPPER TRANSCRIPTION FACTOR, ATF-LIKE |
| BC014949 | DHX58 | LIKELY ORTHOLOG OF MOUSE D11LGP2 |
| NM_014182 | ORMDL2 | ORM1-LIKE 2 (*S. CEREVISIAE*) |
| NM_024114 | TRIM48 | TRIPARTITE MOTIF-CONTAINING 48 |
| NM_006607 | PTTG2 | PITUITARY TUMOR-TRANSFORMING 2 |
| NM_004357 | CD151 | CD151 ANTIGEN (RAPH BLOOD GROUP) |
| NM_005513 | GTF2E1 | GENERAL TRANSCRIPTION FACTOR IIE, POLYPEPTIDE 1, ALPHA 56 KDA |
| NM_016231 | NLK | NEMO-LIKE KINASE |
| NM_054033 | FKBP1B | FK506 BINDING PROTEIN 1B, 12.6 KDA |
| NM_152646 | | hypothetical protein MGC23270 |
| NM_173518 | C8ORF45 | CHROMOSOME 8 OPEN READING FRAME 45 |
| NM_177951 | PPM1A | PROTEIN PHOSPHATASE 1A (FORMERLY 2C), MAGNESIUM-DEPENDENT, ALPHA ISOFORM |
| NM_020990 | CKMT1B | CREATINE KINASE, MITOCHONDRIAL 1B |
| NM_001258 | CDK3 | CYCLIN-DEPENDENT KINASE 3 |
| NM_138565 | CTTN | CORTACTIN |
| NM_018189 | DPPA4 | DEVELOPMENTAL PLURIPOTENCY ASSOCIATED 4 |
| NM_001330 | CTF1 | CARDIOTROPHIN 1 |
| BC029541 | LETM2 | LEUCINE ZIPPER-EF-HAND CONTAINING TRANSMEMBRANE PROTEIN 2 |
| NM_144594 | GTSF1 | FAMILY WITH SEQUENCE SIMILARITY 112, MEMBER B |
| NM_173192 | KCNIP2 | KV CHANNEL INTERACTING PROTEIN 2 |
| BC034468 | FLJ11171 | HYPOTHETICAL PROTEIN FLJ11171 |
| NM_033306 | CASP4 | CASPASE 4, APOPTOSIS-RELATED CYSTEINE PEPTIDASE |
| BC041132 | KIFC3 | KINESIN FAMILY MEMBER C3 |
| BC011461 | MITF | MICROPHTHALMIA-ASSOCIATED TRANSCRIPTION FACTOR |
| BC046214 | MPHOSPH8 | M-PHASE PHOSPHOPROTEIN, MPP8 |
| BC057774 | RG9MTD3 | RNA (GUANINE-9-) METHYLTRANSFERASE DOMAIN CONTAINING 3 |
| NM_016606 | REEP2 | RECEPTOR ACCESSORY PROTEIN 2 |
| NM_145265 | CCDC127 | SIMILAR TO RIKEN CDNA 0610011N22 |
| BC015056 | ACAD10 | ACYL-COENZYME A DEHYDROGENASE FAMILY, MEMBER 10 |
| BC007224 | GALNT10 | UDP-N-ACETYL-ALPHA-D-GALACTOSAMINE: POLYPEPTIDE N-ACETYLGALACTOSAMINYLTRANSFERASE 10 (GALNAC-T10) |

TABLE 6-continued

| GenBank Accession | Gene Symbol | Name |
|---|---|---|
| BC009289 | ACSBG1 | ACYL-COA SYNTHETASE BUBBLEGUM FAMILY MEMBER 1 |
| BC011786 | NA | CHROMOSOME 11 OPEN READING FRAME 43 |
| NM_000559 | HBG2 | HEMOGLOBIN, GAMMA A |
| NM_024680 | E2F8 | E2F TRANSCRIPTION FACTOR 8 |
| BC000557 | PEMT | PHOSPHATIDYLETHANOLAMINE N-METHYLTRANSFERASE |
| BC005974 | VAMP4 | VESICLE-ASSOCIATED MEMBRANE PROTEIN 4 |
| BC009771 | BCCIP | CDK INHIBITOR P21 BINDING PROTEIN |
| BC053508 | ARL6IP2 | ADP-RIBOSYLATION FACTOR-LIKE 6 INTERACTING PROTEIN 2 |
| NM_001307 | CLDN7 | CLAUDIN 7 |
| NM_002688 | 12:00 AM | SEPTIN 5 |
| NM_004123 | GIP | GASTRIC INHIBITORY POLYPEPTIDE |
| NM_004545 | NDUFB1 | NADH DEHYDROGENASE (UBIQUINONE) 1 BETA SUBCOMPLEX, 1, 7 KDA |
| NM_004712 | HGS | HEPATOCYTE GROWTH FACTOR-REGULATED TYROSINE KINASE SUBSTRATE |
| NM_005621 | S100A12 | S100 CALCIUM BINDING PROTEIN A12 (CALGRANULIN C) |
| NM_016388 | TRAT1 | T CELL RECEPTOR ASSOCIATED TRANSMEMBRANE ADAPTOR 1 |
| NM_138998 | DDX39 | DEAD (ASP-GLU-ALA-ASP) (SEQ ID NO: 2) BOX POLYPEPTIDE 39 |
| NM_144673 | CMTM2 | CKLF-LIKE MARVEL TRANSMEMBRANE DOMAIN CONTAINING 2 |
| NM_182597 | C7ORF53 | HYPOTHETICAL PROTEIN FLJ39575 |
| BC035601 | WWC3 | KIAA1280 PROTEIN |
| BC036365 | C10ORF81 | HYPOTHETICAL PROTEIN LOC338564 |
| NM_002103 | GYS1 | GLYCOGEN SYNTHASE 1 (MUSCLE) |
| NM_145252 | LOC124220 | SIMILAR TO COMMON SALIVARY PROTEIN 1 |
| NM_139280 | ORMDL3 | HYPOTHETICAL PROTEIN LOC51242 |
| NM_022372 | GBL | G PROTEIN BETA SUBUNIT-LIKE |
| BC052805 | EPB49 | ERYTHROCYTE MEMBRANE PROTEIN BAND 4.9 (DEMATIN) |
| NM_014551 | NCAPH2 | KLEISIN BETA |
| NM_017848 | FAM120C | CHROMOSOME X OPEN READING FRAME 17 |
| BC008141 | UCHL5IP | THREE PRIME REPAIR EXONUCLEASE 2 |
| NM_005832 | KCNMB2 | POTASSIUM LARGE CONDUCTANCE CALCIUM-ACTIVATED CHANNEL, SUBFAMILY M, BETA MEMBER 2 |
| NM_173517 | VKORC1L1 | VITAMIN K EPOXIDE REDUCTASE COMPLEX, SUBUNIT 1-LIKE 1 |
| NM_173473 | C10ORF104 | CHROMOSOME 10 OPEN READING FRAME 104 |
| NM_030650 | KIAA1715 | KIAA1715 |
| NM_014570 | ARFGAP3 | ADP-RIBOSYLATION FACTOR GTPASE ACTIVATING PROTEIN 3 |
| NM_021159 | RAP1GDS1 | RAP1, GTP-GDP DISSOCIATION STIMULATOR 1 |
| BC017066 | PRRC1 | HYPOTHETICAL PROTEIN MGC12103 |
| NM_014805 | EPM2AIP1 | EPM2A (LAFORIN) INTERACTING PROTEIN 1 |
| BC033734 | C17ORF66 | CHROMOSOME 17 OPEN READING FRAME 66 |
| NM_021644 | HNRPH3 | HETEROGENEOUS NUCLEAR RIBONUCLEOPROTEIN H3 (2H9) |
| BC021987 | NMI | N-MYC (AND STAT) INTERACTOR |
| NM_002489 | NDUFA4 | NADH DEHYDROGENASE (UBIQUINONE) 1 ALPHA SUBCOMPLEX, 4, 9 KDA |
| NM_033542 | DBNDD2 | CHROMOSOME 20 OPEN READING FRAME 35 |
| BC015754 | CADPS | CA2+-DEPENDENT SECRETION ACTIVATOR |
| NM_032357 | CCDC115 | HYPOTHETICAL PROTEIN MGC12981 |
| XM_291436 | | |
| BC012266 | ATG12 | ATG12 AUTOPHAGY RELATED 12 HOMOLOG (*S. CEREVISIAE*) |
| BC012377 | EGFL7 | EGF-LIKE-DOMAIN, MULTIPLE 7 |
| BC017943 | PPP1R1C | PROTEIN PHOSPHATASE 1, REGULATORY (INHIBITOR) SUBUNIT 1C |
| BC058031 | HP | HAPTOGLOBIN |
| BC060828 | ARID3A | AT RICH INTERACTIVE DOMAIN 3A (BRIGHT-LIKE) |
| NM_144586 | LYPD1 | LY6/PLAUR DOMAIN CONTAINING 1 |
| BC009106 | SEC16B | LEUCINE ZIPPER TRANSCRIPTION REGULATOR 2 |
| NM_018990 | CXORF9 | CHROMOSOME X OPEN READING FRAME 9 |
| NM_004935 | CDK5 | CYCLIN-DEPENDENT KINASE 5 |
| BC014484 | TOR1A | TORSIN FAMILY 1, MEMBER A (TORSIN A) |
| BC063111 | GGT6 | GAMMA-GLUTAMYLTRANSFERASE 6 HOMOLOG (RAT) |
| NM_023937 | MRPL34 | MITOCHONDRIAL RIBOSOMAL PROTEIN L34 |
| NM_030810 | TXNDC5 | THIOREDOXIN DOMAIN CONTAINING 5 |
| NM_138463 | TLCD1 | TLC DOMAIN CONTAINING 1 |
| BC007919 | STARD10 | START DOMAIN CONTAINING 10 |

TABLE 6-continued

| GenBank Accession | Gene Symbol | Name |
|---|---|---|
| BC016703 | ACSM5 | HYPOTHETICAL PROTEIN FLJ20581 |
| NM_001004354 | NRARP | SIMILAR TO ANKYRIN-REPEAT PROTEIN NRARP |
| NM_002436 | MPP1 | MEMBRANE PROTEIN, PALMITOYLATED 1, 55 KDA |
| NM_004013 | DMD | DYSTROPHIN (MUSCULAR DYSTROPHY, DUCHENNE AND BECKER TYPES) |
| NM_018335 | C14ORF131 | CHROMOSOME 14 OPEN READING FRAME 131 |
| NM_138385 | TMEM129 | TRANSMEMBRANE PROTEIN 129 |
| NM_001823 | CKB | CREATINE KINASE, BRAIN |
| NM_004440 | EPHA7 | EPH RECEPTOR A7 |
| NM_006779 | CDC42EP2 | CDC42 EFFECTOR PROTEIN (RHO GTPASE BINDING) 2 |
| NM_007162 | TFEB | TRANSCRIPTION FACTOR EB |
| NM_014248 | RBX1 | RING-BOX 1 |
| NM_016267 | VGLL1 | VESTIGIAL LIKE 1 (*DROSOPHILA*) |
| NM_181656 | C17ORF58 | CHROMOSOME 17 OPEN READING FRAME 58 |
| NM_138482 | | hypothetical protein BC009264 |
| BC026345 | KIAA1189 | KIAA1189 |
| NM_032315 | SLC25A33 | PNC1 PROTEIN |
| NM_002944 | ROS1 | V-ROS UR2 SARCOMA VIRUS ONCOGENE HOMOLOG 1 (AVIAN) |
| BC017048 | GJB2 | GAP JUNCTION PROTEIN, BETA 2, 26 KDA (CONNEXIN 26) |
| BC039814 | ZRANB2 | ZINC FINGER PROTEIN 265 |
| NM_001044 | SLC6A3 | SOLUTE CARRIER FAMILY 6 (NEUROTRANSMITTER TRANSPORTER, DOPAMINE), MEMBER 3 |
| NM_138470 | | hypothetical protein BC008131 |
| NM_005084 | PLA2G7 | PHOSPHOLIPASE A2, GROUP VII (PLATELET-ACTIVATING FACTOR ACETYLHYDROLASE, PLASMA) |
| BC012499 | SIRT1 | SIRTUIN (SILENT MATING TYPE INFORMATION REGULATION 2 HOMOLOG) 1 (*S. CEREVISIAE*) |
| BC045532 | LSM8 | LSM8 HOMOLOG, U6 SMALL NUCLEAR RNA ASSOCIATED (*S. CEREVISIAE*) |
| NM_003295 | TPT1 | TUMOR PROTEIN, TRANSLATIONALLY-CONTROLLED 1 |
| NM_006912 | RIT1 | RAS-LIKE WITHOUT CAAX 1 |
| NM_014184 | CNIH4 | CORNICHON HOMOLOG 4 (*DROSOPHILA*) |
| BC003065 | CDK2 | CYCLIN-DEPENDENT KINASE 2 |
| BC009793 | ERCC8 | EXCISION REPAIR CROSS-COMPLEMENTING RODENT REPAIR DEFICIENCY, COMPLEMENTATION GROUP 8 |
| NM_005114 | HS3ST1 | HEPARAN SULFATE (GLUCOSAMINE) 3-O-SULFOTRANSFERASE 1 |
| NM_018129 | PNPO | PYRIDOXINE 5'-PHOSPHATE OXIDASE |
| NM_152285 | ARRDC1 | ARRESTIN DOMAIN CONTAINING 1 |
| BC009710 | GOSR2 | GOLGI SNAP RECEPTOR COMPLEX MEMBER 2 |
| NM_015966 | ERGIC3 | ERGIC AND GOLGI 3 |
| NM_020370 | GPR84 | G PROTEIN-COUPLED RECEPTOR 84 |
| NM_130398 | EXO1 | EXONUCLEASE 1 |
| NM_145865 | ANKS4B | ANKYRIN REPEAT AND STERILE ALPHA MOTIF DOMAIN CONTAINING 4B |
| BC001234 | LOH11CR2A | LOSS OF HETEROZYGOSITY, 11, CHROMOSOMAL REGION 2, GENE A |
| BC062625 | SLC39A4 | SOLUTE CARRIER FAMILY 39 (ZINC TRANSPORTER), MEMBER 4 |
| BC001889 | NAPG | N-ETHYLMALEIMIDE-SENSITIVE FACTOR ATTACHMENT PROTEIN, GAMMA |
| BC013768 | PCCB | PROPIONYL COENZYME A CARBOXYLASE, BETA POLYPEPTIDE |
| BC020651 | MRPL35 | MITOCHONDRIAL RIBOSOMAL PROTEIN L35 |
| BC051291 | RDH11 | RETINOL DEHYDROGENASE 11 (ALL-TRANS AND 9-CIS) |
| BC069328 | BMF | BCL2 MODIFYING FACTOR |
| NM_006426 | DPYSL4 | DIHYDROPYRIMIDINASE-LIKE 4 |
| NM_178863 | KCTD13 | POTASSIUM CHANNEL TETRAMERISATION DOMAIN CONTAINING 13 |
| BC004176 | SSH3 | SLINGSHOT HOMOLOG 3 (*DROSOPHILA*) |
| BC008790 | GSTM3 | GLUTATHIONE S-TRANSFERASE M3 (BRAIN) |
| BC010176 | NY-SAR-48 | SARCOMA ANTIGEN NY-SAR-48 |
| BC020885 | C12ORF65 | HYPOTHETICAL PROTEIN FLJ38663 |
| BC034554 | SERPINA3 | SERPIN PEPTIDASE INHIBITOR, CLADE A (ALPHA-1 ANTIPROTEINASE, ANTITRYPSIN), MEMBER 3 |
| NM_000394 | CRYAA | CRYSTALLIN, ALPHA A |
| NM_078476 | BTN2A1 | BUTYROPHILIN, SUBFAMILY 2, MEMBER A1 |
| BC015904 | MRPL10 | MITOCHONDRIAL RIBOSOMAL PROTEIN L10 |
| BC019039 | RGS3 | REGULATOR OF G-PROTEIN SIGNALLING 3 |
| BC067445 | DAB1 | DISABLED HOMOLOG 1 (*DROSOPHILA*) |

TABLE 6-continued

| GenBank Accession | Gene Symbol | Name |
|---|---|---|
| NM_003221 | TFAP2B | TRANSCRIPTION FACTOR AP-2 BETA (ACTIVATING ENHANCER BINDING PROTEIN 2 BETA) |
| NM_015959 | TXNDC14 | THIOREDOXIN DOMAIN CONTAINING 14 |
| BC010033 | QPRT | QUINOLINATE PHOSPHORIBOSYLTRANSFERASE (NICOTINATE-NUCLEOTIDE PYROPHOSPHORYLASE (CARBOXYLATING)) |
| NM_152522 | ARL6IP6 | ADP-RIBOSYLATION-LIKE FACTOR 6 INTERACTING PROTEIN 6 |
| BC019254 | ENOX2 | CYTOSOLIC OVARIAN CARCINOMA ANTIGEN 1 |
| NM_012148 | DUX3 | DOUBLE HOMEOBOX, 3 |
| NM_025004 | CCDC15 | COILED-COIL DOMAIN CONTAINING 15 |
| BC017475 | TTC15 | TETRATRICOPEPTIDE REPEAT DOMAIN 15 |
| NM_172211 | CSF1 | COLONY STIMULATING FACTOR 1 (MACROPHAGE) |
| BC007862 | GPR108 | G PROTEIN-COUPLED RECEPTOR 108 |
| BC010850 | HEATR2 | HYPOTHETICAL PROTEIN FLJ20397 |
| NM_016009 | SH3GLB1 | SH3-DOMAIN GRB2-LIKE ENDOPHILIN B1 |
| NM_152328 | ADSSL1 | ADENYLOSUCCINATE SYNTHASE LIKE 1 |
| BC020867 | SLC6A13 | SOLUTE CARRIER FAMILY 6 (NEUROTRANSMITTER TRANSPORTER, GABA), MEMBER 13 |
| NM_178126 | FAM134C | HYPOTHETICAL PROTEIN LOC162427 |
| NM_007241 | SNF8 | SNF8, ESCRT-II COMPLEX SUBUNIT, HOMOLOG (*S. CEREVISIAE*) |
| NM_016440 | VRK3 | VACCINIA RELATED KINASE 3 |
| BC035314 | BXDC1 | BRIX DOMAIN CONTAINING 1 |
| NM_030881 | DDX17 | DEAD (ASP-GLU-ALA-ASP) BOX POLYPEPTIDE 17 |
| NM_001033578 | SGK3 | SERUM/GLUCOCORTICOID REGULATED KINASE FAMILY, MEMBER 3 |
| BC010155 | FDX1L | SIMILAR TO RIKEN CDNA B230118G17 GENE |
| NM_018667 | SMPD3 | SPHINGOMYELIN PHOSPHODIESTERASE 3, NEUTRAL MEMBRANE (NEUTRAL SPHINGOMYELINASE II) |
| NM_017812 | CHCHD3 | COILED-COIL-HELIX-COILED-COIL-HELIX DOMAIN CONTAINING 3 |
| NM_001613 | ACTG2 | ACTIN, ALPHA 2, SMOOTH MUSCLE, AORTA |
| BC031329 | TMEM149 | U2(RNU2) SMALL NUCLEAR RNA AUXILIARY FACTOR 1-LIKE 4 |
| BC039256 | PDS5B | ANDROGEN-INDUCED PROLIFERATION INHIBITOR |
| NM_017634 | KCTD9 | POTASSIUM CHANNEL TETRAMERISATION DOMAIN CONTAINING 9 |
| NM_001017980 | LOC203547 | HYPOTHETICAL PROTEIN LOC203547 |
| BC053320 | CTBP1 | C-TERMINAL BINDING PROTEIN 1 |
| NM_152619 | DCLK2 | DOUBLECORTIN AND CAM KINASE-LIKE 2 |
| BC033668 | ARHGAP28 | KIAA1314 PROTEIN |
| BC059396 | FAM92A3 | FAMILY WITH SEQUENCE SIMILARITY 92, MEMBER A3 |
| NM_080660 | ZC3HAV1L | SIMILAR TO RIKEN CDNA 1200014N16 GENE |
| BC003551 | TGM2 | TRANSGLUTAMINASE 2 (C POLYPEPTIDE, PROTEIN-GLUTAMINE-GAMMA-GLUTAMYLTRANSFERASE) |
| NM_172341 | LIN37 | PRESENILIN ENHANCER 2 HOMOLOG (*C. ELEGANS*) |
| NM_005158 | ABL2 | V-ABL ABELSON MURINE LEUKEMIA VIRAL ONCOGENE HOMOLOG 2 (ARG, ABELSON-RELATED GENE) |
| NM_005558 | LAD1 | LADININ 1 |
| NM_000624 | SERPINA5 | SERPIN PEPTIDASE INHIBITOR, CLADE A (ALPHA-1 ANTIPROTEINASE, ANTITRYPSIN), MEMBER 5 |
| NM_173799 | VSTM3 | V-SET AND IMMUNOGLOBULIN DOMAIN CONTAINING 9 |
| NM_003592 | CUL1 | CULLIN 1 |
| BC017594 | APIP | APAF1 INTERACTING PROTEIN |
| NM_032498 | RHOXF2 | PEPP SUBFAMILY GENE 2 |
| BC008730 | HK1 | HEXOKINASE 1 |
| BC016276 | DLG7 | DISCS, LARGE HOMOLOG 7 (*DROSOPHILA*) |
| BC033708 | RALGPS1 | RAL GEF WITH PH DOMAIN AND SH3 BINDING MOTIF 1 |
| BC051000 | TCL1B | T-CELL LEUKEMIA/LYMPHOMA 1B |
| BC066974 | NA | HYPOTHETICAL PROTEIN |
| BC022983 | LNX1 | LIGAND OF NUMB-PROTEIN X 1 |
| NM_003256 | TIMP4 | TIMP METALLOPEPTIDASE INHIBITOR 4 |
| NM_003674 | CDK10 | CYCLIN-DEPENDENT KINASE (CDC2-LIKE) 10 |
| BC004549 | DUS3L | DIHYDROURIDINE SYNTHASE 3-LIKE (*S. CEREVISIAE*) |
| BC015596* | C21ORF51 | CHROMOSOME 21 OPEN READING FRAME 51 |
| BC018206* | FAM128B | HYPOTHETICAL PROTEIN FLJ14346 |
| BC018722* | ASPSCR1 | ALVEOLAR SOFT PART SARCOMA CHROMOSOME REGION, CANDIDATE 1 |
| BC022357* | RPL17 | RIBOSOMAL PROTEIN L17 |
| BC023152* | GYG2 | GLYCOGENIN 2 |
| BC025700* | AFF4 | AF4/FMR2 FAMILY, MEMBER 4 |
| BC032825* | SH3GL2 | SH3-DOMAIN GRB2-LIKE 2 |

TABLE 6-continued

| GenBank Accession | Gene Symbol | Name |
|---|---|---|
| BC038838* | PRR16 | MESENCHYMAL STEM CELL PROTEIN DSC54 |
| BC052805* | EPB49 | ERYTHROCYTE MEMBRANE PROTEIN BAND 4.9 (DEMATIN) |
| BC056415* | RPAP3 | HYPOTHETICAL PROTEIN FLJ21908 |
| BC065370* | C20ORF112 | CHROMOSOME 20 OPEN READING FRAME 112 |
| NM_001032296* | STK24 | SERINE/THREONINE KINASE 24 (STE20 HOMOLOG, YEAST) |
| NM_002498* | NEK3 | NIMA (NEVER IN MITOSIS GENE A)-RELATED KINASE 3 |
| NM_002624* | PFDN5 | PREFOLDIN SUBUNIT 5 |
| NM_004329* | BMPR1A | BONE MORPHOGENETIC PROTEIN RECEPTOR, TYPE IA |
| NM_014245* | RNF7 | RING FINGER PROTEIN 7 |
| NM_014548* | TMOD2 | TROPOMODULIN 2 (NEURONAL) |
| NM_015646* | RAP1B | RAP1B, MEMBER OF RAS ONCOGENE FAMILY |
| NM_017949* | CUEDC1 | CUE DOMAIN CONTAINING 1 |
| NM_018393* | TCP11L1 | T-COMPLEX 11 (MOUSE) LIKE 1 |
| NM_018679* | TCP11 | T-COMPLEX 11 (MOUSE) |
| NM_024591* | CHMP6 | CHROMATIN MODIFYING PROTEIN 6 |
| NM_032368* | LZIC | LEUCINE ZIPPER AND CTNNBIP1 DOMAIN CONTAINING |
| NM_033118* | MYLK2 | MYOSIN LIGHT CHAIN KINASE 2, SKELETAL MUSCLE |
| NM_130807* | MOBKL2A | MOB1, MPS ONE BINDER KINASE ACTIVATOR-LIKE 2A (YEAST) |
| NM_145173* | DIRAS1 | DIRAS FAMILY, GTP-BINDING RAS-LIKE 1 |
| NM_152376* | UBXD3 | UBX DOMAIN CONTAINING 3 |
| NM_182493* | MLCK | MLCK PROTEIN |
| BC056907* | NA | NA |
| SUMO1 | | |
| BC033766 | NDUFV3 | NADH DEHYDROGENASE (UBIQUINONE) FLAVOPROTEIN 3, 10 KDA |
| NM_001312 | CRIP2 | CYSTEINE-RICH PROTEIN 2 |
| NM_004111 | FEN1 | FLAP STRUCTURE-SPECIFIC ENDONUCLEASE 1 |
| NM_000805 | GAST | GASTRIN |
| NM_030645 | SH3BP5L | SH3-BINDING DOMAIN PROTEIN 5-LIKE |
| BC019337 | IGHG1 | IMMUNOGLOBULIN HEAVY CONSTANT GAMMA 1 (G1M MARKER) |
| BC056673 | PPP1R2P9 | PROTEIN PHOSPHATASE 1, REGULATORY (INHIBITOR) SUBUNIT 2 PSEUDOGENE 9 |
| BC054520 | MEF2D | MADS BOX TRANSCRIPTION ENHANCER FACTOR 2, POLYPEPTIDE D (MYOCYTE ENHANCER FACTOR 2D) |
| NM_006902 | PRRX1 | PAIRED RELATED HOMEOBOX 1 |
| NM_004436 | ENSA | ENDOSULFINE ALPHA |
| NM_006255 | PRKCH | PROTEIN KINASE C, ETA |
| NM_007080 | LSM6 | LSM6 HOMOLOG, U6 SMALL NUCLEAR RNA ASSOCIATED (*S. CEREVISIAE*) |
| NM_000860 | HPGD | HYDROXYPROSTAGLANDIN DEHYDROGENASE 15-(NAD) |
| NM_144679 | C17ORF56 | CHROMOSOME 17 OPEN READING FRAME 56 |
| NM_017431 | PRKAG3 | PROTEIN KINASE, AMP-ACTIVATED, GAMMA 3 NON-CATALYTIC SUBUNIT |
| NM_031473 | IFT81 | INTRAFLAGELLAR TRANSPORT 81 HOMOLOG (*CHLAMYDOMONAS*) |
| BC064593 | DCP2 | DCP2 DECAPPING ENZYME HOMOLOG (*S. CEREVISIAE*) |
| BC007347 | CHD2 | CHROMODOMAIN HELICASE DNA BINDING PROTEIN 2 |
| BC003690 | IPO4 | IMPORTIN 4 |
| BC016327 | NUP62CL | HYPOTHETICAL PROTEIN FLJ20130 |
| NM_080600 | MAG | MYELIN ASSOCIATED GLYCOPROTEIN |
| BC017258 | MCM2 | MCM2 MINICHROMOSOME MAINTENANCE DEFICIENT 2, MITOTIN (*S. CEREVISIAE*) |
| NM_017785 | CCDC99 | HYPOTHETICAL PROTEIN FLJ20364 |
| BC000809 | TCEAL1 | TRANSCRIPTION ELONGATION FACTOR A (SII)-LIKE 1 |
| NM_000485 | APRT | ADENINE PHOSPHORIBOSYLTRANSFERASE |
| NM_138820 | HIGD2A | HIG1 DOMAIN FAMILY, MEMBER 2A |
| BC009415 | KIF26A | KINESIN FAMILY MEMBER 26A |
| BC017440 | TRAPPC2L | HEMATOPOIETIC STEM/PROGENITOR CELLS 176 |
| NM_001092 | ABR | ACTIVE BCR-RELATED GENE |
| BC013352 | HTF9C | HPAII TINY FRAGMENTS LOCUS 9C |
| NM_021947 | SRR | SERINE RACEMASE |
| BC011585 | PRKCDBP | PROTEIN KINASE C, DELTA BINDING PROTEIN |
| BC052600 | ZNF718 | ZINC FINGER PROTEIN 718 |
| BC004518 | SYT17 | SYNAPTOTAGMIN XVII |
| NM_178509 | STXBP4 | SYNTAXIN BINDING PROTEIN 4 |

TABLE 6-continued

| GenBank Accession | Gene Symbol | Name |
|---|---|---|
| BC017770 | NA | NA |
| BC066938 | DDX43 | DEAD (ASP-GLU-ALA-ASP) (SEQ ID NO: 2) BOX POLYPEPTIDE 43 |
| BC000393 | FAM127B | DKFZP564B147 PROTEIN |
| BC025787 | ALKBH1 | ALKB, ALKYLATION REPAIR HOMOLOG 1 (*E. COLI*) |
| BC015944 | TIA1 | TIA1 CYTOTOXIC GRANULE-ASSOCIATED RNA BINDING PROTEIN |
| NM_017988 | SCYL2 | SCY1-LIKE 2 (*S. CEREVISIAE*) |
| NM_002020 | FLT4 | FMS-RELATED TYROSINE KINASE 4 |
| NM_031472 | TRPT1 | TRNA PHOSPHOTRANSFERASE 1 |
| BC001728* | TFPT | TCF3 (E2A) FUSION PARTNER (IN CHILDHOOD LEUKEMIA) |
| BC003566* | ZNF24 | ZINC FINGER PROTEIN 24 (KOX 17) |
| BC005383* | CETN3 | CENTRIN, EF-HAND PROTEIN, 3 (CDC31 HOMOLOG, YEAST) |
| BC007048* | ZMYM5 | ZINC FINGER, MYM-TYPE 5 |
| BC010125* | C3ORF37 | CHROMOSOME 3 OPEN READING FRAME 37 |
| BC011804* | C1ORF165 | CHROMOSOME 1 OPEN READING FRAME 165 |
| BC015803* | IRF2 | INTERFERON REGULATORY FACTOR 2 |
| BC017314* | ETS1 | V-ETS ERYTHROBLASTOSIS VIRUS E26 ONCOGENE HOMOLOG 1 (AVIAN) |
| BC036335* | BTBD12 | BTB (POZ) DOMAIN CONTAINING 12 |
| BC036572* | ZCCHC12 | ZINC FINGER, CCHC DOMAIN CONTAINING 12 |
| BC051688* | FLJ10781 | HYPOTHETICAL PROTEIN FLJ10781 |
| BC056402* | LOC144097 | HYPOTHETICAL PROTEIN BC007540 |
| BC067299* | MDM4 | MDM4, TRANSFORMED 3T3 CELL DOUBLE MINUTE 4, P53 BINDING PROTEIN (MOUSE) |
| NM_000176* | NR3C1 | NUCLEAR RECEPTOR SUBFAMILY 3, GROUP C, MEMBER 1 (GLUCOCORTICOID RECEPTOR) |
| NM_001008239* | C18ORF25 | CHROMOSOME 18 OPEN READING FRAME 25 |
| NM_001722* | POLR3D | POLYMERASE (RNA) III (DNA DIRECTED) POLYPEPTIDE D, 44 KDA |
| NM_001895* | CSNK2A1 | CASEIN KINASE 2, ALPHA 1 POLYPEPTIDE |
| NM_002739* | PRKCG | PROTEIN KINASE C, GAMMA |
| NM_002938* | RNF4 | RING FINGER PROTEIN 4 |
| NM_003141* | TRIM21 | TRIPARTITE MOTIF-CONTAINING 21 |
| NM_003345* | UBE2I | UBIQUITIN-CONJUGATING ENZYME E2I (UBC9 HOMOLOG, YEAST) |
| NM_003352* | SUMO1 | SMT3 SUPPRESSOR OF MIF TWO 3 HOMOLOG 1 (YEAST) |
| NM_004454* | ETV5 | ETS VARIANT GENE 5 (ETS-RELATED MOLECULE) |
| NM_006977* | ZBTB25 | ZINC FINGER AND BTB DOMAIN CONTAINING 25 |
| NM_014720* | SLK | STE20-LIKE KINASE (YEAST) |
| NM_032141* | CCDC55 | COILED-COIL DOMAIN CONTAINING 55 |
| NM_145796* | POGZ | POGO TRANSPOSABLE ELEMENT WITH ZNF DOMAIN |
| NM_175907* | ZADH2 | HYPOTHETICAL PROTEIN BC010734 |
| NM_212540* | E2F6 | E2F TRANSCRIPTION FACTOR 6 |
| UFM1 | | |
| NM_005879 | TRAIP | TRAF INTERACTING PROTEIN |
| NM_001018 | RPS15 | RIBOSOMAL PROTEIN S15 |
| NM_013974 | DDAH2 | DIMETHYLARGININE DIMETHYLAMINOHYDROLASE 2 |
| NM_001278 | CHUK | CONSERVED HELIX-LOOP-HELIX UBIQUITOUS KINASE |
| BC012611 | EIF4E | EUKARYOTIC TRANSLATION INITIATION FACTOR 4E |
| NM_006819 | STIP1 | STRESS-INDUCED-PHOSPHOPROTEIN 1 (HSP70/HSP90-ORGANIZING PROTEIN) |
| NM_024647 | NUP43 | NUCLEOPORIN 43 KDA |
| NM_007045 | FGFR1OP | FGFR1 ONCOGENE PARTNER |
| NM_014460 | CSDC2 | COLD SHOCK DOMAIN CONTAINING C2, RNA BINDING |
| NM_021260 | ZFYVE1 | ZINC FINGER, FYVE DOMAIN CONTAINING 1 |
| NM_017437 | CPSF2 | CLEAVAGE AND POLYADENYLATION SPECIFIC FACTOR 2, 100 KDA |
| NM_138722 | BCL2L14 | BCL2-LIKE 14 (APOPTOSIS FACILITATOR) |
| NM_016059 | PPIL1 | PEPTIDYLPROLYL ISOMERASE (CYCLOPHILIN)-LIKE 1 |
| NM_020139 | BDH2 | 3-HYDROXYBUTYRATE DEHYDROGENASE, TYPE 2 |
| NM_182493 | MLCK | MLCK PROTEIN |
| BC000578 | HPRT1 | HYPOXANTHINE PHOSPHORIBOSYLTRANSFERASE 1 (LESCH-NYHAN SYNDROME) |
| BC060785 | TRIM40 | TRIPARTITE MOTIF-CONTAINING 40 |
| BC003132 | NUDC | NUCLEAR DISTRIBUTION GENE C HOMOLOG (*A. NIDULANS*) |
| NM_031219 | HDHD3 | HALOACID DEHALOGENASE-LIKE HYDROLASE DOMAIN CONTAINING 3 |

TABLE 6-continued

| GenBank Accession | Gene Symbol | Name |
|---|---|---|
| NM_002358 | MAD2L1 | MAD2 MITOTIC ARREST DEFICIENT-LIKE 1 (YEAST) |
| NM_006578 | GNB5 | GUANINE NUCLEOTIDE BINDING PROTEIN (G PROTEIN), BETA 5 |
| NM_004064 | CDKN1B | CYCLIN-DEPENDENT KINASE INHIBITOR 1B (P27, KIP1) |
| BC030280 | KIAA0513 | KIAA0513 |
| NM_005338 | HIP1 | HUNTINGTIN INTERACTING PROTEIN 1 |
| NM_004881 | TP53I3 | TUMOR PROTEIN P53 INDUCIBLE PROTEIN 3 |
| BC015395 | CCDC148 | HYPOTHETICAL PROTEIN BC015395 |
| NM_000394 | CRYAA | CRYSTALLIN, ALPHA A |
| BC005955 | C8ORF53 | CHROMOSOME 8 OPEN READING FRAME 53 |
| BC001327 | IFRD2 | INTERFERON-RELATED DEVELOPMENTAL REGULATOR 2 |
| BC021551 | NFATC2IP | NUCLEAR FACTOR OF ACTIVATED T-CELLS, CYTOPLASMIC, CALCINEURIN-DEPENDENT 2 INTERACTING PROTEIN |
| BC050537 | FLJ20160 | FLJ20160 PROTEIN |
| BC058862 | TSKS | TESTIS-SPECIFIC KINASE SUBSTRATE |
| NM_005235 | ERBB4 | V-ERB-A ERYTHROBLASTIC LEUKEMIA VIRAL ONCOGENE HOMOLOG 4 (AVIAN) |
| NM_014012 | REM1 | RAS (RAD AND GEM)-LIKE GTP-BINDING 1 |
| NM_022110 | FKBPL | FK506 BINDING PROTEIN LIKE |
| NM_006147 | IRF6 | INTERFERON REGULATORY FACTOR 6 |
| NM_001349 | DARS | ASPARTYL-TRNA SYNTHETASE |
| BC064945 | SCYL1BP1 | SCY1-LIKE 1 BINDING PROTEIN 1 |
| NM_032385 | C5ORF4 | CHROMOSOME 5 OPEN READING FRAME 4 |
| NM_172037 | RDH10 | RETINOL DEHYDROGENASE 10 (ALL-TRANS) |
| NM_173621 | C17ORF44 | CHROMOSOME 17 OPEN READING FRAME 44 |
| NM_004074 | COX8A | CYTOCHROME C OXIDASE SUBUNIT 8A (UBIQUITOUS) |
| NM_022156 | DUS1L | DIHYDROURIDINE SYNTHASE 1-LIKE (*S. CEREVISIAE*) |
| NM_016401 | C11ORF73 | HYPOTHETICAL PROTEIN HSPC138 |
| NM_019617 | GKN1 | GASTROKINE 1 |
| BC054501 | DNM2 | DYNAMIN 2 |
| NM_058173 | MUCL1 | SMALL BREAST EPITHELIAL MUCIN |
| BC032307 | CCDC123 | HYPOTHETICAL PROTEIN FLJ14640 |
| BC034028 | SHARPIN | SHANK-ASSOCIATED RH DOMAIN INTERACTOR |
| BC015202 | CENPT | CHROMOSOME 16 OPEN READING FRAME 56 |
| BC013957 | FAM62B | FAMILY WITH SEQUENCE SIMILARITY 62 (C2 DOMAIN CONTAINING) MEMBER B |
| BC015569 | ARL6IP4 | ADP-RIBOSYLATION-LIKE FACTOR 6 INTERACTING PROTEIN 4 |
| BC020221 | STAC | SH3 AND CYSTEINE RICH DOMAIN |
| BC053895 | IRS1 | INSULIN RECEPTOR SUBSTRATE 1 |
| NM_002748 | MAPK6 | MITOGEN-ACTIVATED PROTEIN KINASE 6 |
| NM_198086 | JUB | JUB, AJUBA HOMOLOG (*XENOPUS LAEVIS*) |
| NM_006621 | AHCYL1 | S-ADENOSYLHOMOCYSTEINE HYDROLASE-LIKE 1 |
| NM_018698 | NXT2 | NUCLEAR TRANSPORT FACTOR 2-LIKE EXPORT FACTOR 2 |
| NM_005034 | POLR2K | POLYMERASE (RNA) II (DNA DIRECTED) POLYPEPTIDE K, 7.0 KDA |
| NM_018438 | FBXO6 | F-BOX PROTEIN 6 |
| NM_033547 | INTS4 | INTEGRATOR COMPLEX SUBUNIT 4 |
| NM_153212 | GJB4 | GAP JUNCTION PROTEIN, BETA 4 (CONNEXIN 30.3) |
| NM_175738 | RAB37 | RAB37, MEMBER RAS ONCOGENE FAMILY |
| BC013031 | PHLDB1 | PLECKSTRIN HOMOLOGY-LIKE DOMAIN, FAMILY B, MEMBER 1 |
| NM_001005465 | OR10G3 | OLFACTORY RECEPTOR, FAMILY 10, SUBFAMILY G, MEMBER 3 |
| NM_001899 | CST4 | CYSTATIN S |
| NM_004753 | DHRS3 | DEHYDROGENASE/REDUCTASE (SDR FAMILY) MEMBER 3 |
| NM_021992 | TMSL8 | THYMOSIN-LIKE 8 |
| NM_197970 | BOLL | BOL, BOULE-LIKE (*DROSOPHILA*) |
| NM_139246 | C9ORF97 | CHROMOSOME 9 OPEN READING FRAME 97 |
| NM_005586 | MDFI | MYOD FAMILY INHIBITOR |
| BC041831 | TLE3 | TRANSDUCIN-LIKE ENHANCER OF SPLIT 3 (E(SP1) HOMOLOG, *DROSOPHILA*) |
| NM_003130 | SRI | SORCIN |
| BC030237 | SLC22A18AS | SOLUTE CARRIER FAMILY 22 (ORGANIC CATION TRANSPORTER), MEMBER 18 ANTISENSE |
| BC053351 | DLX1 | DISTAL-LESS HOMEOBOX 1 |
| BC022034 | LDHAL6B | LACTATE DEHYDROGENASE A-LIKE 6B |
| BC031964 | GLUL | GLUTAMATE-AMMONIA LIGASE (GLUTAMINE SYNTHETASE) |
| NM_032350 | C7ORF50 | HYPOTHETICAL PROTEIN MGC11257 |
| NM_152646 | | hypothetical protein MGC23270 |

TABLE 6-continued

| GenBank Accession | Gene Symbol | Name |
|---|---|---|
| BC024245 | SALL2 | SAL-LIKE 2 (*DROSOPHILA*) |
| NM_001004300 | ZNF720 | ZINC FINGER PROTEIN 720 |
| NM_079422 | MYL1 | MYOSIN, LIGHT POLYPEPTIDE 1, ALKALI; SKELETAL, FAST |
| NM_024295 | DERL1 | DER1-LIKE DOMAIN FAMILY, MEMBER 1 |
| BC026241 | UBE3C | UBIQUITIN PROTEIN LIGASE E3C |
| BC064144 | NA | NA |
| NM_152266 | C19ORF40 | HYPOTHETICAL PROTEIN MGC32020 |
| NM_017722 | TRMT1 | TRM1 TRNA METHYLTRANSFERASE 1 HOMOLOG (*S. CEREVISIAE*) |
| NM_000905 | NPY | NEUROPEPTIDE Y |
| BC001553 | CHMP2B | CHROMATIN MODIFYING PROTEIN 2B |
| NM_006438 | COLEC10 | COLLECTIN SUB-FAMILY MEMBER 10 (C-TYPE LECTIN) |
| NM_014424 | HSPB7 | HEAT SHOCK 27 KDA PROTEIN FAMILY, MEMBER 7 (CARDIOVASCULAR) |
| NM_001179 | ART3 | ADP-RIBOSYLTRANSFERASE 3 |
| NM_020348 | CNNM1 | CYCLIN M1 |
| NM_006928 | SILV | SILVER HOMOLOG (MOUSE) |
| NM_022568 | ALDH8A1 | ALDEHYDE DEHYDROGENASE 8 FAMILY, MEMBER A1 |
| NM_178152 | DCX | DOUBLECORTEX; LISSENCEPHALY, X-LINKED (DOUBLECORTIN) |
| NM_153822 | PSMD4 | PROTEASOME (PROSOME, MACROPAIN) 26S SUBUNIT, NON-ATPASE, 4 |
| NM_001699 | AXL | AXL RECEPTOR TYROSINE KINASE |
| BC006195 | ACLY | ATP CITRATE LYASE |
| NM_020397 | CAMK1D | CALCIUM/CALMODULIN-DEPENDENT PROTEIN KINASE ID |
| BC017249 | ENO3 | ENOLASE 1, (ALPHA) |
| BC001600 | CDC123 | CHROMOSOME 10 OPEN READING FRAME 7 |
| NM_024770 | METTL8 | HYPOTHETICAL PROTEIN FLJ13984 |
| NM_194270 | MORN2 | MORN REPEAT CONTAINING 2 |
| NM_022650 | RASA1 | RAS P21 PROTEIN ACTIVATOR (GTPASE ACTIVATING PROTEIN) 1 |
| BC005830 | ANXA9 | ANNEXIN A9 |
| NM_014065 | ASTE1 | ASTEROID HOMOLOG 1 (*DROSOPHILA*) |
| BC014244 | RTN2 | RETICULON 2 |
| BC024002 | FNDC8 | FIBRONECTIN TYPE III DOMAIN CONTAINING 8 |
| NM_178034 | PLA2G4D | PHOSPHOLIPASE A2, GROUP IVD (CYTOSOLIC) |
| BC025266 | TASP1 | TASPASE, THREONINE ASPARTASE, 1 |
| NM_003928 | FAM127A | CAAX BOX 1 |
| NM_017819 | LOC131909 | RNA (GUANINE-9-) METHYLTRANSFERASE DOMAIN CONTAINING 1 |
| NM_018158 | SLC4A1AP | SOLUTE CARRIER FAMILY 4 (ANION EXCHANGER), MEMBER 1, ADAPTOR PROTEIN |
| NM_175571 | GIMAP8 | GTPASE, IMAP FAMILY MEMBER 8 |
| BC000453 | PCM1 | PERICENTRIOLAR MATERIAL 1 |
| NM_000910 | NPY2R | NEUROPEPTIDE Y RECEPTOR Y2 |
| NM_018679 | TCP11 | T-COMPLEX 11 (MOUSE) |
| NM_022559 | GH1 | CHORIONIC SOMATOMAMMOTROPIN HORMONE 1 (PLACENTAL LACTOGEN) |
| BC030957 | ANK1 | ANKYRIN 1, ERYTHROCYTIC |
| NM_003168 | SUPT4H1 | SUPPRESSOR OF TY 4 HOMOLOG 1 (*S. CEREVISIAE*) |
| BC012095 | BST1 | BONE MARROW STROMAL CELL ANTIGEN 1 |
| BC013740 | SLC2A6 | SOLUTE CARRIER FAMILY 2 (FACILITATED GLUCOSE TRANSPORTER), MEMBER 6 |
| NM_016505 | ZCCHC17 | ZINC FINGER, CCHC DOMAIN CONTAINING 17 |
| NM_018697 | LANCL2 | LANC LANTIBIOTIC SYNTHETASE COMPONENT C-LIKE 2 (BACTERIAL) |
| NM_152619 | DCLK2 | DOUBLECORTIN AND CAM KINASE-LIKE 2 |
| NM_152770 | C4ORF22 | HYPOTHETICAL PROTEIN MGC35043 |
| NM_004401 | DFFA | DNA FRAGMENTATION FACTOR, 45 KDA, ALPHA POLYPEPTIDE |
| NM_030636 | EEPD1 | KIAA1706 PROTEIN |
| BC014260 | PARP3 | POLY (ADP-RIBOSE) POLYMERASE FAMILY, MEMBER 3 |
| BC009010 | C6ORF142 | CHROMOSOME 6 OPEN READING FRAME 142 |
| BC047722 | C2ORF64 | HYPOTHETICAL PROTEIN MGC52110 |
| NM_080873 | ASB11 | ANKYRIN REPEAT AND SOCS BOX-CONTAINING 11 |
| NM_173547 | TRIM65 | TRIPARTITE MOTIF-CONTAINING 65 |
| BC041668 | RIPK3 | RECEPTOR-INTERACTING SERINE-THREONINE KINASE 3 |
| BC033728 | NA | NA |
| BC048217 | SPATA5 | SPERMATOGENESIS ASSOCIATED 5 |
| NM_001001852 | PIM3 | PIM-3 ONCOGENE |
| NM_002904 | RDBP | RD RNA BINDING PROTEIN |
| BC030608 | PODN | PODOCAN |

TABLE 6-continued

| GenBank Accession | Gene Symbol | Name |
|---|---|---|
| BC023982 | C5ORF32 | PUTATIVE NUCLEAR PROTEIN ORF1-FL49 |
| NM_133332 | WHSC1 | WOLF-HIRSCHHORN SYNDROME CANDIDATE 1 |
| NM_004040 | RHOB | RAS HOMOLOG GENE FAMILY, MEMBER B |
| BC033708 | RALGPS1 | RAL GEF WITH PH DOMAIN AND SH3 BINDING MOTIF 1 |
| NM_002491 | NDUFB3 | NADH DEHYDROGENASE (UBIQUINONE) 1 BETA SUBCOMPLEX, 3, 12 KDA |
| BC015944 | TIA1 | TIA1 CYTOTOXIC GRANULE-ASSOCIATED RNA BINDING PROTEIN |
| BC050688 | RPSA | RIBOSOMAL PROTEIN SA |
| NM_002443 | MSMB | MICROSEMINOPROTEIN, BETA- |
| NM_172314 | IL25 | INTERLEUKIN 17E |
| NM_019845 | RPRM | REPRIMO, TP53 DEPENDENT G2 ARREST MEDIATOR CANDIDATE |
| BC013163 | DCUN1D1 | DCN1, DEFECTIVE IN CULLIN NEDDYLATION 1, DOMAIN CONTAINING 1 (*S. CEREVISIAE*) |
| BC017741 | GTDC1 | PRO0159 PROTEIN |
| BC023152 | GYG2 | GLYCOGENIN 2 |
| NM_005663 | WHSC2 | WOLF-HIRSCHHORN SYNDROME CANDIDATE 2 |
| NM_000214 | JAG1 | JAGGED 1 (ALAGILLE SYNDROME) |
| NM_004403 | DFNA5 | DEAFNESS, AUTOSOMAL DOMINANT 5 |
| NM_022073 | EGLN3 | HYPOTHETICAL PROTEIN FLJ21620 |
| NM_030571 | NDFIP1 | NEDD4 FAMILY INTERACTING PROTEIN 1 |
| NM_145252 | LOC124220 | SIMILAR TO COMMON SALIVARY PROTEIN 1 |
| BC000772 | SIPA1L3 | SIGNAL-INDUCED PROLIFERATION-ASSOCIATED 1 LIKE 3 |
| NM_006579 | EBP | EMOPAMIL BINDING PROTEIN (STEROL ISOMERASE) |
| BC014441 | NSUN4 | NOL1/NOP2/SUN DOMAIN FAMILY, MEMBER 4 |
| BC019902 | CCDC21 | COILED-COIL DOMAIN CONTAINING 21 |
| BC036827 | LILRB2 | LEUKOCYTE IMMUNOGLOBULIN-LIKE RECEPTOR, SUBFAMILY B (WITH TM AND ITIM DOMAINS), MEMBER 2 |
| NM_001680 | FXYD2 | FXYD DOMAIN CONTAINING ION TRANSPORT REGULATOR 2 |
| NM_006439 | MAB21L2 | MAB-21-LIKE 2 (*C. ELEGANS*) |
| NM_032786 | ZC3H10 | ZINC FINGER CCCH-TYPE CONTAINING 10 |
| NM_024613 | PLEKHF2 | PLECKSTRIN HOMOLOGY DOMAIN CONTAINING, FAMILY F (WITH FYVE DOMAIN) MEMBER 2 |
| NM_001752 | CAT | CATALASE |
| NM_152471 | | hypothetical protein MGC17515 |
| NM_152716 | PATL1 | FLJ36874 PROTEIN |
| BC004243 | BCAT2 | BRANCHED CHAIN AMINOTRANSFERASE 2, MITOCHONDRIAL |
| BC056246 | GALNT3 | UDP-N-ACETYL-ALPHA-D-GALACTOSAMINE:POLYPEPTIDE N-ACETYLGALACTOSAMINYLTRANSFERASE 3 (GALNAC-T3) |
| NM_022133 | SNX16 | SORTING NEXIN 16 |
| NM_025221 | KCNIP4 | KV CHANNEL INTERACTING PROTEIN 4 |
| NM_025234 | WDR61 | WD REPEAT DOMAIN 61 |
| BC014649 | GAL3ST1 | GALACTOSE-3-O-SULFOTRANSFERASE 1 |
| NM_002734 | PRKAR1A | PROTEIN KINASE, CAMP-DEPENDENT, REGULATORY, TYPE I, ALPHA (TISSUE SPECIFIC EXTINGUISHER 1) |
| NM_023934 | FUNDC2 | FUN14 DOMAIN CONTAINING 2 |
| NM_145173 | DIRAS1 | DIRAS FAMILY, GTP-BINDING RAS-LIKE 1 |
| NM_020142 | NDUFA4L2 | NADH:UBIQUINONE OXIDOREDUCTASE MLRQ SUBUNIT HOMOLOG |
| NM_016485 | VTA1 | CHROMOSOME 6 OPEN READING FRAME 55 |
| NM_000345 | SNCA | SYNUCLEIN, ALPHA (NON A4 COMPONENT OF AMYLOID PRECURSOR) |
| BC067447 | DAB1 | DISABLED HOMOLOG 1 (*DROSOPHILA*) |
| NM_001010971 | SAMD13 | STERILE ALPHA MOTIF DOMAIN CONTAINING 13 |
| BC022043 | C7ORF36 | CHROMOSOME 7 OPEN READING FRAME 36 |
| BC004233* | TTYH2 | TWEETY HOMOLOG 2 (*DROSOPHILA*) |
| BC017504* | DEF6 | DIFFERENTIALLY EXPRESSED IN FDCP 6 HOMOLOG (MOUSE) |
| BC018206* | FAM128B | HYPOTHETICAL PROTEIN FLJ14346 |
| BC018404* | FGF21 | FIBROBLAST GROWTH FACTOR 21 |
| BC020985* | COASY | COENZYME A SYNTHASE |
| BC031469* | LOC554207 | HYPOTHETICAL LOC554207 |
| BC058924* | UBE2M | UBIQUITIN-CONJUGATING ENZYME E2M (UBC12 HOMOLOG, YEAST) |
| NM_000020* | ACVRL1 | ACTIVIN A RECEPTOR TYPE II-LIKE 1 |
| NM_000154* | GALK1 | GALACTOKINASE 1 |
| NM_001014796* | DDR2 | DISCOIDIN DOMAIN RECEPTOR FAMILY, MEMBER 2 |

TABLE 6-continued

| GenBank Accession | Gene Symbol | Name |
|---|---|---|
| NM_001105* | ACVR1 | ACTIVIN A RECEPTOR, TYPE I |
| NM_001752* | CAT | CATALASE |
| NM_002227* | JAK1 | JANUS KINASE 1 (A PROTEIN TYROSINE KINASE) |
| NM_002498* | NEK3 | NIMA (NEVER IN MITOSIS GENE A)-RELATED KINASE 3 |
| NM_002964* | S100A8 | S100 CALCIUM BINDING PROTEIN A8 (CALGRANULIN A) |
| NM_003063* | SLN | SARCOLIPIN |
| NM_004972* | JAK2 | JANUS KINASE 2 (A PROTEIN TYROSINE KINASE) |
| NM_005036* | PPARA | PEROXISOME PROLIFERATIVE ACTIVATED RECEPTOR, ALPHA |
| NM_005122* | NR1I3 | NUCLEAR RECEPTOR SUBFAMILY 1, GROUP I, MEMBER 3 |
| NM_005123* | NR1H4 | NUCLEAR RECEPTOR SUBFAMILY 1, GROUP H, MEMBER 4 |
| NM_014583* | LMCD1 | LIM AND CYSTEINE-RICH DOMAINS 1 |
| NM_015646* | RAP1B | RAP1B, MEMBER OF RAS ONCOGENE FAMILY |
| NM_016495* | TBC1D7 | TBC1 DOMAIN FAMILY, MEMBER 7 |
| NM_021709* | SIVA1 | CD27-BINDING (SIVA) PROTEIN |
| NM_030572* | C12ORF39 | CHROMOSOME 12 OPEN READING FRAME 39 |
| NM_033360* | KRAS | V-HA-RAS HARVEY RAT SARCOMA VIRAL ONCOGENE HOMOLOG |
| NM_130807* | MOBKL2A | MOB1, MPS ONE BINDER KINASE ACTIVATOR-LIKE 2A (YEAST) |
| NM_145173* | DIRAS1 | DIRAS FAMILY, GTP-BINDING RAS-LIKE 1 |
| NM_173541* | C10ORF91 | CHROMOSOME 10 OPEN READING FRAME 91 |
| BC004233* | NA | NA |
| BC008624* | NA | NA |
| ISG15 | | |
| BC013366* | URP2 | UNC-112 RELATED PROTEIN 2 |
| BC017314* | ETS1 | V-ETS ERYTHROBLASTOSIS VIRUS E26 ONCOGENE HOMOLOG 1 (AVIAN) |
| BC018404* | FGF21 | FIBROBLAST GROWTH FACTOR 21 |
| BC022363* | VPS37A | VACUOLAR PROTEIN SORTING 37A (YEAST) |
| BC024725* | ANKRD50 | ANKYRIN REPEAT DOMAIN 50 |
| BC025307* | PRKD2 | PROTEIN KINASE D2 |
| BC029112* | SAMSN1 | SAM DOMAIN, SH3 DOMAIN AND NUCLEAR LOCALISATION SIGNALS, 1 |
| BC029480* | LOC554203 | HYPOTHETICAL LOC554203 |
| BC035636* | APBB1IP | AMYLOID BETA (A4) PRECURSOR PROTEIN-BINDING, FAMILY B, MEMBER 1 INTERACTING PROTEIN |
| BC038838* | PRR16 | MESENCHYMAL STEM CELL PROTEIN DSC54 |
| BC039244* | NFYA | NUCLEAR TRANSCRIPTION FACTOR Y, ALPHA |
| BC042999* | ASXL2 | ADDITIONAL SEX COMBS LIKE 2 (*DROSOPHILA*) |
| BC062423* | C7ORF41 | HYPOTHETICAL PROTEIN ELLS1 |
| NM_001571* | IRF3 | INTERFERON REGULATORY FACTOR 3 |
| NM_001926* | DEFA6 | DEFENSIN, ALPHA 6, PANETH CELL-SPECIFIC |
| NM_002505* | NFYA | NUCLEAR TRANSCRIPTION FACTOR Y, ALPHA |
| NM_003141* | TRIM21 | TRIPARTITE MOTIF-CONTAINING 21 |
| NM_004304* | ALK | ANAPLASTIC LYMPHOMA KINASE (KI-1) |
| NM_005214* | CTLA4 | CYTOTOXIC T-LYMPHOCYTE-ASSOCIATED PROTEIN 4 |
| NM_005902* | SMAD3 | SMAD, MOTHERS AGAINST DPP HOMOLOG 3 (*DROSOPHILA*) |
| NM_006324* | CFDP1 | CRANIOFACIAL DEVELOPMENT PROTEIN 1 |
| NM_007242* | DDX19B | DEAD (ASP-GLU-ALA-AS) (SEQ ID NO: 2) BOX POLYPEPTIDE 19B |
| NM_012472* | LRRC6 | LEUCINE RICH REPEAT CONTAINING 6 |
| NM_015927* | TGFB1I1 | TRANSFORMING GROWTH FACTOR BETA 1 INDUCED TRANSCRIPT 1 |
| NM_017724* | LRRFIP2 | LEUCINE RICH REPEAT (IN FLII) INTERACTING PROTEIN 2 |
| NM_017855* | ODAM | APIN PROTEIN |
| NM_023112* | OTUB2 | OTU DOMAIN, UBIQUITIN ALDEHYDE BINDING 2 |
| NM_025241* | UBXD1 | UBX DOMAIN CONTAINING 1 |
| NM_053283* | DCD | DERMCIDIN |
| NM_172160* | KCNAB1 | POTASSIUM VOLTAGE-GATED CHANNEL, SHAKER-RELATED SUBFAMILY, BETA MEMBER 1 |
| NM_175907* | ZADH2 | HYPOTHETICAL PROTEIN BC010734 |

The protein targets showing the highest reactivity in a sumo1 PTM assay were the RANBP2 protein, which was previously identified as a sumo1 E3 ligase, and TGFII. In the sumo2/3 PTM profile, one of the top reactivities was UbcH9, the only known E2 characterized to date for sumo conjugation. Additionally, among the highest reactivities (top 7) of neddylated proteins were the E2 and E3 enzymes that are known to be involved in the neddylation pathway. The other reactive proteins did not appear to be relevant to the neddylation pathway. Thus, among the top reacting proteins for each of these modifications were the enzymes that are involved in catalysis of the relevant PTM itself. In the case of FAT10, many of the highly reactive proteins were mitotic regulators or cytoskeleton related. To date only one substrate, Mad2, has been described for modification with FAT10, and indeed Mad2 was highly FATtenylated in this assay. FAT10 is known to be highly expressed in certain kinds of cancers, and its overexpression may lead to chromosomal aberrations as well as mitotic arrest. For UFM1 there are no previously known substrates, and therefore all of the identified UFM1 substrates are newly discovered.

Figure 15:
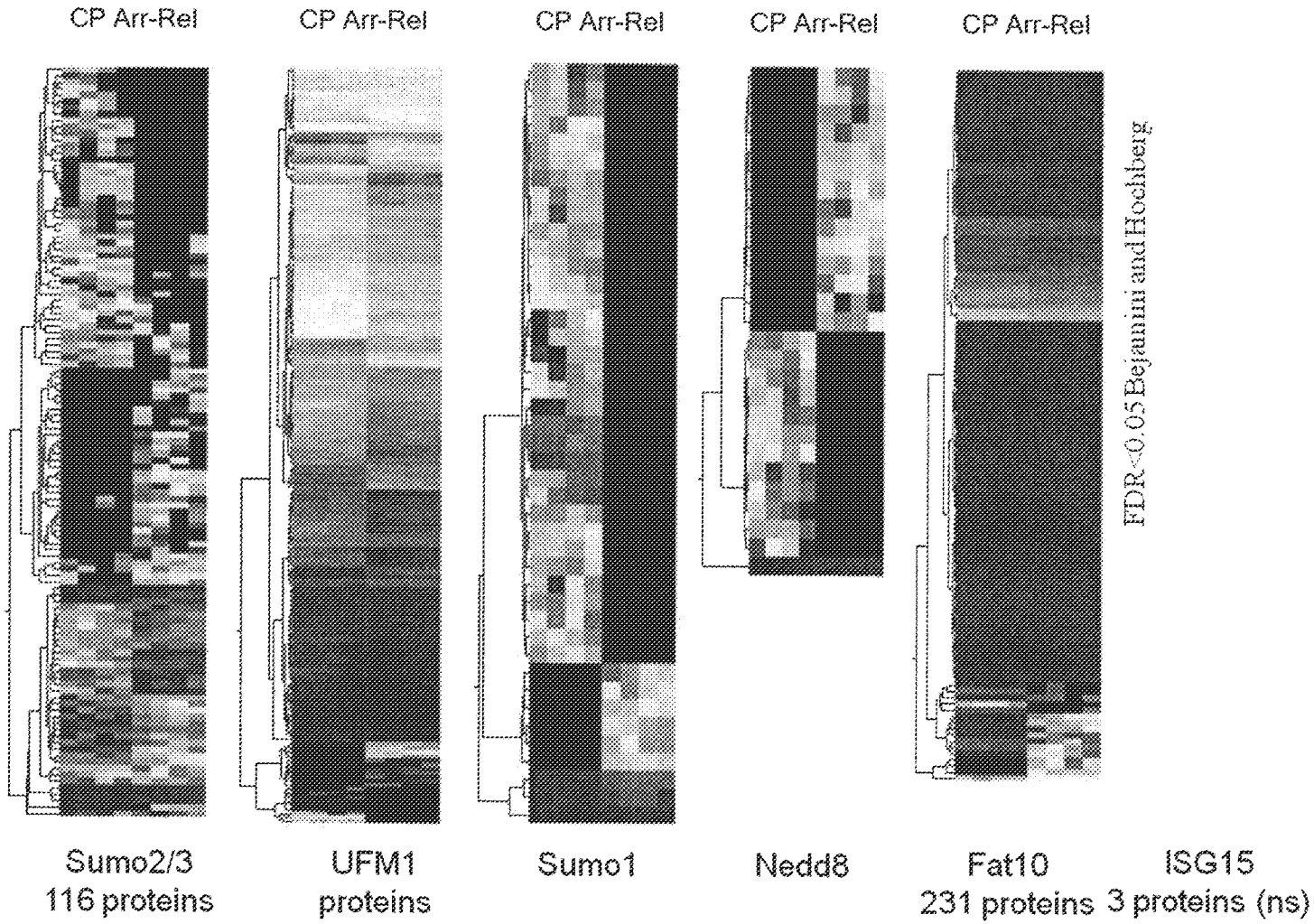
FIG. 15 shows the fluorescence signal obtained for differentially modified proteins on a microarray after the indicated PTM reactions using extracts of mitotic checkpoint arrested and released HeLa S3 cells.
Figure 16:
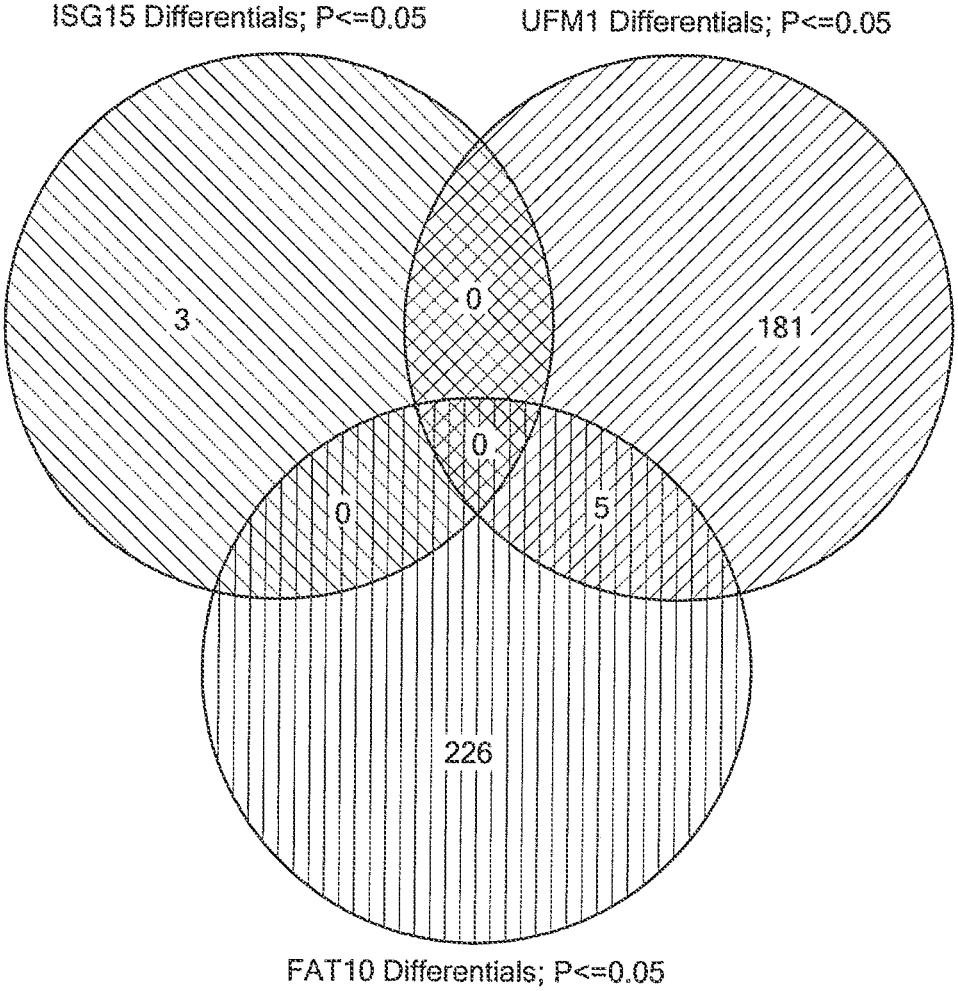
FIG. 16 presents a Venn diagram illustrating the relationships among protein targets found to be modified by different ubiquitin-like modifiers.

For each of the modifying moieties, signals from the CP-arrested and the CP-released extracts were compared. Two microarrays from each condition were examined, and a two-tailed t-test was used to identify differentially modified proteins. To determine significance, a permutation-based p-value calculation was used, and corrected for false discovery rate (FDR) either using Storey's method or using the Hochberg-Benjamini correction. For each modifying moiety tested (i.e. ubiquitin, sumo1, sumo2/3, nedd8, FA10, UFM1, ISG15) the proteins showing significant change in their modification state upon release from the mitotic CP were identified. For each PTM, two biological replicates and two different mitotic conditions (CP-arrested and CP-released) were examined. A subset of the microarray proteins showed a marked difference under the two different conditions but were similar in the biological replicates. These were identified as differentially modified proteins. The data were then clustered based on the differentially modified proteins (FIG. 15). Each row in FIG. 15 represents a different protein that was found to be differentially modified under the two different mitotic conditions. The list of differentially modified proteins was compared for each of the modifications (see Table 7), and the results showed that the proteins were differentially targeted by each of the modifying moieties, and the sets of proteins modified by the different modifying moieties were not overlapping more than would be expected by chance. This is shown in a Venn diagram in FIG. 16, and suggests specialized roles for each different modification in regulating a unique set of target proteins.

REFERENCES

1. M. Rape, S. K. Reddy, M. W. Kirschner, Cell 124, 89 (Jan. 13, 2006).
2. N. G. Ayad, S. Rankin, D. Ooi, M. Rape, M. W. Kirschner, Methods Enzymol 399, 404 (2005).
3. T. J. McGarry, M. W. Kirschner, Cell 93, 1043 (Jun. 12, 1998).
4. R. W. King, K. D. Lustig, P. T. Stukenberg, T. J. McGarry, M. W. Kirschner, Science 277, 973 (Aug. 15, 1997).
5. K. D. Lustig et al., Methods Enzymol 283, 83 (1997).
6. F. Kanai et al., Embo J 19, 6778 (Dec. 15, 2000).
7. Y. H. Oh et al., Biosens Bioelectron 22, 1260 (Feb. 15, 2007).
8. R. Gupta et al., Mol Syst Biol 3, 116 (2007).
9. J. Ptacek et al., Nature 438, 679 (Dec. 1, 2005).
10. C. Schnack, K. M. Danzer, B. Hengerer, F. Gillardon, Neuroscience (Feb. 29, 2008).
11. T. Evans, E. T. Rosenthal, J. Youngblom, D. Distel, T. Hunt, Cell 33, 389 (June, 1983).
12. M. Glotzer, A. W. Murray, M. W. Kirschner, Nature 349, 132 (Jan. 10, 1991).
13. R. W. King et al., Cell 81, 279 (Apr. 21, 1995).
14. G. Fang, H. Yu, M. W. Kirschner, Philos Trans R Soc Lond B Biol Sci 354, 1583 (Sep. 29, 1999).
15. R. W. King, R. J. Deshaies, J. M. Peters, M. W. Kirschner, Science 274, 1652 (Dec. 6, 1996).
16. H. Yu, R. W. King, J. M. Peters, M. W. Kirschner, Curr Biol 6, 455 (Apr. 1, 1996).
17. S. K. Reddy, M. Rape, W. A. Margansky, M. W. Kirschner, Nature 446, 921 (Apr. 19, 2007).
18. D. Verdick, S. Handran, and S. Pickett., p. 83-98. In G. Kamberova (ed.), DNA image analysis: nuts and bolts, DNA Press LLC, Salem, Mass., Key considerations for accurate microarray scanning and image analysis. K. G. (ed), Ed., DNA Array Image Analysis: Nuts and Bolts. (DNA Press LLC: Salem, Mass., 2002), pp. 83-98.
19. J. G. Chafouleas, W. E. Bolton, H. idaka, A. E. Boyd, 3rd, A. R. eans, Cell 28, 41 (January, 1982).
20. J. Roig, A. Mikhailov, C. Belham, J. Avruch, Genes Dev 16, 1640 (Jul. 1, 2002).
21. J. Roig, A. Groen, J. Caldwell, J. Avruch, Mol Biol Cell 16, 4827 (October, 2005).
22. M. J. Kallio, V. A. Beardmore, J. Weinstein, G. J. Gorbsky, J Cell Biol 158, 841 (Sep. 2, 2002).
23. J. W. Raff, K. Jeffers, J. Y. Huang, J Cell Biol 157, 1139 (Jun. 24, 2002).
24. J. Huang, J. W. Raff, Embo J 18, 2184 (Apr. 15, 1999).
25. Y. A. Lam et al., Proc Natl Acad Sci USA 97, 9902 (Aug. 29, 2000).
26. K L. Lim, V. L. Dawson, T. M. Dawson, Neurobiol Aging 27, 524 (April, 2006).
27. J. A. Olzmann, L. S. Chin, Autophagy 4, 85 (January-February, 2008).
28. J. M. Tan et al., Hum Mol Genet 17, 431 (Feb. 1, 2008).
29. S. Adhikary et al., Cell 123, 409 (Nov. 4, 2005).
30. C. L. Brooks, W. Gu, Cell Cycle 3, 895 (July, 2004).
31. A. D. Choudhury, H. Xu, R. Baer, J Biol Chem 279, 33909 (Aug. 6, 2004).
32. B. M. Bolstad, R. A. Irizarry, M. Astrand, T. P. Speed, Bioinformatics 19, 185 (Jan. 22, 2003).
33. Adhikary, S., Marinoni, F., Hock, A., Hulleman, E., Popov, N., Beier, R., Bernard, S., Quarto, M., Capra, M., Goettig, S., et al. 2005. The ubiquitin ligase HectH9 regulates transcriptional activation by Myc and is essential for tumor cell proliferation. Cell 123:409-421.
34. Choudhury, A. D., Xu, H., and Baer, R. 2004. Ubiquitination and proteasomal degradation of the BRCA1 tumor suppressor is regulated during cell cycle progression. J Biol Chem 279:33909-33918.
35. Mo, Y. Y., Yu, Y., Theodosiou, E., Rachel Ee, P. L., and Beck, W. T. 2005. A role for Ubc9 in tumorigenesis. Oncogene 24:2677-2683.
36. Lam, Y. A., Pickart, C. M., Alban, A., Landon, M., Jamieson, C., Ramage, R., Mayer, R. J., and Layfield, R. 2000. Inhibition of the ubiquitin-proteasome system in Alzheimer's disease. Proc Natl Acad Sci USA 97:9902-9906.
37. Wang, J. Z., Grundke-Iqbal, I., and Iqbal, K. 1996. Glycosylation of microtubule-associated protein tau: an abnormal posttranslational modification in Alzheimer's disease. Nat Med 2:871-875.
38. Lim, K. L., Dawson, V. L., and Dawson, T. M. 2006. Parkin-mediated lysine 63-linked polyubiquitination: a link to protein inclusions formation in Parkinson's and other conformational diseases? Neurobiol Aging 27:524-529.

39. Olzmann, J. A., and Chin, L. S. 2008. Parkin-mediated K63-linked polyubiquitination: a signal for targeting misfolded proteins to the aggresome-autophagy pathway. Autophagy 4:85-87.
40. Tan, J. M., Wong, E. S., Kirkpatrick, D. S., Pletnikova, O., Ko, H. S., Tay, S. P., Ho, M. W., Troncoso, J., Gygi, S. P., Lee, M. K., et al. 2008. Lysine 63-linked ubiquitination promotes the formation and autophagic clearance of protein inclusions associated with neurodegenerative diseases. Hum Mol Genet 17:431-439.
41. Abel, T., and Zukin, R. S. 2008. Epigenetic targets of HDAC inhibition in neurodegenerative and psychiatric disorders. Curr Opin Pharmacol 8:57-64.
42. Mori, F., Nishie, M., Piao, Y. S., Kito, K., Kamitani, T., Takahashi, H., and Wakabayashi, K. 2005. Accumulation of NEDD8 in neuronal and glial inclusions of neurodegenerative disorders. Neuropathol Appl Neurobiol 31:53-61.
43. Braunstein, I., Miniowitz, S., Moshe, Y., and Hershko, A. 2007. Inhibitory factors associated with anaphase-promoting complex/cylosome in mitotic checkpoint. Proc Natl Acad Sci USA 104:4870-4875.
44. Ciechanover, A., Finley, D., and Varshaysky, A. 1984. Ubiquitin dependence of selective protein degradation demonstrated in the mammalian cell cycle mutant ts85. Cell 37:57-66.
45. Evans, T., Rosenthal, E. T., Youngblom, J., Distel, D., and Hunt, T. 1983. Cyclin: a protein specified by maternal mRNA in sea urchin eggs that is destroyed at each cleavage division. Cell 33:389-396.
46. Fang, G., Yu, H., and Kirschner, M. W. 1999. Control of mitotic transitions by the anaphase-promoting complex. Philos Trans R Soc Lond B Biol Sci 354:1583-1590.
47. Glotzer, M., Murray, A. W., and Kirschner, M. W. 1991. Cyclin is degraded by the ubiquitin pathway. Nature 349:132-138.
48. King, R. W., Deshaies, R. J., Peters, J. M., and Kirschner, M. W. 1996. How proteolysis drives the cell cycle. Science 274:1652-1659.
49. Reddy, S. K., Rape, M., Margansky, W. A., and Kirschner, M. W. 2007. Ubiquitination by the anaphase-promoting complex drives spindle checkpoint inactivation. Nature 446:921-925.
50. Dery, U., and Masson, J. Y. 2007. Twists and turns in the function of DNA damage signaling and repair proteins by PTMs. DNA Repair (Amst) 6:561-577.
51. Sadri-Vakili, G., and Cha, J. H. 2006. Mechanisms of disease: Histone modifications in Huntington's disease. Nat Clin Pract Neurol 2:330-338.
52. Steffan, J. S., Agrawal, N., Pallos, J., Rockabrand, E., Trotman, L. C., Slepko, N., Illes, K., Lukacsovich, T., Zhu, Y. Z., Cattaneo, E., et al. 2004. SUMO modification of Huntingtin and Huntington's disease pathology. Science 304:100-104.
53. Perkins, N. D. 2006. PTMs regulating the activity and function of the nuclear factor kappa B pathway. Oncogene 25:6717-6730.
54. Takahashi-Fujigasaki, J., Arai, K., Funata, N., and Fujigasaki, H. 2006. SUMOylation substrates in neuronal intranuclear inclusion disease. Neuropathol Appl Neurobiol 32:92-100.
55. Li, M., Guo, D., Isales, C. M., Eizirik, D. L., Atkinson, M., She, J. X., and Wang, C. Y. 2005. SUMO wrestling with type 1 diabetes. J Mol Med 83:504-513.
56. Ueda, H., Goto, J., Hashida, H., Lin, X., Oyanagi, K., Kawano, H., Zoghbi, H. Y., Kanazawa, I., and Okazawa, H. 2002. Enhanced SUMOylation in polyglutamine diseases. Biochem Biophys Res Commun 293:307-313.
57. Sufan, R. I., Jewett, M. A., and Ohh, M. 2004. The role of von Hippel-Lindau tumor suppressor protein and hypoxia in renal clear cell carcinoma. Am J Physiol Renal Physiol 287:F1-6.
58. Wada, H., Yeh, E. T., and Kamitani, T. 1999. The von Hippel-Lindau tumor suppressor gene product promotes, but is not essential for, NEDD8 conjugation to cullin-2. J Biol Chem 274:36025-36029.
59. Shishido, T., Woo, C. H., Ding, B., McClain, C., Molina, C. A., Yan, C., Yang, J., and Abe, J. 2008. Effects of MEK5/ERK5 association on small ubiquitin-related modification of ERK5: implications for diabetic ventricular dysfunction after myocardial infarction. Circ Res 102:1416-1425.
60. Ciechanover, A., and Brundin, P. 2003. The ubiquitin proteasome system in neurodegenerative diseases: sometimes the chicken, sometimes the egg. Neuron 40:427-446.
61. Kim, J. K., Mastronardi, F. G., Wood, D. D., Lubman, D. M., Zand, R., and Moscarello, M. A. 2003. Multiple sclerosis: an important role for PTMs of myelin basic protein in pathogenesis. Mol Cell Proteomics 2:453-462.
62. Matei, L. 1997. Plasma proteins glycosylation and its alteration in disease. Rom J Intern Med 35:3-11.
63. Shinbo, Y., Niki, T., Taira, T., Ooe, H., Takahashi-Niki, K., Maita, C., Seino, C., Iguchi-Ariga, S. M., and Ariga, H. 2006. Proper SUMO-1 conjugation is essential to DJ-1 to exert its full activities. Cell Death Differ 13:96-108.
64. Zhong, N., Kim, C. Y., Rizzu, P., Geula, C., Porter, D. R., Pothos, E. N., Squitieri, F., Heutink, P., and Xu, J. 2006. DJ-1 transcriptionally up-regulates the human tyrosine hydroxylase by inhibiting the sumoylation of pyrimidine tract-binding protein-associated splicing factor. J Biol Chem 281:20940-20948.
65. Brooks, C. L., and Gu, W. 2003. Ubiquitination, phosphorylation and acetylation: the molecular basis for p53 regulation. Curr Opin Cell Biol 15:164-171.
66. Casalino, L., De Cesare, D., and Verde, P. 2003. Accumulation of Fra-1 in ras-transformed cells depends on both transcriptional autoregulation and MEK-dependent posttranslational stabilization. Mol Cell Biol 23:4401-4415.
67. Fujioka, S., Sclabas, G. M., Schmidt, C., Niu, J., Frederick, W. A., Dong, Q. G., Abbruzzese, J. L., Evans, D. B., Baker, C., and Chiao, P. J. 2003. Inhibition of constitutive NF-kappa B activity by I kappa B alpha M suppresses tumorigenesis. Oncogene 22:1365-1370.
68. Lee, P. S., Chang, C., Liu, D., and Derynck, R. 2003. Sumoylation of Smad4, the common Smad mediator of transforming growth factor-beta family signaling. J Biol Chem 278:27853-27863.
69. Orii, A., Masutani, H., Nikaido, T., Zhai, Y. L., Kato, K., Kariya, M., Konishi, I., Yodoi, J., and Fujii, S. 2002. Altered PTM of redox factor 1 protein in human uterine smooth muscle tumors. J Clin Endocrinol Metab 87:3754-3759.
70. Turenne, G. A., and Price, B. D. 2001. Glycogen synthase kinase3 beta phosphorylates serine 33 of p53 and activates p53's transcriptional activity. BMC Cell Biol 2:12.
71. O'Connor, T. J., Neufeld, E., Bechberger, J., and Fujita, D. J. 1992. pp60c-src in human melanocytes and melanoma cells exhibits elevated specific activity and reduced tyrosine 530 phosphorylation compared to human fibroblast pp60c-src. Cell Growth Differ 3:435-442.

72. Reynolds, F. H., Jr., Van de Ven, W. J., and Stephenson, J. R. 1980. Abelson murine leukemia virus transformation-defective mutants with impaired P120-associated protein kinase activity. J Virol 36:374-386.
73. Haraguchi, T., Fisher, S., Olofsson, S., Endo, T., Groth, D., Tarentino, A., Borchelt, D. R., Teplow, D., Hood, L., Burlingame, A., et al. 1989. Asparagine-linked glycosylation of the scrapie and cellular prion proteins. Arch Biochem Biophys 274:1-13.
74. Kalb, R., Neveling, K., Nanda, I., Schindler, D., and Hoehn, H. 2006. Fanconi anemia: causes and consequences of genetic instability. Genome Dyn 1:218-242.
75. Meetei, A. R., de Winter, J. P., Medhurst, A. L., Wallisch, M., Waisfisz, Q., van de Vrugt, H. J., Oostra, A. B., Yan, Z., Ling, C., Bishop, C. E., et al. 2003. A novel ubiquitin ligase is deficient in Fanconi anemia. Nat Genet 35:165-170.
76. Grillari, J., Katinger, H., and Voglauer, R. 2006. Aging and the ubiquitinome: traditional and non-traditional functions of ubiquitin in aging cells and tissues. Exp Gerontol 41:1067-1079.
77. Li, F., Zhang, L., Craddock, J., Bruce-Keller, A. J., Dasuri, K., Nguyen, A., and Keller, J. N. 2008. Aging and dietary restriction effects on ubiquitination, sumoylation, and the proteasome in the heart. Mech Ageing Dev 129:515-521.
78. Li, W., Gao, B., Lee, S. M., Bennett, K., and Fang, D. 2007. RLE-1, an E3 ubiquitin ligase, regulates C. elegans aging by catalyzing DAF-16 polyubiquitination. Dev Cell 12:235-246.
79. Zhang, L., Li, F., Dimayuga, E., Craddock, J., and Keller, J. N. 2007. Effects of aging and dietary restriction on ubiquitination, sumoylation, and the proteasome in the spleen. FEBS Lett 581:5543-5547.
80. Gaczynska, M., Osmulski, P. A., and Ward, W. F. 2001. Caretaker or undertaker? The role of the proteasome in aging. Mech Ageing Dev 122:235-254.
81. Yao, D., Gu, Z., Nakamura, T., Shi, Z. Q., Ma, Y., Gaston, B., Palmer, L. A., Rockenstein, E. M., Zhang, Z., Masliah, E., et al. 2004. Nitrosative stress linked to sporadic Parkinson's disease: S-nitrosylation of parkin regulates its E3 ubiquitin ligase activity. Proc Natl Acad Sci USA 101:10810-10814.
82. Blough, H. A., Pauwels, R., De Clercq, E., Cogniaux, J., Sprecher-Goldberger, S., and Thiry, L. 1986. Glycosylation inhibitors block the expression of LAV/HTLV-III (HIV) glycoproteins. Biochem Biophys Res Commun 141:33-38.
83. Conrad, S. F., Byeon, I. J., DiGeorge, A. M., Lairmore, M. D., Tsai, M. D., and Kaumaya, P. T. 1995. Immunogenicity and conformational properties of an N-linked glycosylated peptide epitope of human T-lymphotropic virus type 1 (HTLV-I). Biomed Pept Proteins Nucleic Acids 1:83-92.
84. Lee, S., Shin, Y., Marler, J., and Levin, M. C. 2008. Post-translational glycosylation of target proteins implicate molecular mimicry in the pathogenesis of HTLV-1 associated neurological disease. J Neuroimmunol.
85. Schneider, J., Bayer, H., Bienzle, U., and Hunsmann, G. 1985. A glycopolypeptide (gp 100) is the main antigen detected by HTLV-III antisera. Med Microbiol Immunol 174:35-42.
86. Harauz, G., and Musse, A. A. 2007. A tale of two citrullines—structural and functional aspects of myelin basic protein deimination in health and disease. Neurochem Res 32:137-158.
87. Akimoto, Y., Hart, G. W., Hirano, H., and Kawakami, H. 2005. O-GlcNAc modification of nucleocytoplasmic proteins and diabetes. Med Mol Morphol 38:84-91.
88. Dias, W. B., and Hart, G. W. 2007. O-GlcNAc modification in diabetes and Alzheimer's disease. Mol Biosyst 3:766-772.
89. Jones, S. P. 2005. A bittersweet modification: O-GlcNAc and cardiac dysfunction. Circ Res 96:925-926.
90. Kudlow, J. E. 2006. PTM by O-GlcNAc: another way to change protein function. J Cell Biochem 98:1062-1075.
91. Doyle, H. A., and Mamula, M. J. 2002. Posttranslational protein modifications: new flavors in the menu of autoantigens. Curr Opin Rheumatol 14:244-249.
92. Doyle, H. A., and Mamula, M. J. 2005. Posttranslational modifications of self-antigens. Ann N Y Acad Sci 1050: 1-9.
93. van Boekel, M. A., and van Venrooij, W. J. 2003. Modifications of arginines and their role in autoimmunity. Autoimmun Rev 2:57-62.
94. Zhou, Z., and Menard, H. A. 2002. Autoantigenic posttranslational modifications of proteins: does it apply to rheumatoid arthritis? Curr Opin Rheumatol 14:250-253.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

SEQUENCE LISTING

```
Sequence total quantity: 2
SEQ ID NO: 1            moltype = AA  length = 76
FEATURE                 Location/Qualifiers
source                  1..76
                        mol_type = protein
                        organism = Homo sapiens
SEQUENCE: 1
MQIFVKTLTG KTITLEVEPS DTIENVKAKI QDKEGIPPDQ QRLIFAGKQL EDGRTLSDYN  60
IQKESTLHLV LRLRGG                                                  76
```

-continued

```
SEQ ID NO: 2            moltype = AA  length = 4
FEATURE                 Location/Qualifiers
source                  1..4
                        mol_type = protein
                        organism = Homo sapiens
SEQUENCE: 2
DEAD                                                                    4
```

What is claimed is:

1. An assay for determining the post-translational modification (PTM) state of a biological sample from a subject suspected of having a disease or medical condition[in a subject], the[method] *assay* comprising the steps of:

(i) contacting a functional biological sample comprising [proteins]*at least one protein* having PTM enzyme activity with a solid state array, the array comprising an ordered plurality of proteins under conditions that allow post-translational modification (PTM) to occur or that allow PTM to be modified, wherein the PTM is ubiquitination or deubiquitination, wherein the functional biological sample is generated by homogenization of [a]*the* biological sample from [a]*the* subject suspected of having a disease or medical condition in a detergent-free environment, and wherein the functional biological sample is supplemented with an ATP generating system, and wherein the functional biological sample is a bodily fluid;

(ii) identifying post-translationally modified proteins in the solid state array to obtain a PTM state data set that serves as a signature or profile of protein PTMs in the [patient]*subject* generated by the enzymatic activity in the sample; and (iii) comparing the PTM state data set of (ii) with a PTM standard data set that includes PTM state data diagnostic for the disease or medical condition, thereby determining the PTM state of the biological sample from[a] *the* subject suspected of having said disease or medical condition[in the subject].

2. The [method]*assay* of claim 1, wherein the PTM standard data set is generated from PTM data from one or more individuals known to have the disease or medical condition and one or more individuals who do not have the disease or medical condition.

3. The [method]*assay* of claim 1, further comprising performing step (i) in the presence and absence of a drug, and comparing the pattern of protein PTM obtained under the [effects]*presence* of [a] *the* drug to the pattern of PTM obtained in the absence of the drug.

4. The [method]*assay* of claim 3, wherein [the] changes in the pattern of protein *PTM* under the [effects] *presence* of a drug are obtained by comparing samples obtained from the subject before and after administration of the drug.

5. The [method]*assay* of claim *1*, wherein the *functional* biological sample is a bodily fluid selected from the group consisting of serum, plasma, and cerebrospinal fluid.

6. The [method]*assay* of claim 1, wherein the functional biological sample [is] *is a cell extract* obtained from a frozen or cryopreserved biological sample.

7. The [method]*assay* of claim 1, wherein the array comprising a plurality of proteins, comprises at least one protein, protein fragment or peptide attached to the array without an added tag.

8. The [method] *assay* of claim 1, wherein the array comprising a plurality of proteins comprises at least one protein, protein fragment or peptide attached to the array with a C-terminal or N-terminal tag.

9. The [method]*assay* of claim 1, wherein a plurality of PTM or PTM alterations thereof are identified simultaneously.

10. The [method]*assay* of claim 1, wherein the solid state array is selected from the group consisting of protein arrays on microchips, ELISA plates with immobilized proteins attached on the plates, protein-coated beads, and microfluidic chips coated with desired proteins.

11. The [method]*assay* of claim 1, wherein the identifying is performed using an antibody or antigen-binding fragment thereof, a natural or recombinant ligand, a small molecule, a modifying moiety, or a biochemical analysis capable of detecting the PTM or PTM alteration.

12. The [method]*assay* of claim 11, wherein the comparison produces a pattern of protein PTM that is diagnostic for a disease or medical condition.

* * * * *